United States Patent
Nash et al.

(10) Patent No.: US 10,829,441 B2
(45) Date of Patent: Nov. 10, 2020

(54) REACTIVE OXYGEN SPECIES-SENSITIVE NITRIC OXIDE SYNTHASE INHIBITORS FOR THE TREATMENT OF ISCHEMIC STROKE

(71) Applicant: The University of Toledo, Toledo, OH (US)

(72) Inventors: Kevin M. Nash, Toledo, OH (US); Isaac Schiefer, Toledo, OH (US); Zahoor Shah, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 16/176,254

(22) Filed: Oct. 31, 2018

(65) Prior Publication Data
US 2019/0144377 A1    May 16, 2019

Related U.S. Application Data

(60) Provisional application No. 62/585,916, filed on Nov. 14, 2017.

(51) Int. Cl.
| | |
|---|---|
| *C07C 259/02* | (2006.01) |
| *C07C 257/14* | (2006.01) |
| *A61P 9/10* | (2006.01) |
| *C07C 251/48* | (2006.01) |
| *C07C 335/32* | (2006.01) |
| *C07C 279/36* | (2006.01) |
| *C07C 291/02* | (2006.01) |

(52) U.S. Cl.
CPC ............. *C07C 257/14* (2013.01); *A61P 9/10* (2018.01); *C07C 251/48* (2013.01); *C07C 279/36* (2013.01); *C07C 291/02* (2013.01); *C07C 335/32* (2013.01)

(58) Field of Classification Search
CPC .................................................. C07C 259/02
See application file for complete search history.

(56) References Cited

U.S. PATENT DOCUMENTS

| | | | | |
|---|---|---|---|---|
| 3,178,467 A | * | 4/1965 | Smathers et al. | ..... C07C 275/64 549/491 |
| 5,475,032 A | | 12/1995 | Carney | |

OTHER PUBLICATIONS

Han, H. "Targeted Prodrug Design to Optimize Drug Delivery." AAPS Pharmsci. (2000), vol. 2 (1) article 6, pp. 1-11. (Year: 2000).*
Ettmayer, P., et al. "Lessons Learned from Marketed and Investigational Prodrugs." J. Med. Chem. (2004) 47(10), pp. 2393-2404. (Year: 2004).*
Testa, B. "Prodrug research: futile or fertile?" Biochem. Pharm. (2004) 68, pp. 2097-2106. (Year: 2004).*
Chamulitrat, et al., "Phenyl N-Tert-Butyl Nitrone Forms Nitric Oxide as a Result of Its Fe(III)-Catalyzed Hydrolysis or Hydroxyl Radical Adduct Formation", Free Rad. Res., vol. 23, No. 1, 1995, pp. 1-14.

\* cited by examiner

*Primary Examiner* — John S Kenyon
(74) *Attorney, Agent, or Firm* — MacMillan, Sobanski & Todd, LLC

(57) ABSTRACT

Disclosed are ROS-sensitive NOS inhibitors, as well as methods of making and using the same.

23 Claims, 68 Drawing Sheets
(51 of 68 Drawing Sheet(s) Filed in Color)

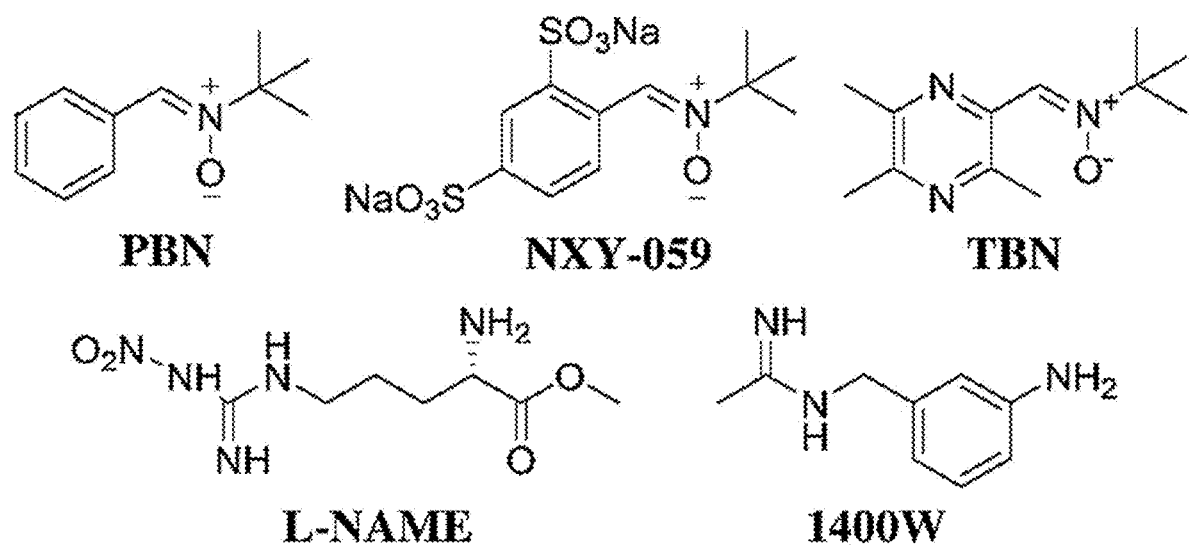
PRIOR ART FIG. 1B

| | | |
|---|---|---|
| | 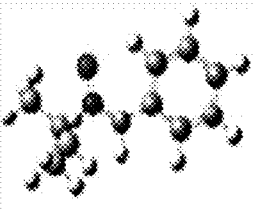 | 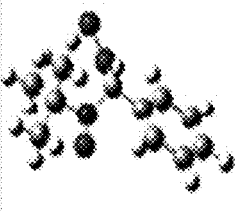 |
| Compound | PBN | PBN-O2 |
| file | PBN.log | PBN-O2.log |
| E 6-31+g** tight | -558.1753974 | -708.6295898 |
| E 6-31g* | -558.1229151 | -708.4689312 |
| ZPE (raw) | 0.2402741 | 0.2452808 |
| Therm Corr to H (raw) | 0.254034 | 0.260894 |
| Therm Corr to G (raw) | 0.199693 | 0.203307 |
| H (raw) | | |
| G (raw) | | |
| ZPE (scaled) | 0.235613 | 0.240522 |
| Electronic State | 1-A | 2-A |
| s2 6-31g* | 0 | 0.754042 |
| Symmetry | * | * |
| N Imag | 0 | 0 |
| Rotational Con. (GHz) | 2.0228295 | 1.1568872 |
| Rotational Con. (GHz) | 0.4019737 | 0.3895863 |
| Rotational Con. (GHz) | 0.3626709 | 0.3302713 |
| H298 | | 7.3 |
| 6-31+g** tight | -557.926025 | -708.373454 |
| 6-31g* tight | -557.873542 | -708.212796 |
| G298 | | 19.8 |
| 6-31+g** tight | -557.980366 | -708.431041 |
| 6-31g* tight | -557.927883 | -708.270383 |
FIG. 5A

| | | |
|---|---|---|
|  | 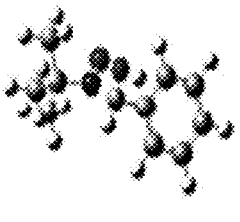 | 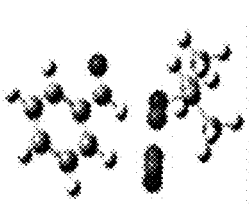 |
| PBN-O2H | PBN-OH | PBN-cOONO |
| PBN-O2H.log | PBN-OH.log | PBN-cOONO.log |
| -709.1215789 | -633.9888874 | -838.6426924 |
| -709.05267 | -633.9248441 | -838.485894 |
| 0.2582605 | 0.2553993 | 0.2493463 |
| 0.274992 | 0.270696 | 0.270432 |
| 0.214213 | 0.213551 | 0.196311 |
| | | |
| | | |
| 0.253250 | 0.250445 | 0.244509 |
| 2-A | 2-A | 1-A |
| 0.753684 | 0.753597 | 0 |
| * | | * |
| 0 | | 0 |
| 1.0626812 | 1.5260768 | 0.6130537 |
| 0.3800827 | 0.3833158 | 0.2675786 |
| 0.3457177 | 0.3771236 | 0.2542705 |
| -10.2 | -43.7 | -44.8 |
| -708.851597 | -633.723146 | -838.377098 |
| -708.782688 | -633.659103 | -838.220299 |
| 2.1 | -32.7 | -38.1 |
| -708.912376 | -633.780291 | -838.451219 |
| -708.843467 | -633.716248 | -838.294420 |
FIG. 5A cont.

| PBN-cOONO Triplet | PBN-tHOONO Triplet |
|---|---|
| PBN-cOONO-DR | PBN-tHOONO-b.log |
| -838.5387083 | -839.0780859 |
| -838.3831309 | -839.0079195 |
| 0.2521946 | 0.265531 |
| 0.270965 | 0.285543 |
| 0.204959 | 0.212382 |
| | |
| | |
| 0.247302 | 0.260380 |
| 3-A | 3-A |
| 2.009709 | 2.007412 |
| * | * |
| 0 | 0 |
| 0.6496567 | 0.5317328 |
| 0.3560352 | 0.330638 |
| 0.2596329 | 0.250924 |
| 20.8 | -31.0 |
| -838.272636 | -838.797694 |
| -838.117058 | -838.727528 |
| 32.5 | -23.4 |
| -838.338642 | -838.870855 |
| -838.183064 | -838.800689 |

FIG. 5A cont.

| | |
|---|---|
| Compound | Nitrone5 |
| file | Nitrone5.log |
| E 6-31+g** tight | -785.6357585 |
| E 6-31g* | -785.553248 |
| ZPE (raw) | 0.3364848 |
| Therm Corr to H (raw) | 0.356426 |
| Therm Corr to G (raw) | 0.286235 |
| H (raw) | |
| G (raw) | |
| ZPE (scaled) | 0.329957 |
| Electronic State | 1-A |
| s2 6-31g* | 0 |
| Symmetry | - |
| N Imag | 0 |
| Rotational Con. (GHz) | 0.6810234 |
| Rotational Con. (GHz) | 0.1725886 |
| Rotational Con. (GHz) | 0.1465231 |
| H298 | |
| 6-31+g** tight | -785.285860 |
| 6-31g* tight | -785.203350 |
| G298 | |
| 6-31+g** tight | -785.356051 |
| 6-31g* tight | -785.273541 |

FIG. 5B

| 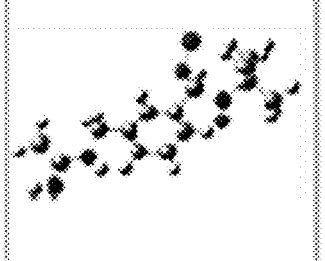 | 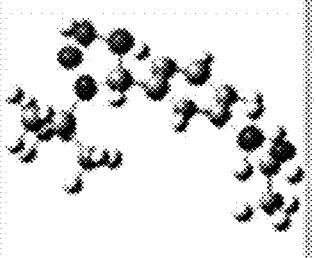 |
|---|---|
| Nitrone5-O2 | Nitrone5-O2H |
| Nitrone5-O2.log | Nitrone5-O2H.log |
| -936.0904947 | -936.5851853 |
| -935.902876 | -936.4902325 |
| 0.3413772 | 0.3551733 |
| 0.36327 | 0.377663 |
| 0.289719 | 0.301437 |
| | |
| | |
| 0.334754 | 0.348283 |
| 2-A | 2-A |
| 0.750012 | 0.754036 |
| * | * |
| 0 | 0 |
| 0.8199599 | 0.5214058 |
| 0.1293767 | 0.1597197 |
| 0.1226153 | 0.1520779 |
| 6.9 | -12.1 |
| -935.733847 | -936.214413 |
| -935.546229 | -936.119460 |
| 19.3 | 0.4 |
| -935.807398 | -936.290639 |
| -935.619780 | -936.195686 |
FIG. 5B cont.

| 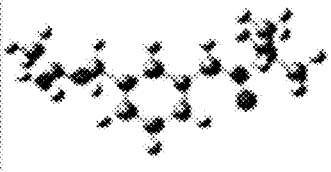 | 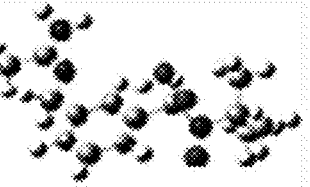 |
|---|---|
| Nitrone5H | Nitrone5H-O2 |
| Nitrone5H.log | Nitrone5H-O2.log |
| -786.1034327 | -936.5828289 |
| -785.9601173 | -936.4881889 |
| 0.349638 | 0.353687 |
| 0.37001 | 0.376723 |
| 0.299859 | 0.299649 |
| | |
| | |
| 0.342856 | 0.346826 |
| 1-A | 2-A |
| 0 | 0.753653 |
| - | - |
| 0 | 0 |
| 0.9140464 | 0.49675 |
| 0.1448533 | 0.16514 |
| 0.1348986 | 0.14509 |
| | -8.6 |
| -785.740206 | -936.212967 |
| -785.596890 | -936.118327 |
| | 1.6 |
| -785.810357 | -936.290041 |
| -785.667041 | -936.195401 |
FIG. 5B cont.

| | |
|---|---|
| 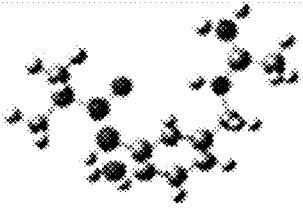 | 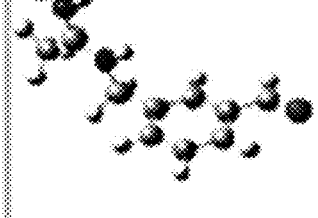 |
| Nitrone5H-O2H | 6 |
| Nitrone5H-O2H | Inh5H-Ald.log |
| -937.0470166 | -573.5323419 |
| -936.8975349 | -573.4013846 |
| 0.3677559 | 0.2193848 |
| 0.391074 | 0.233299 |
| 0.313683 | 0.178218 |
| | |
| | |
| 0.360621 | 0.215129 |
| 2-A | 1-A |
| 0.753838 | 0 |
| * | * |
| 0 | 0 |
| 0.447046 | 1.7985325 |
| 0.2003035 | 0.3241078 |
| 0.1661309 | 0.301647 |
| -8.5 | |
| -936.663077 | -573.303299 |
| -936.513595 | -573.172342 |
| 3.2 | |
| -936.740468 | -573.358380 |
| -936.590986 | -573.227423 |
FIG. 5B cont.

| Compound | N5H-cOONO-Triplet | N5H-tOONO-Triplet |
|---|---|---|
| file | Nitrone5H-cOONOr.o | Nitrone5H-tOONOr.cor |
| E 6-31+g** tight | -1066.526598 | -1066.465825 |
| E 6-31g* | -1066.41267 | -1066.351577 |
| ZPE(raw) | 0.3604898 | 0.3621789 |
| Therm Corr to H(raw) | 0.385945 | 0.386455 |
| Therm Corr to G(raw) | 0.302557 | 0.308231 |
| H(raw) | | |
| G(raw) | | |
| ZPE(scaled) | 0.353496 | 0.355153 |
| Electronic State | 3-A | 3-A |
| s2 6-31g* | 2.007249 | 2.008104 |
| Symmetry | - | - |
| Nimag | 0 | 0 |
| Rotational Con. (GHz) | 0.45994 | 0.4844277 |
| Rotational Con. (GHz) | 0.1585 | 0.1642448 |
| Rotational Con. (GHz) | 0.1291 | 0.133341 |
| H298 | -17.4 | 16.8 |
| 6-31+g** tight | -1066.147647 | -1066.086396 |
| 6-31g* tight | -1066.033718 | -1065.972148 |
| G298 | -6.7 | 30.9 |
| 6-31+g** tight | -1066.231035 | -1066.164620 |
| 6-31g* tight | -1066.117106 | -1066.050372 |

FIG. 5C

|  | 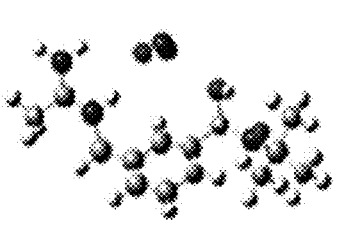 |
|---|---|
| N5H-cHOONO-Triplet | N5H-tHOONO-Triplet |
| Nitrone5H-cHOONOr.α | Nitrone5H-tHOONOr.c |
| -1067.005068 | -1067.003533 |
| -1066.846266 | -1066.849762 |
| 0.3751124 | 0.3752402 |
| 0.401823 | 0.401728 |
| 0.311996 | 0.314722 |
| | |
| | |
| 0.367835 | 0.367961 |
| 3-A | 3-A |
| 2.006967 | 2.007148 |
| - | - |
| 0 | 0 |
| 0.3927496 | 0.4906829 |
| 0.1569542 | 0.1437159 |
| 0.1308911 | 0.1244843 |
| -27.0 | -29.3 |
| -1066.610522 | -1066.609084 |
| -1066.451721 | -1066.455314 |
| -19.9 | -20.4 |
| -1066.700349 | -1066.696090 |
| -1066.541548 | -1066.542320 |
FIG. 5C cont.

| Compound | N5H-cOONO | N5H-tOONO |
|---|---|---|
| file | Nitrone5H-cOON( | Nitrone5H-tOON( |
| E 6-31+g** tight | -1066.593684 | -1066.581989 |
| E 6-31g* | -1066.48573 | -1066.477735 |
| ZPE (raw) | 0.359003 | 0.358707 |
| Therm Corr to H (ra | 0.385789 | 0.386051 |
| Therm Corr to G (ra | 0.299768 | 0.294497 |
| H (raw) | | |
| G (raw) | | |
| ZPE (scaled) | 0.352036 | 0.351811 |
| Electronic State | 1-A | 1-A |
| s2 6-31g* | 0 | 0 |
| Symmetry | - | - |
| Nimag | 0 | 0 |
| Rotational Con. (GHz | 0.3247771 | 0.2938049 |
| Rotational Con. (GHz | 0.209315 | 0.1094194 |
| Rotational Con. (GHz | 0.1535112 | 0.0904139 |
| H298 | -59.6 | -56.3 |
| 6-31+g** tight | -1066.214860 | -1066.202898 |
| 6-31g* tight | -1066.106905 | -1066.098644 |
| G298 | -50.5 | -50.6 |
| 6-31+g** tight | -1066.300880 | -1066.294452 |
| 6-31g* tight | -1066.192925 | -1066.190198 |

FIG. 5D

| N5H-cHOONO | N5H-tHOONO |
|---|---|
| Nitrone5H-cHOO | Nitrone5H-tHOONO. |
| -1067.005376 | -1067.006791 |
| -1066.864457 | -1066.862848 |
| 0.3780774 | 0.377909 |
| 0.402402 | 0.402327 |
| 0.325924 | 0.325611 |
|  |  |
| 0.370743 | 0.370578 |
| 1-A | 1-A |
| 0 | 0 |
| - | - |
| 0 | 0 |
| 0.477344 | 0.4580586 |
| 0.1921315 | 0.1941952 |
| 0.1627655 | 0.1616104 |
| -26.9 | -31.0 |
| -1066.610309 | -1066.611795 |
| -1066.469389 | -1066.467852 |
| -11.4 | -15.6 |
| -1066.686787 | -1066.688511 |
| -1066.545867 | -1066.544568 |

FIG. 5D cont.

| N5H-O2 + 2H2O | Nitrone 5H-OH |
|---|---|
| Nitrone5H-O2-H2 | Nitrone5H-OH.log |
| -1089.490779 | -861.9135897 |
| -1089.360431 | -861.7677685 |
| 0.406076 | 0.364880B |
| 0.433394 | 0.386758 |
| 0.347854 | 0.312947 |
|  |  |
|  |  |
| 0.398198 | 0.357802 |
| 2-A | 2-A |
| 0.753687 | 0.753771 |
| - | - |
| 0 | 0 |
| 0.4628079 | 0.5085957 |
| 0.1314551 | 0.2251992 |
| 0.1193807 | 0.1785217 |
| -19.2 | -41.5 |
| -1089.065263 | -861.533910 |
| -1088.934915 | -861.388089 |
| 12.6 | -31.1 |
| -1089.150803 | -861.607721 |
| -1089.020455 | -861.461900 |

FIG. 5D cont.

| | | |
|---|---|---|
| Compound | HO₂ | O2 |
| file | superH.com.log | super.com.log |
| E 6-31+g** tight | -150.926851 | -150.465075 |
| E 6-31g* | -150.8991565 | -150.2996938 |
| ZPE (raw) | 0.014031 | 0.002761 |
| Therm Corr to H (ra | 0.017832 | 0.006082 |
| Therm Corr to G (ra | -0.00816 | -0.017041 |
| H (raw) | | |
| G (raw) | | |
| ZPE (scaled) | 0.013759 | 0.002707 |
| Electronic State | 2-A" | — |
| s2 6-31g* | 0.754 | 0.756 |
| Symmetry | - | - |
| NImag | 0.000000 | 0.000000 |
| Rotational Con. (GH | 608.8470994 | 0 |
| Rotational Con. (GH | 33.5599447 | 34.5113404 |
| Rotational Con. (GH | 31.8067418 | 34.5113404 |
| H298 | | |
| 6-31+g** tight | -150.909291 | -150.459047 |
| 6-31g* tight | -150.881597 | -150.293665 |
| G298 | | |
| 6-31+g** tight | -150.935283 | -150.482170 |
| 6-31g* tight | -150.907589 | -150.316788 |

FIG. 5E

| HO | H2O |
|---|---|
| Hydrox.log | H2O.log |
| -75.7389891 | -76.4422582 |
| -75.7234548 | -76.4089533 |
| 0.0083041 | 0.0211685 |
| 0.011609 | 0.024947 |
| -0.008638 | 0.003501 |
|  |  |
|  |  |
| 0.008143 | 0.020758 |
| - | 1-A |
| 0.751967 | 0 |
| * | - |
| 0 | 0 |
| 0 | 787.909196 |
| 551.744617 | 432.3087586 |
| 551.744617 | 279.1468894 |
|  |  |
| -75.727541 | -76.417722 |
| -75.712007 | -76.384417 |
|  |  |
| -75.747788 | -76.439168 |
| -75.732254 | -76.405863 |

FIG. 5E cont.

| cOONO | tOONO |
|---|---|
| cOONO.log | tOONO.log |
| -280.3954815 | -280.3883917 |
| -280.2500382 | -280.2434027 |
| 0.0114255 | 0.0108351 |
| 0.015985 | 0.015605 |
| -0.014355 | -0.01486 |
|  |  |
| 0.011204 | 0.010625 |
| 1-A | 1-A |
| 0 | 0 |
| * | * |
| 0 | 0 |
| 24.1507663 | 76.2586328 |
| 7.6620056 | 5.10126 |
| 5.8166359 | 4.7814114 |
|  |  |
| -280.379718 | -280.372997 |
| -280.234275 | -280.228008 |
|  |  |
| -280.410058 | -280.403462 |
| -280.264615 | -280.258473 |

FIG. 5E cont.

|  cHOONO | tHOONO |
|---|---|
| cHOONO.log | tHOONO.log |
| -280.8553735 | -280.8492933 |
| -280.8315481 | -280.8212281 |
| 0.0236257 | 0.0225121 |
| 0.028533 | 0.027479 |
| -0.002383 | -0.00353 |
|  |  |
|  |  |
| 0.023167 | 0.022075 |
| 1-A | 1-A |
|  | 0 |
|  | * |
|  | 0 |
| 21.4709468 | 57.601434 |
| 7.956318 | 4.971635 |
| 5.8051498 | 4.5766224 |
|  |  |
| -280.827299 | -280.822251 |
| -280.803473 | -280.794186 |
|  |  |
| -280.858215 | -280.853260 |
| -280.834389 | -280.825195 |

FIG. 5E cont.

| S-eNOS(L-Arginine) | | | S-nNOS(L-Arginine) | | | S-iNOS(L-Arginine) | |
|---|---|---|---|---|---|---|---|
| Energy | -15.716 | | Energy | -16.558 | | Energy | -23.7129 |
| SimpleFitness | -15.716 | | SimpleFitness | -16.558 | | SimpleFitness | -23.7129 |
| FullFitness | -2026.81 | | FullFitness | -2187.41 | | FullFitness | -2238.81 |
| InterFull | -100.245 | | InterFull | -89.6863 | | InterFull | -112.053 |
| IntraFull | 9.10902 | | IntraFull | 1.8422 | | IntraFull | 2.98932 |
| solvFull | -2233.58 | | solvFull | -2412.77 | | solvFull | -2434.46 |
| surfFull | 297.909 | | surfFull | 313.206 | | surfFull | 304.712 |
| extraFull | 0 | | extraFull | 0 | | extraFull | 0 |
| deltaGcompsolvpol | -2233.58 | | deltaGcompsolvpol | -2412.77 | | deltaGcompsolvpol | -2434.46 |
| deltaGcompsolvnonpol | 297.909 | | deltaGcompsolvnonpol | 313.206 | | deltaGcompsolvnonpol | 304.712 |
| deltaGprotsolvpol | -2268.57 | | deltaGprotsolvpol | -2460.55 | | deltaGprotsolvpol | -2486.33 |
| deltaGprotsolvnonpol | 299.405 | | deltaGprotsolvnonpol | 315.706 | | deltaGprotsolvnonpol | 306.538 |
| deltaGligsolvpol | -35.9009 | | deltaGligsolvpol | -34.6086 | | deltaGligsolvpol | -34.9496 |
| deltaGligsolvnonpol | 6.88548 | | deltaGligsolvnonpol | 6.5882 | | deltaGligsolvnonpol | 6.59309 |
| deltaGvdw | -100.245 | | deltaGvdw | -89.6863 | | deltaGvdw | -112.053 |
| deltaGelec | 0 | | deltaGelec | 0 | | deltaGelec | 0 |
| deltaG | -9.92754 | | deltaG | -8.29188 | | deltaG | -10.0733 |
| Cluster | 0 | | Cluster | 8 | | Cluster | 0 |
| ClusterRank | 1 | | ClusterRank | 0 | | ClusterRank | 0 |
| S-eNOS(1400W) | | | S-nNOS(1400W) | | | S-iNOS(1400W) | |
| Energy | -14.9436 | | Energy | -23.1567 | | Energy | -26.572 |
| SimpleFitness | -14.9436 | | SimpleFitness | -23.1567 | | SimpleFitness | -26.572 |
| FullFitness | -3989.59 | | FullFitness | -2516.59 | | FullFitness | -4311.7 |
| InterFull | -107.636 | | InterFull | -100.051 | | InterFull | -117.937 |
| IntraFull | 10.5244 | | IntraFull | 2.66276 | | IntraFull | 3.10626 |
| solvFull | -4407.65 | | solvFull | -2732.51 | | solvFull | -4800.8 |
| surfFull | 515.174 | | surfFull | 313.304 | | surfFull | 602.93 |
| extraFull | 0 | | extraFull | 0 | | extraFull | 0 |
| deltaGcompsolvpol | -4407.65 | | deltaGcompsolvpol | -2732.51 | | deltaGcompsolvpol | -4800.8 |
| deltaGcompsolvnonpol | 515.174 | | deltaGcompsolvnonpol | 313.304 | | deltaGcompsolvnonpol | 602.93 |
| deltaGprotsolvpol | -4451.84 | | deltaGprotsolvpol | -2768.03 | | deltaGprotsolvpol | -4850.39 |
| deltaGprotsolvnonpol | 516.682 | | deltaGprotsolvnonpol | 314.623 | | deltaGprotsolvnonpol | 604.61 |
| deltaGligsolvpol | -34.8527 | | deltaGligsolvpol | -35.0992 | | deltaGligsolvpol | -35.11 |
| deltaGligsolvnonpol | 6.73492 | | deltaGligsolvnonpol | 6.62188 | | deltaGligsolvnonpol | 6.59667 |
| deltaGvdw | -107.636 | | deltaGvdw | -100.051 | | deltaGvdw | -117.937 |
| deltaGelec | 0 | | deltaGelec | 0 | | deltaGelec | 0 |
| deltaG | -10.1147 | | deltaG | -9.88414 | | deltaG | -10.7462 |
| Cluster | 1 | | Cluster | 0 | | Cluster | 0 |
| ClusterRank | 0 | | ClusterRank | 0 | | ClusterRank | 0 |

FIG. 6A

| 6-eNOS(L-Arginine) | | 6-nNOS(L-Arginine) | | 6-iNOS(L-Arginine) | |
|---|---|---|---|---|---|
| Energy | -28.443 | Energy | -23.4341 | Energy | -28.027 |
| SimpleFitness | -28.443 | SimpleFitness | -23.4341 | SimpleFitness | -28.027 |
| FullFitness | -2032.56 | FullFitness | -2200.21 | FullFitness | -2239.06 |
| InterFull | -99.7369 | InterFull | -87.646 | InterFull | -107.325 |
| IntraFull | 1.37044 | IntraFull | 4.22401 | IntraFull | 5.20546 |
| solvFull | -2232.34 | solvFull | -2431.51 | solvFull | -2442.02 |
| surfFull | 298.145 | surfFull | 314.72 | surfFull | 305.081 |
| extraFull | 0 | extraFull | 0 | extraFull | 0 |
| deltaGcompsolvpol | -2232.34 | deltaGcompsolvpol | -2431.51 | deltaGcompsolvpol | -2442.02 |
| deltaGcompsolvnonpol | 298.145 | deltaGcompsolvnonpol | 314.72 | deltaGcompsolvnonpol | 305.081 |
| deltaGprotsolvpol | -2268.57 | deltaGprotsolvpol | -2460.95 | deltaGprotsolvpol | -2486.33 |
| deltaGprotsolvnonpol | 299.405 | deltaGprotsolvnonpol | 315.706 | deltaGprotsolvnonpol | 306.538 |
| deltaGligsolvpol | -33.2622 | deltaGligsolvpol | -35.9563 | deltaGligsolvpol | -36.7225 |
| deltaGligsolvnonpol | 4.62845 | deltaGligsolvnonpol | 4.58891 | deltaGligsolvnonpol | 4.60597 |
| deltaGvdw | -99.7369 | deltaGvdw | -87.646 | deltaGvdw | -107.325 |
| deltaGelec | 0 | deltaGelec | 0 | deltaGelec | 0 |
| deltaG | -9.72924 | deltaG | -8.83092 | deltaG | -9.75731 |
| Cluster | 0 | Cluster | 0 | Cluster | 0 |
| ClusterRank | 0 | ClusterRank | 0 | ClusterRank | 0 |
| 6-eNOS(1400W) | | 6-nNOS(1400W) | | 6-iNOS(1400W) | |
| Energy | -29.8121 | Energy | -26.2413 | Energy | -27.8916 |
| SimpleFitness | -29.8121 | SimpleFitness | -26.2413 | SimpleFitness | -27.8916 |
| FullFitness | -4001.77 | FullFitness | -2517.46 | FullFitness | -4311.71 |
| InterFull | -99.7834 | InterFull | -99.2474 | InterFull | -106.04 |
| IntraFull | 0.384028 | IntraFull | 4.97197 | IntraFull | 4.33722 |
| solvFull | -4417.99 | solvFull | -2736.95 | solvFull | -4813.67 |
| surfFull | 515.623 | surfFull | 313.767 | surfFull | 603.676 |
| extraFull | 0 | extraFull | 0 | extraFull | 0 |
| deltaGcompsolvpol | -4417.99 | deltaGcompsolvpol | -2736.95 | deltaGcompsolvpol | -4813.67 |
| deltaGcompsolvnonpol | 515.623 | deltaGcompsolvnonpol | 313.767 | deltaGcompsolvnonpol | 603.676 |
| deltaGprotsolvpol | -4451.84 | deltaGprotsolvpol | -2768.03 | deltaGprotsolvpol | -4850.39 |
| deltaGprotsolvnonpol | 516.682 | deltaGprotsolvnonpol | 314.623 | deltaGprotsolvnonpol | 604.61 |
| deltaGligsolvpol | -32.9622 | deltaGligsolvpol | -36.2637 | deltaGligsolvpol | -36.1445 |
| deltaGligsolvnonpol | 4.64535 | deltaGligsolvnonpol | 4.61525 | deltaGligsolvnonpol | 4.60484 |
| deltaGvdw | -99.7834 | deltaGvdw | -99.2474 | deltaGvdw | -106.04 |
| deltaGelec | 0 | deltaGelec | 0 | deltaGelec | 0 |
| deltaG | -9.88026 | deltaG | -9.77494 | deltaG | -10.086 |
| Cluster | 0 | Cluster | 0 | Cluster | 0 |
| ClusterRank | 0 | ClusterRank | 0 | ClusterRank | 0 |

FIG. 6B

| LArg-eNOS(L-Arginine) | | LArg-nNOS(L-Arginine) | | LArg-iNOS(L-Arginine) | |
|---|---|---|---|---|---|
| Energy | -64.2624 | Energy | -53.87 | Energy | -73.5701 |
| SimpleFitness | -64.2624 | SimpleFitness | -53.87 | SimpleFitness | -73.5701 |
| FullFitness | -2152.13 | FullFitness | -2309.79 | FullFitness | -2364.76 |
| InterFull | -110.135 | InterFull | -75.9569 | InterFull | -130.404 |
| IntraFull | -110.414 | IntraFull | -114.188 | IntraFull | -109.599 |
| solvFull | -2230.04 | solvFull | -2434.64 | solvFull | -2429.92 |
| surfFull | 298.455 | surfFull | 314.997 | surfFull | 305.162 |
| extraFull | 0 | extraFull | 0 | extraFull | 0 |
| deltaGcompsolvpol | -2230.04 | deltaGcompsolvpol | -2434.64 | deltaGcompsolvpol | -2429.92 |
| deltaGcompsolvnonpol | 298.455 | deltaGcompsolvnonpol | 314.997 | deltaGcompsolvnonpol | 305.162 |
| deltaGprotsolvpol | -2258.57 | deltaGprotsolvpol | -2460.55 | deltaGprotsolvpol | -2486.33 |
| deltaGprotsolvnonpol | 299.405 | deltaGprotsolvnonpol | 315.706 | deltaGprotsolvnonpol | 306.538 |
| deltaGligsolvpol | -43.3759 | deltaGligsolvpol | -39.4593 | deltaGligsolvpol | -47.216 |
| deltaGligsolvnonpol | 5.64788 | deltaGligsolvnonpol | 5.78154 | deltaGligsolvnonpol | 5.58371 |
| deltaGvdw | -110.135 | deltaGvdw | -75.9569 | deltaGvdw | -130.404 |
| deltaGelec | 0 | deltaGelec | 0 | deltaGelec | 0 |
| deltaG | -10.0203 | deltaG | -7.78892 | deltaG | -10.6427 |
| Cluster | 0 | Cluster | 11 | Cluster | 1 |
| ClusterRank | 0 | ClusterRank | 3 | ClusterRank | 0 |
| LArg-eNOS(1400W) | | LArg-nNOS(1400W) | | LArg-iNOS(1400W) | |
| Energy | -65.217 | Energy | -59.2048 | Energy | -69.241 |
| SimpleFitness | -65.217 | SimpleFitness | -59.2048 | SimpleFitness | -69.241 |
| FullFitness | -4119.37 | FullFitness | -2627.31 | FullFitness | -4434.49 |
| InterFull | -92.7332 | InterFull | -84.3217 | InterFull | -113.143 |
| IntraFull | -119.275 | IntraFull | -120.056 | IntraFull | -118.567 |
| solvFull | -4423.24 | solvFull | -2736.48 | solvFull | -4808.41 |
| surfFull | 515.88 | surfFull | 313.547 | surfFull | 603.634 |
| extraFull | 0 | extraFull | 0 | extraFull | 0 |
| deltaGcompsolvpol | -4423.24 | deltaGcompsolvpol | -2736.48 | deltaGcompsolvpol | -4808.41 |
| deltaGcompsolvnonpol | 515.88 | deltaGcompsolvnonpol | 313.547 | deltaGcompsolvnonpol | 603.634 |
| deltaGprotsolvpol | -4451.84 | deltaGprotsolvpol | -2768.03 | deltaGprotsolvpol | -4850.39 |
| deltaGprotsolvnonpol | 516.682 | deltaGprotsolvnonpol | 314.623 | deltaGprotsolvnonpol | 604.61 |
| deltaGligsolvpol | -37.7024 | deltaGligsolvpol | -36.4367 | deltaGligsolvpol | -41.3568 |
| deltaGligsolvnonpol | 5.56338 | deltaGligsolvnonpol | 5.55297 | deltaGligsolvnonpol | 5.51108 |
| deltaGvdw | -92.7332 | deltaGvdw | -84.3217 | deltaGvdw | -113.143 |
| deltaGelec | 0 | deltaGelec | 0 | deltaGelec | 0 |
| deltaG | -9.30704 | deltaG | -8.43314 | deltaG | -10.2068 |
| Cluster | 0 | Cluster | 3 | Cluster | 0 |
| ClusterRank | 0 | ClusterRank | 0 | ClusterRank | 0 |

FIG. 6C

| 1400W-eNOS(L-Arginine) | | | 1400W-nNOS(L-Arginine) | | | 1400W-iNOS(L-Arginine) | |
|---|---|---|---|---|---|---|---|
| Energy | -35.436 | | Energy | -34.8197 | | Energy | -69.0512 |
| SimpleFitness | -35.436 | | SimpleFitness | -34.8197 | | SimpleFitness | -69.0512 |
| FullFitness | -2066.4 | | FullFitness | -2248.99 | | FullFitness | -2407.18 |
| InterFull | -132.891 | | InterFull | -140.361 | | InterFull | -128.601 |
| IntraFull | -0.95525 | | IntraFull | -0.96852 | | IntraFull | -148.415 |
| solvFull | -2230.84 | | solvFull | -2422.19 | | solvFull | -2435.34 |
| surfFull | 298.287 | | surfFull | 314.533 | | surfFull | 305.174 |
| extraFull | 0 | | extraFull | 0 | | extraFull | 0 |
| deltaGcompsolvpol | -2230.84 | | deltaGcompsolvpol | -2422.19 | | deltaGcompsolvpol | -2435.34 |
| deltaGcompsolvnonpol | 298.287 | | deltaGcompsolvnonpol | 314.533 | | deltaGcompsolvnonpol | 305.174 |
| deltaGprotsolvpol | -2259.47 | | deltaGprotsolvpol | -2460.55 | | deltaGprotsolvpol | -2486.33 |
| deltaGprotsolvnonpol | 299.42 | | deltaGprotsolvnonpol | 315.706 | | deltaGprotsolvnonpol | 306.538 |
| deltaGligsolvpol | -74.4494 | | deltaGligsolvpol | -74.8673 | | deltaGligsolvpol | -50.3104 |
| deltaGligsolvnonpol | 4.94903 | | deltaGligsolvnonpol | 4.94715 | | deltaGligsolvnonpol | 6.23611 |
| deltaGvdw | -132.891 | | deltaGvdw | -140.361 | | deltaGvdw | -128.601 |
| deltaGelec | 0 | | deltaGelec | 0 | | deltaGelec | 0 |
| deltaG | -10.3684 | | deltaG | -8.6376 | | deltaG | -10.675 |
| Cluster | 0 | | Cluster | 0 | | Cluster | 0 |
| ClusterRank | 0 | | ClusterRank | 0 | | ClusterRank | 0 |
| | | | | | | | |
| 1400W-eNOS(1400W) | | | 1400W-nNOS(1400W) | | | 1400W-iNOS(1400W) | |
| Energy | -34.872 | | Energy | -21.4019 | | Energy | -38.1473 |
| SimpleFitness | -34.872 | | SimpleFitness | -21.4019 | | SimpleFitness | -38.1473 |
| FullFitness | -4044.91 | | FullFitness | -2548.67 | | FullFitness | -4356.38 |
| InterFull | -129.634 | | InterFull | -135.898 | | InterFull | -149.225 |
| IntraFull | -3.77579 | | IntraFull | 1.55357 | | IntraFull | -0.85389 |
| solvFull | -4427.14 | | solvFull | -2727.58 | | solvFull | -4809.8 |
| surfFull | 515.644 | | surfFull | 313.254 | | surfFull | 603.499 |
| extraFull | 0 | | extraFull | 0 | | extraFull | 0 |
| deltaGcompsolvpol | -4427.14 | | deltaGcompsolvpol | -2727.58 | | deltaGcompsolvpol | -4809.8 |
| deltaGcompsolvnonpol | 515.644 | | deltaGcompsolvnonpol | 313.254 | | deltaGcompsolvnonpol | 603.499 |
| deltaGprotsolvpol | -4451.84 | | deltaGprotsolvpol | -2768.03 | | deltaGprotsolvpol | -4850.39 |
| deltaGprotsolvnonpol | 516.682 | | deltaGprotsolvnonpol | 314.623 | | deltaGprotsolvnonpol | 604.61 |
| deltaGligsolvpol | -74.7406 | | deltaGligsolvpol | -76.9882 | | deltaGligsolvpol | -75.6977 |
| deltaGligsolvnonpol | 4.99946 | | deltaGligsolvnonpol | 5.02161 | | deltaGligsolvnonpol | 4.95016 |
| deltaGvdw | -129.634 | | deltaGvdw | -135.898 | | deltaGvdw | -149.225 |
| deltaGelec | 0 | | deltaGelec | 0 | | deltaGelec | 0 |
| deltaG | -10.3788 | | deltaG | -10.2633 | | deltaG | -11.5632 |
| Cluster | 0 | | Cluster | 1 | | Cluster | 0 |
| ClusterRank | 0 | | ClusterRank | 1 | | ClusterRank | 2 |

FIG. 6D

REACTIVE OXYGEN SPECIES-SENSITIVE NITRIC OXIDE SYNTHASE INHIBITORS FOR THE TREATMENT OF ISCHEMIC STROKE

RELATED APPLICATIONS

This application claims priority to U.S. Provisional Application No. 62/585,916 filed under 35 U.S.C. § 111(b) on Nov. 14, 2017, the disclosure of which is incorporated herein by reference in its entirety.

STATEMENT REGARDING FEDERALLY SPONSORED RESEARCH

This invention was made with no government support. The government has no rights in this invention.

BACKGROUND

Ischemic stroke is a leading cause of death and disability, occurring due to the blockage of blood flow to the brain which results in the neuronal and glial hypoxia leading to inflammatory and free radical-mediated cell death. Reactive oxygen species (ROS) formed in excess under hypoxic conditions cause protein, DNA, and lipid oxidation. Nitric oxide (NO) formed by NO synthase (NOS) is known to be protective in ischemic stroke, however NOS has been shown to 'uncouple' under oxidative conditions to instead produce superoxide. Nitrones are antioxidant molecules that trap ROS to then decompose and release NO. Synthetic nitrones and NOS inhibitors have thus far failed to yield favorable clinical outcomes in diseases mediated by oxidative pathologies. There is currently no FDA-approved neuroprotective agent for the treatment of stroke. Therefore, there is a need in the art for new and effective treatments for ischemic stroke.

SUMMARY

Provided is a compound comprising Formula I:

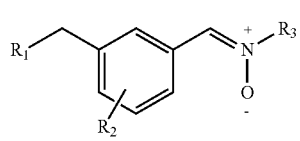

Formula I where $R_1$ is substituted or unsubstituted amino, amidinyl, guanidinyl, protonated amidinyl, protonated guanidinyl, protonated amidinyl sulfide, aminoguanidinyl, thiophenyl, ethyl amidinyl, or pyridinyl, wherein $R_1$ may form a ring with $R_2$; $R_2$ is H or a bridging group that forms the ring with $R_1$; $R_3$ is a stable radical that permits NO to be given off as a radical when the compound interacts with reactive oxygen species. Also provided are salts, stereoisomers, racemates, solvates, hydrates, prodrugs, and polymorphs of Formula I.

In certain embodiments, $R_3$ is substituted or unsubstituted alkyl, aryl, heteroaryl, aryloxy, alkoxy, or heterobicyclicyl. In particular embodiments, $R_3$ is substituted with one or more of hydroxyl, methyl, isobutyl, carboxylate, or combinations thereof. In certain embodiments, $R_3$ is tert-butyl, 2,6-di-tert-butylphenolyl, 3,5-di-hydroxybenzoate, 1,3-di-tert-butyl-4,5-dimethyl-imidazolyl, or 1-hydroxy-2,3,6-trimethylbenzo-2-methyloxanyl.

In certain embodiments, $R_1$ comprises amidinium, nitroguanidinium, thiopheneamidinium, methyl amidinium sulfide, 2-amino-4-methylpyridinyl, or amino.

In certain embodiments, the ring formed by $R_1$ and $R_2$ is a pyrazole ring, an imidazole ring, a pyrrole ring, a pyrrolidine ring, a pyrimidine ring, a pyridine ring, or a piperidine ring.

In certain embodiments, the compound comprises Formula II:

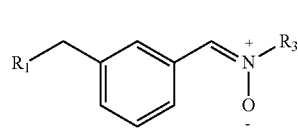

Formula II

In certain embodiments, the compound comprises Formula III:

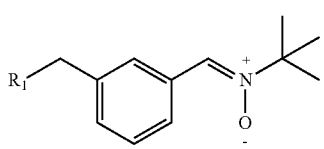

Formula III

In certain embodiments, $R_3$ is H, and $R_1$ and $R_2$ form a pyrazole ring.

In certain embodiments, $R_1$ comprises aminopyridine. In certain embodiments, $R_1$ comprises 2-amino-4-methylpyridine. In certain embodiments, $R_1$ is 2-amino-4-methylpyridine, and $R_2$ is H. In certain embodiments, $R_1$ comprises amidinyl. In certain embodiments, $R_1$ comprises thiophenylamidinyl.

In certain embodiments, the bridging group comprises an amino group.

In certain embodiments, the compound comprises compound 5:

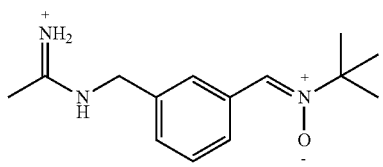

(5)

In certain embodiments, the compound comprises compound 7:

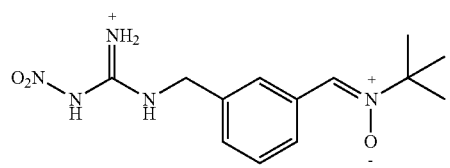

(7)

In certain embodiments, the compound comprises compound 8:

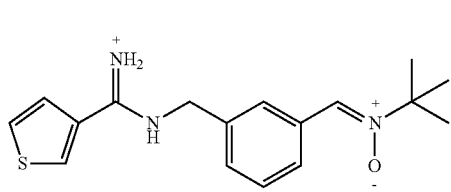
(8)

In certain embodiments, the compound comprises compound 9:

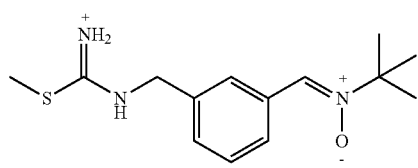
(9)

In certain embodiments, the compound comprises compound 10:

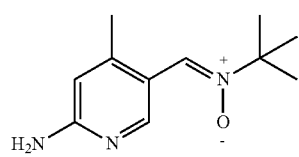
(10)

In certain embodiments, the compound comprises compound 11:

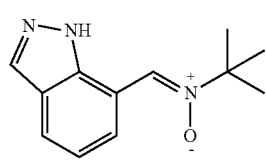
(11)

In certain embodiments, the compound comprises compound 12:

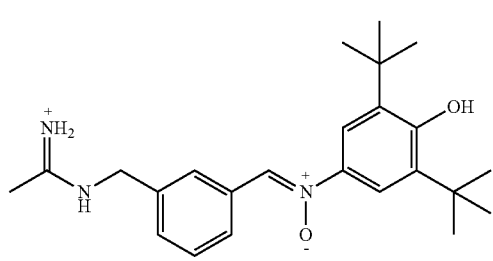
(12)

In certain embodiments, the compound comprises compound 13:

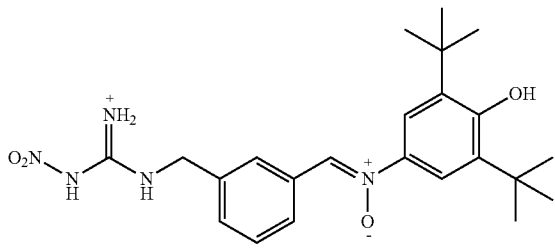
(13)

In certain embodiments, the compound comprises compound 14:

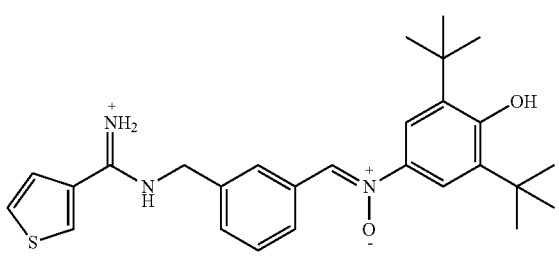
(14)

In certain embodiments, the compound comprises compound 15:

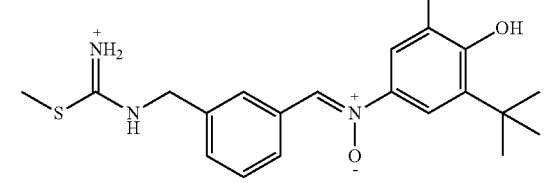
(15)

In certain embodiments, the compound comprises compound 16:

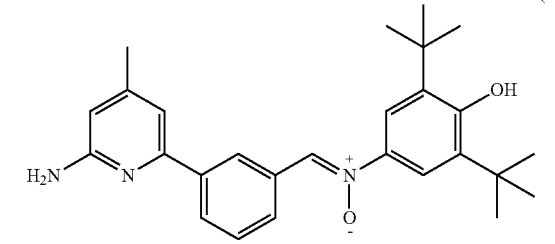
(16)

In certain embodiments, the compound comprises compound 17:

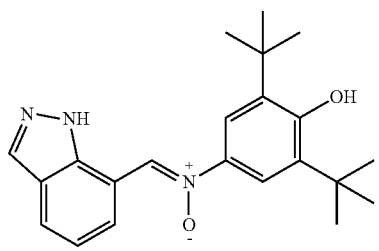

(17)

In certain embodiments, the compound comprises compound 18:

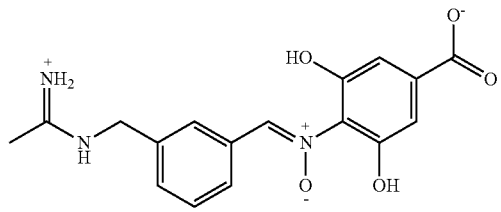

(18)

In certain embodiments, the compound comprises compound 19:

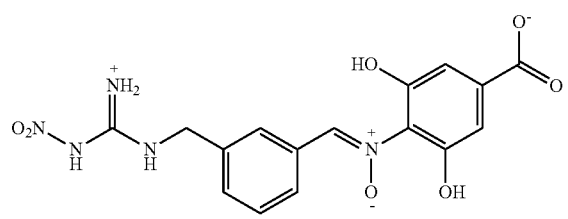

(19)

In certain embodiments, the compound comprises compound 20:

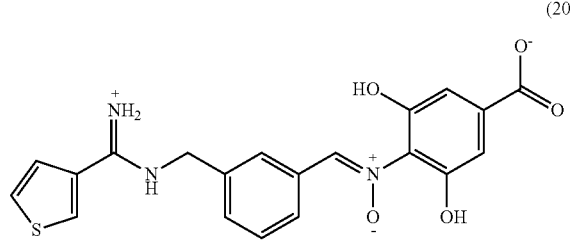

(20)

In certain embodiments, the compound comprises compound 21:

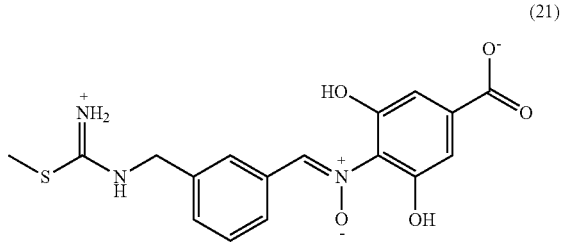

(21)

In certain embodiments, the compound comprises compound 22:

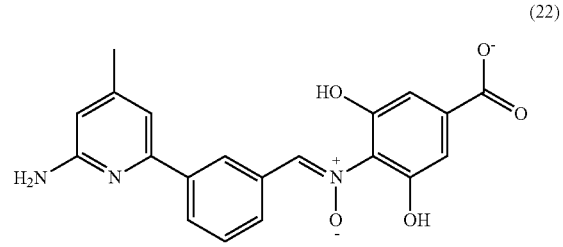

(22)

In certain embodiments, the compound comprises compound 23:

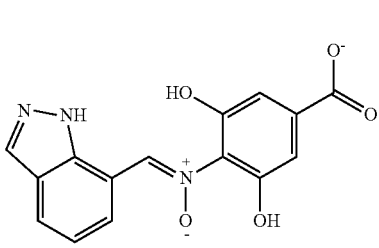

(23)

In certain embodiments, the compound comprises compound 24:

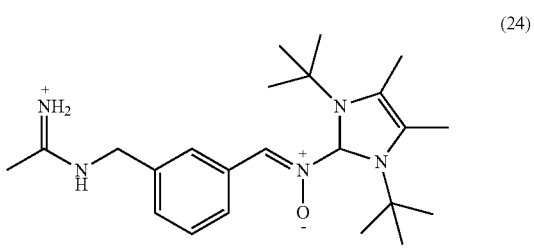

(24)

In certain embodiments, the compound comprises compound 25:

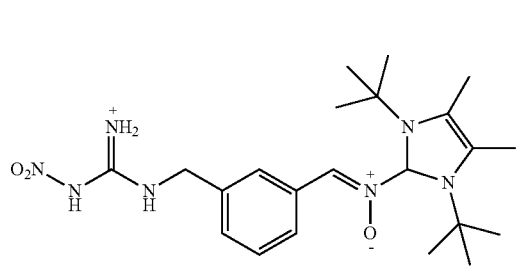
(25)

In certain embodiments, the compound comprises compound 26:

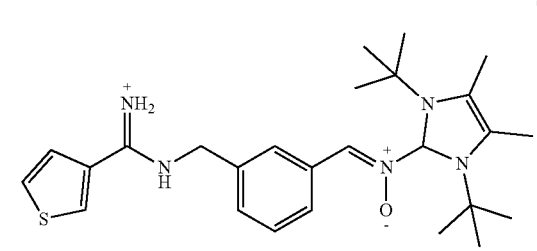
(26)

In certain embodiments, the compound comprises compound 27:

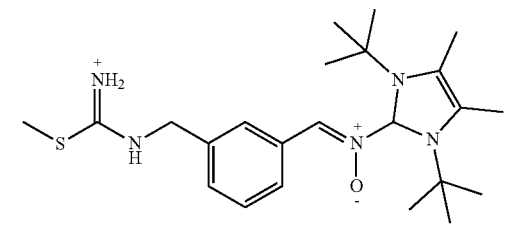
(27)

In certain embodiments, the compound comprises compound 28:

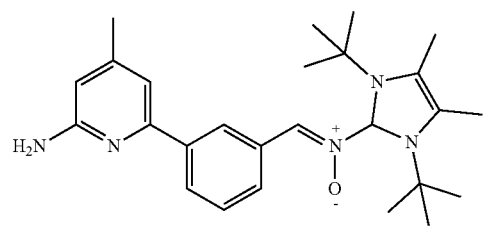
(28)

In certain embodiments, the compound comprises compound 29:

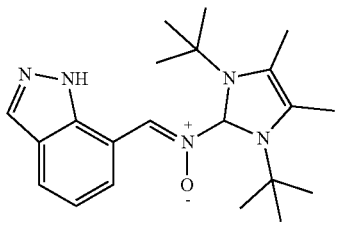
(29)

In certain embodiments, the compound comprises compound 30:

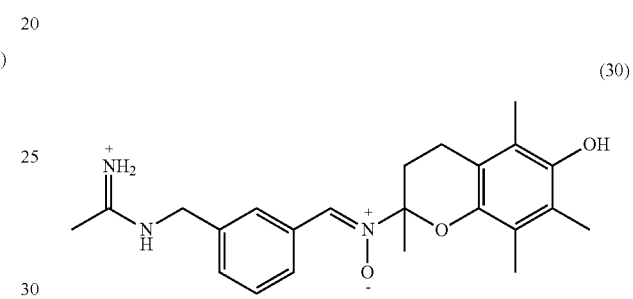
(30)

In certain embodiments, the compound comprises compound 31:

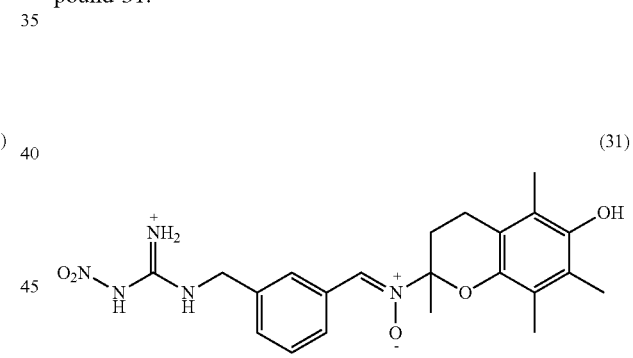
(31)

In certain embodiments, the compound comprises compound 32:

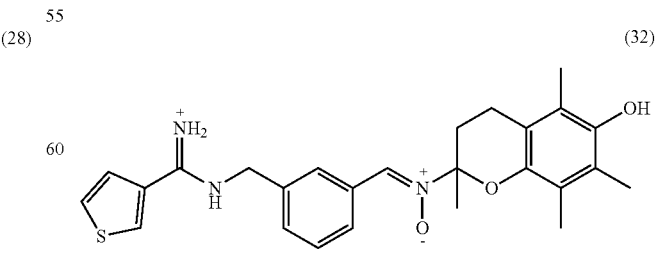
(32)

In certain embodiments, the compound comprises compound 33:

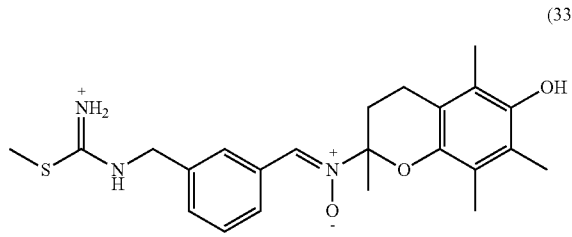
(33)

In certain embodiments, the compound comprises compound 34:

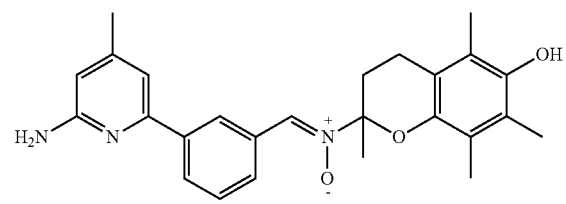
(34)

In certain embodiments, the compound comprises compound 35:

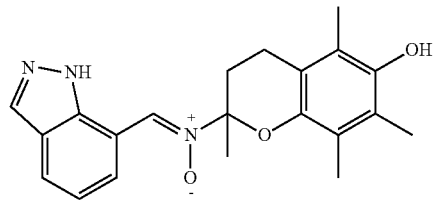
(35)

Further provided is a pharmaceutical composition comprising an effective amount of a compound of Formula I, and a pharmaceutically acceptable diluent, carrier, or adjuvant.

Further provided is a compound which reacts with reactive oxygen species (ROS) to produce a compound of Formula V:

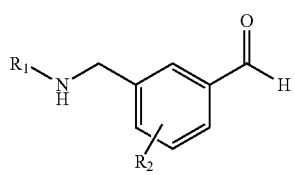
Formula V where $R_1$ is amino, aminyl, amidinyl, nitroamidinyl, protonated aminyl, protonated amidinyl, protonated aminyl sulfide, thiopheneaminyl, ethyl aminyl, a heteroatom ring formed with the adjacent N, or a group that binds to $R_2$ to form a ring; and $R_2$ is H or a bridging group that binds to $R_1$ to form the ring.

Further provided is a method of treating an ischemic stroke, the method comprising administering to a subject in need thereof an effective amount of a compound which reacts with reactive oxygen species (ROS) to produce a nitric oxide synthase (NOS) inhibitor to treat an ischemic stroke in the subject. In certain embodiments, the compound comprises Formula I:

Formula I where $R_1$ is substituted or unsubstituted amino, amidinyl, guanidinyl, protonated amidinyl, protonated guanidinyl, protonated amidinyl sulfide, aminoguanidinyl, thiophenyl, ethyl amidinyl, or pyridinyl, wherein $R_1$ may form a ring with $R_2$; $R_2$ is H or a bridging group that forms the ring with $R_1$; $R_3$ is a stable radical that permits NO to be given off as a radical when the compound interacts with reactive oxygen species; or a salt, stereoisomer, racemate, solvate, hydrate, prodrug, or polymorph thereof.

In certain embodiments, the compound comprises Formula II:

Formula II

In certain embodiments, the compound comprises Formula III:

Formula III

In certain embodiments, the compound comprises compound 5:

(5)

In certain embodiments, the compound comprises one of compounds 7-35:
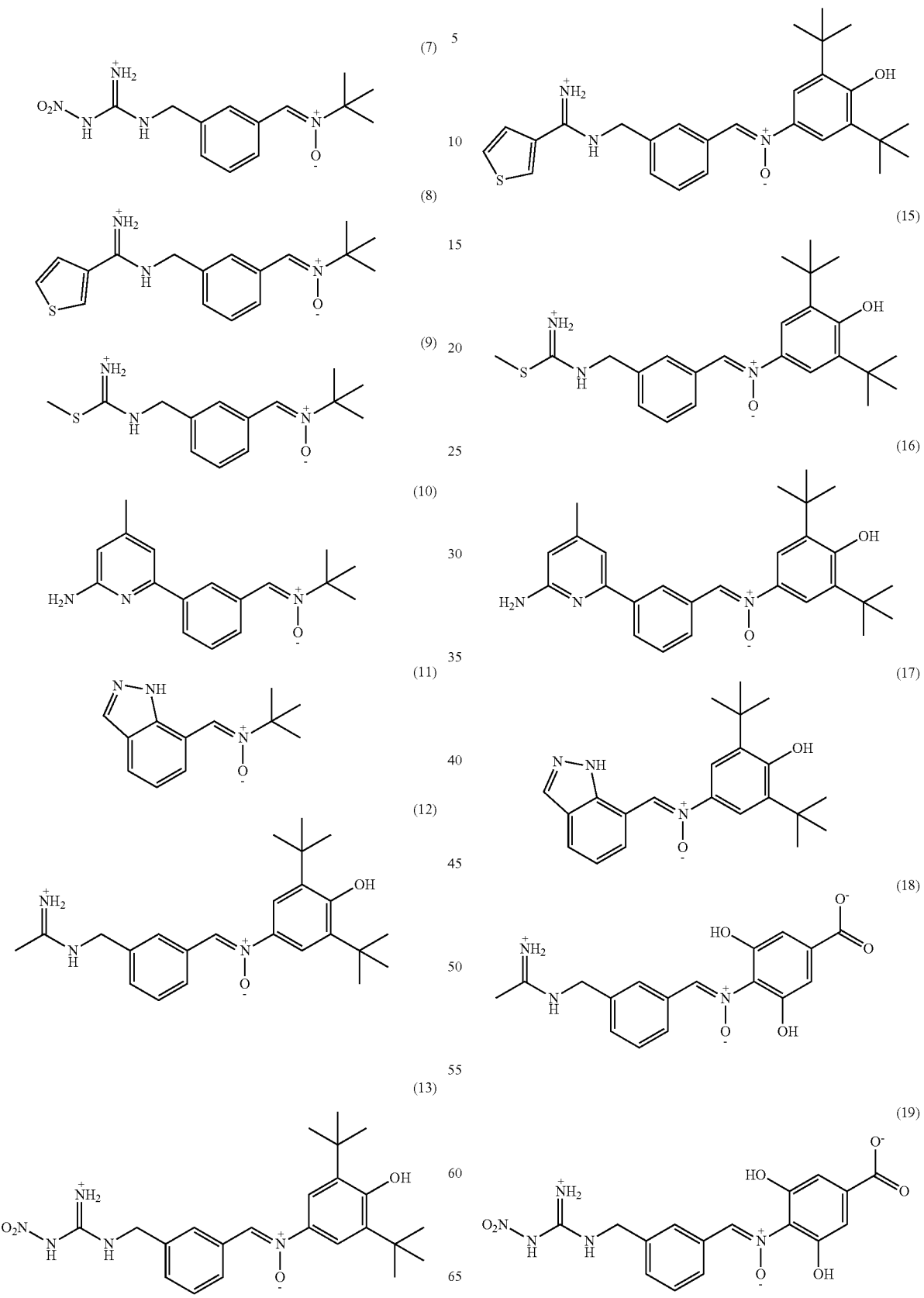

(20)
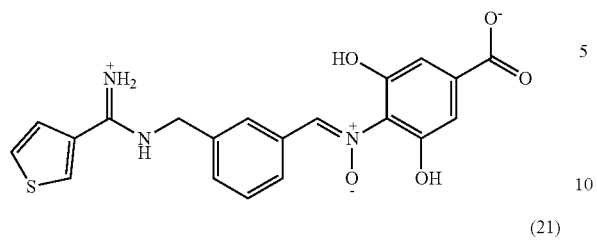
(21)
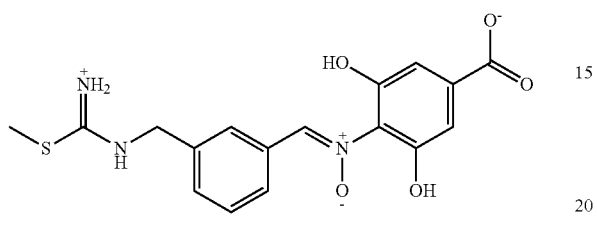
(22)
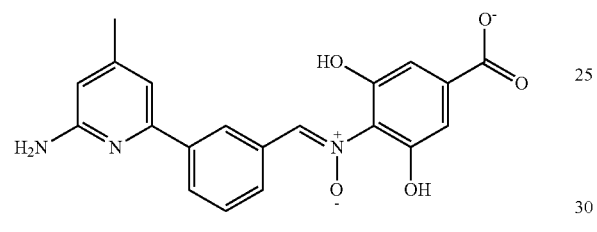
(23)
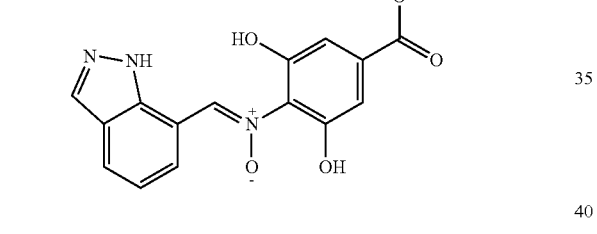
(24)
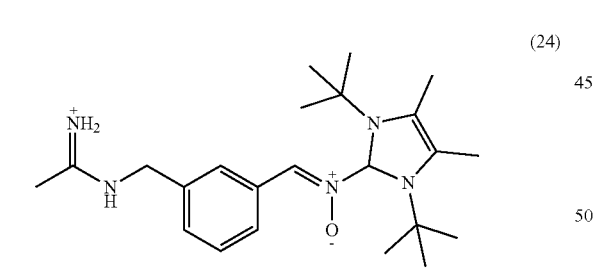
(25)
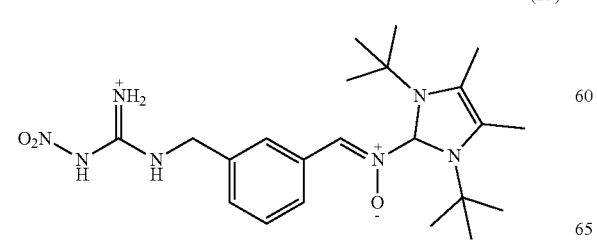
(26)
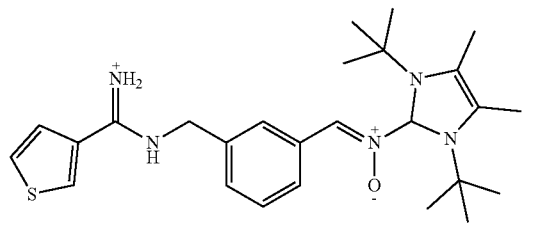
(27)
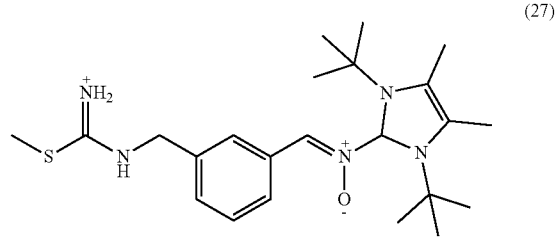
(28)
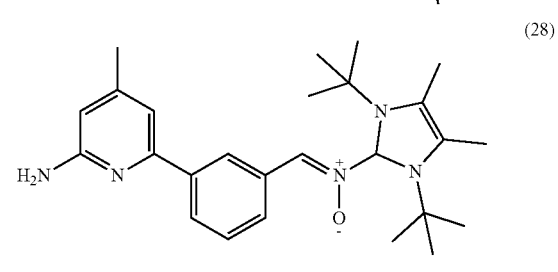
(29)
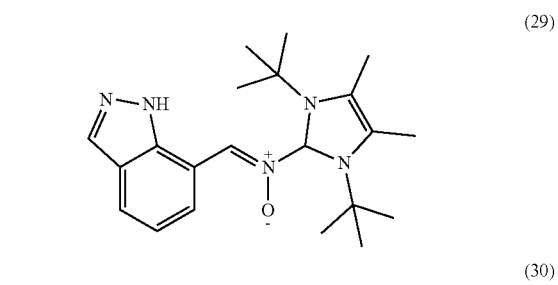
(30)
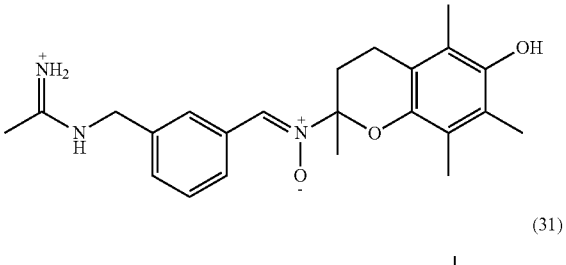
(31)
(32)
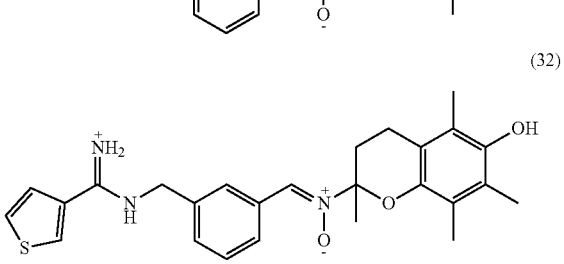

(33)

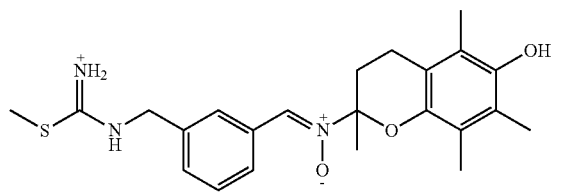

(34)

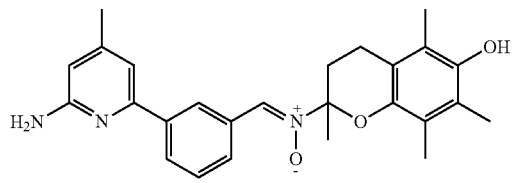

(35)

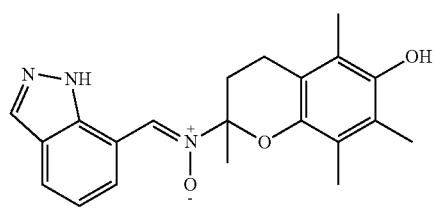

Further provided is a method of making a prodrug, the method comprising reacting a substituted benzaldehyde with a reactant in the presence of microwaves to produce a prodrug, wherein the reactant comprises one of an N-alkyl hydroxylamine, N-aryl hydroxylamine, N-heteroaryl hydroxylamine, N-aryloxy hydroxylamine, N-alkoxy hydroxylamine, or N-heterobicyclicyl hydroxylamine.

Further provided is a kit for making a prodrug, the kit comprising a first container housing a benzaldehyde; and a second container housing at least one of an N-alkyl hydroxylamine, N-aryl hydroxylamine, N-heteroaryl hydroxylamine, N-aryloxy hydroxylamine, N-alkoxy hydroxylamine, or N-heterobicyclicyl hydroxylamine.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

PRIOR ART FIG. 1B: Structures of known linear nitrones and NOS-inhibitors.

FIGS. 4B-4F show optimized structures, including bond lengths, and charge and spin densities (in parenthesis) for 5, its free radical adducts, and calculated $\Delta G_{rxn}$, formed from $O_2^-/HO_2$, .OH, and HOONO (triplet products) at the PCM/B3LYP/6-$_{31}$+G(d,p)// B3LYP/6-$_{31}$G(d) level of theory. FIGS. 4G-4H show the most energetically favored binding structures of 5 (FIG. 4G) and 6 (FIG. 4H) with nNOS (PDB: 1QWC) calculated by Swissdock.ch and visualized by UCSF Chimera.

FIGS. 5A-5E: Thermodynamic parameters of ROS-PBN and 5 adducts at the PCM/B3LYP/6-31+g**//B3LYP/6-31g* level of theory (ZPE scaling factor=0.9806 and hartree to kcal/mol=627.5095), shown in Parts I-V.

FIGS. 6A-6D: Docking parameters of 5, 6, L-arginine, and 1400W with NOS isozymes (crystal structure in parenthesis) using Swissdock.ch and UCSF Chimera, shown in Parts I-IV.

FIGS. 11D-11F show HPLC-PDA analysis of 5 in corresponding radical-generating systems at 289 nm (solid line) and 254 nm (dotted line) taken after 24 hr incubation at 37° C. The $O_2.^-/HO_2$. and .OH systems (FIGS. 11D, 11E) show substantial formation of 6, and the ONOO$^-$ system (FIG. 11F) shows complete conversion.

(FIG. 15A.) Griess assay of LPS-stimulated SIM-A9 cells following 24 hr treatment indicates anti-inflammatory ability for 5 similar to that of PBN and 1400W (n=3). (FIG. 15B.) FIGS. 15C-15F show Western blot analysis of SH-SY5Y cells exposed to OGD and 24 hr treatment. 5 treatment (1.0 µM) was found to increase pAkt/Akt ratio (n=6) (FIG. 15C), and decrease total 3-NT (FIG. 15D), cleaved-caspase 3 (FIG. 15E), and pERK1/2 (FIG. 15F) compared to vehicle control (n=3). Data represented as mean±SEM, *p<0.05, p<0.01, and *p<0.001, from respective vehicle controls, One-way ANOVA followed by Newman-Keuls post-hoc test.

(FIG. 17A.) The lower dose of 5 (1 mg/kg) elevated CBF, whereas a higher dose of 5 (10 mg/kg) showed no change in CBF from base-line (n=3, One-way ANOVA followed by Newman-Keuls post-hoc test). FIGS. 17B-17D show neurobehavioral performance of mice treated with vehicle (n=10) or 5 (n=12) after pMCAO. No significant differences were observed for rota rod performance (FIG. 17C), but treatment with 5 improved grip strength (FIG. 17D, Two-way ANOVA followed by Bonferroni multiple comparisons test), and reduced neurological deficit scoring (FIG. 17B, unpaired t-test). FIGS. 17E-17F show infarct volume analysis of vehicle (top in FIG. 17F) vs 5-treated (bottom in FIG. 17F) mouse brains 72 hr after pMCAO by TTC staining (unpaired t-test). Data represented as mean±SEM, *p<0.05, p<0.01, *p<0.001 from vehicle or baseline.

DETAILED DESCRIPTION

Figure 1A:
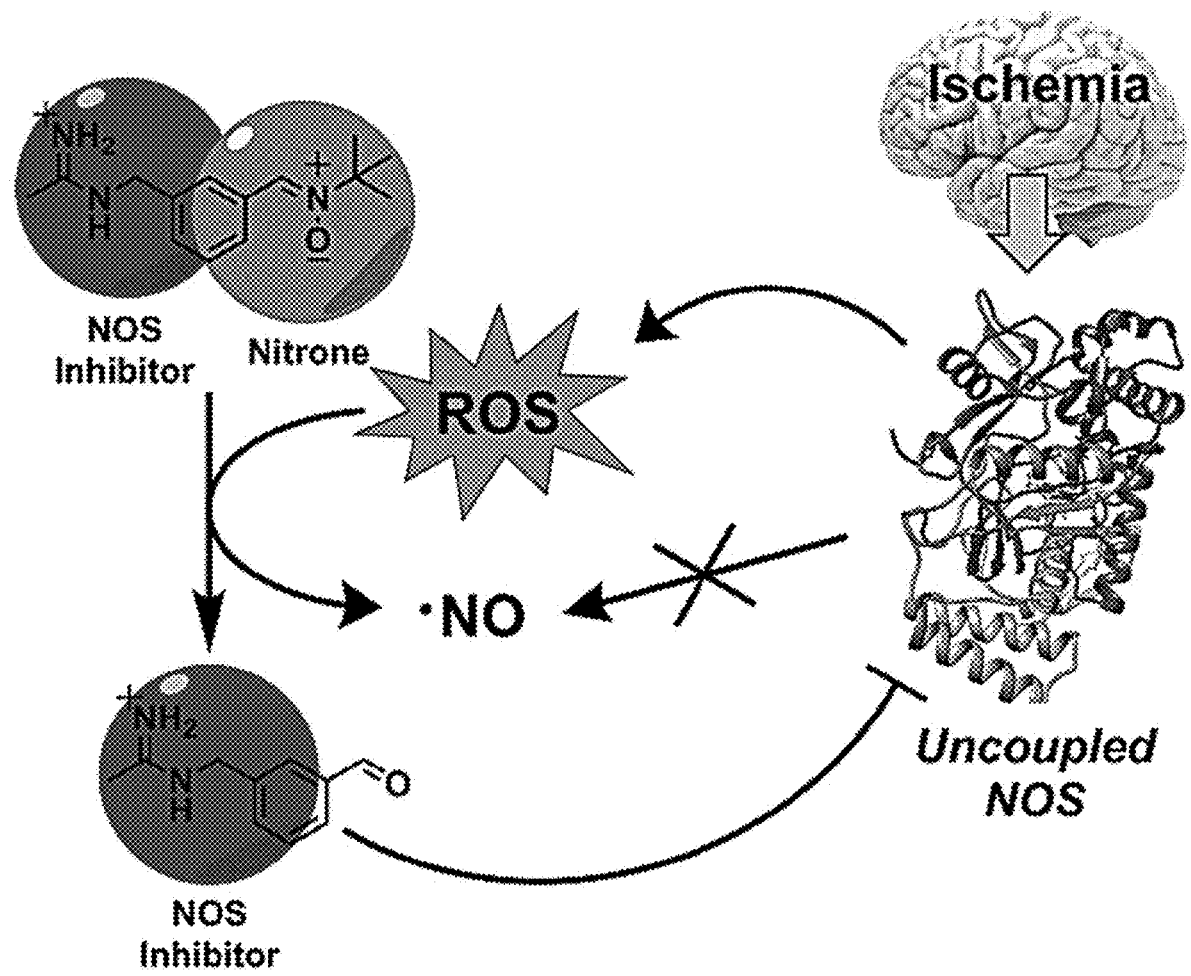
FIG. 1A: Diagram of mechanism of action of nitrone pro-drugs for the treatment of ischemic stroke.

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

Definitions

For convenience, certain terms are defined, and certain concepts are established, prior to further description of the present disclosure.

Unless stereochemistry is specifically indicated, all stereoisomers of the compounds herein are included, as pure compounds as well as mixtures thereof. It will be appreciated by one of ordinary skill in the art that asymmetric centers may exist in any of the compounds disclosed herein. Thus, the compounds and compositions thereof may be in the form of an individual enantiomer, diastereomer, or geometric isomer, or may be in the form of a mixture of stereoisomers. In certain embodiments, the compounds herein are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures herein encompass those structures in which double bonds are (Z) or (E).

The term "composition" as used herein is intended to encompass a product comprising the specified ingredients in the specified amounts, as well as any product that results, directly or indirectly, from combinations of the specified ingredients in the specified amounts.

The term "solvate" refers to a pharmaceutically acceptable solid form of a specified compound containing solvent molecules as part of the crystal structure. A solvate typically retains at least some of the biological effectiveness of such compound. Solvates can have different solubilities, hygroscopicities, stabilities, and other properties. Examples of solvates include, but are not limited to, compounds in combination with water, isopropanol, ethanol, methanol, DMSO, ethyl acetate, acetic acid, or ethanolamine. Solvates are sometimes termed "pseudopolymorphs."

The term "hydrate" refers to a solvate with water.

The term "racemate" refers to a mixture that contains an equal amount of enantiomers.

The term "polymorph" means a crystalline form of a substance that is distinct from another crystalline form of the substance but that shares the same chemical formula.

It will be appreciated that any of the compounds described herein may be substituted with any number of substituents or functional moieties. In general, the term "substituted," whether preceded by the term "optionally" or not, and substituents contained in formulas, refer to the replacement of hydrogen atoms in a given structure with a specified substituent. When more than one position in any given structure may be substituted with more than one substituent selected from a specified group, the substituent may be either the same or different at every position. The term "substituted" is contemplated to include all permissible substituents of organic compounds. In a broad aspect, the permissible substituents include acyclic and cyclic, branched and unbranched, carbocyclic and heterocyclic, aromatic and nonaromatic substituents or organic compounds. For purposes of explanation herein, heteroatoms such as nitrogen may have hydrogen substituents and/or any permissible substituents of organic compounds described herein which satisfy the valencies of the heteroatoms. Furthermore, there is not any intention to be limited in any manner by the permissible substituents of organic compounds. Combinations of substituents and variables envisioned are, in some embodiments, those that result in the formation of stable compounds useful in the treatment, for example, of cancers.

The term "pharmaceutically acceptable carrier" means a medium that is used to prepare a desired dosage form of a compound. A pharmaceutically acceptable carrier includes solvents, diluents, or other liquid vehicles; dispersion or suspension aids; surface active agents; isotonic agents; thickening or emulsifying agents; preservatives; solid binders; lubricants; and the like.

The term "pharmaceutically acceptable salts," as used herein, refers to salts of compounds of the present disclosure that are substantially non-toxic to living organisms. Typical pharmaceutically acceptable salts include those salts prepared by reaction of a compound of the present disclosure with an inorganic or organic acid, or an organic base, depending on the substituents present on the compounds.

Examples of inorganic acids which may be used to prepare pharmaceutically acceptable salts include: hydrochloric acid, phosphoric acid, sulfuric acid, hydrobromic acid, hydroiodic acid, phosphorous acid, and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids, and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like. Suitable pharmaceutically acceptable salts may also be formed by reacting the compounds of the present disclosure with an organic base such as methylamine, ethylamine, ethanolamine, lysine, ornithine, and the like. Other suitable salts are known to one of ordinary skill in the art.

The term "alkyl" refers to monovalent hydrocarbon groups having from 1 to 50 carbon atoms, such as from 1 to 10 carbon atoms, or such as from 1 to 6 carbon atoms. This term is exemplified by groups such as methyl, ethyl, n-propyl, iso-propyl, n-butyl, iso-butyl, n-hexyl, and the like. "Substituted alkyl" refers to an alkyl group, preferably of from 1 to 10 carbon atoms, having from 1 to 3 substituents selected from the group consisting of alkoxy, substituted alkoxy, acyl, acylamino, amino, aminoacyl, aminocarboxy esters, cyano, cycloalkyl, halogen, hydroxyl, carboxyl, carboxylalkyl, oxyacyl, oxyacylamino, thiol, thioalkoxy, substituted thioalkoxy, aryl, heteroaryl, heterocyclic, aryloxy, thioaryloxy, heteroaryloxy, thioheteroaryloxy, nitro, and mono- and di-alkylamino, mono- and di-(substituted alkyl) amino, mono- and di-arylamino, mono- and di-heteroarylamino, mono- and di-heterocyclic amino, and unsymmetric di-substituted amines having different substituents selected from alkyl, substituted alkyl, aryl, heteroaryl, and heterocyclic.

The term "aryl" refers to an unsaturated aromatic carbocyclic group, for example of from 6 to 14 carbon atoms, having a single ring (e.g., phenyl) or multiple condensed rings (e.g., naphthyl or anthryl), preferably having from 1 to 3 rings. Some example aryls include phenyl, naphthyl, and the like. Unless otherwise constrained by the definition for the aryl substituent, such aryl groups can optionally be substituted with from 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, aminoacyl, aminocarboxy esters, alkaryl, aryl, aryloxy, carboxyl, carboxylalkyl, acylamino, cyano, halo, nitro, heteroaryl, heterocyclic, oxyacyl, oxyacylamino, thioalkoxy, substituted thioalkoxy, trihalomethyl, mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl, heterocyclic, and the like. Some example substituents include alkyl, alkoxy, halo, cyano, nitro, trihalomethyl, and thioalkoxy.

The terms "heteroaryl" or "hetaryl" refer to a group that is both heterocyclic and aromatic.

The term "aryloxy" refers to a group or radical having an aryl group bonded to oxygen. Non-limiting examples of aryloxy groups include phenoxy and substituted phenoxy such as dimethylphenoxy, trimethylphenoxy, halo-substituted phenoxy, and the like.

The term "alkoxy" refers to a group or radical having an alkyl group bonded to oxygen. Non-limiting examples of alkoxy include methoxy, ethoxy, tert-butoxy, and the like.

The term "heterobicyclicyl" refers to a group or radical having two rings, where at least one of the rings includes a heteroatom. Non-limiting examples of heterobicyclicyl groups include indolyl, quinolinyl, chromanyl, purinyl, isoquinolinyl, pteridinyl, guaninyl, adeninyl, benzofuranyl, chromenyl, benzodithiolyl, benzimidazolyl, and the like.

GENERAL DESCRIPTION

Provided is a class of compounds which resolves the limitations of synthetic nitrones and NOS inhibitors known in the art through a pro-drug approach to the elimination and prevention of oxidative species. The compounds described herein are designed based on their respective radical adduct decomposition products. These decomposition products are NOS inhibitors that are effectively formed at the site of oxidative stress, selectively targeting dysfunctional, uncoupled NOS. (FIG. 1A.) The ability of one such compound, referred to herein as compound 5, to spin-trap radicals and decompose into the putative NOS inhibitor, has been demonstrated using EPR and LC-MS/MS. As described in the examples herein, the pro-drug approach has been tested in vitro by measuring cell viability and inhibitor formation in a cell model of ischemia and reperfusion. Compound 5 was found to be efficacious, and was able to increase pAkt while reducing nitrotyrosine and cleaved caspase-3 levels. Doppler flowmetry on anesthetized mice showed an increased cerebral blood flow upon intravenous administration of 1 mg/kg of compound 5, but a return to baseline upon administration of 10 mg/kg. Without wishing to be bound by theory, it is believed that this is likely due to its dual nature of antioxidant/NO-donor and NOS-inhibition properties. Mice treated with compound 5 after permanent middle cerebral artery occlusion (pMCAO) performed better in neurobehavioral assessments and exhibited a >30% reduction in infarct volume. Without wishing to be bound by theory, it is believed that this efficacy is due to higher formation of the NOS inhibitor decomposition product in ischemic tissue observed by LC-MS/MS, resulting in region specific effects limited to the infarct area.

In general, the pro-drug compounds herein have the following general structural formula of Formula I:

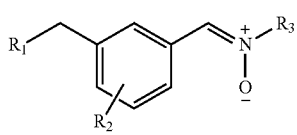

Formula I

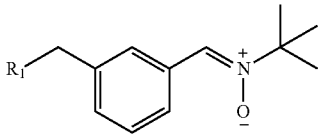

Formula III where R₁ is substituted or unsubstituted amino, amidinyl, guanidinyl, protonated amidinyl, protonated guanidinyl, protonated amidinyl sulfide, aminoguanidinyl, thiophenyl, ethyl amidinyl, or pyridinyl, wherein R₁ may form a ring with R₂; R₂ is H or a bicyclic bridging group that binds to R₁ to form a ring; and R₃ is a stable radical which allows for NO to be given off as a radical. Salts, stereoisomers, racemates, hydrates, solvates, and polymorphs of Formula I are also provided. In some non-limiting examples, R₁ is amidinium, nitroguanidinium, thiopheneamidinium, methyl amidinium sulfide, 2-amino-4-methylpyridinyl, or amino. When R₁ and R₂ are bridging groups such that R₁ and R₂ bind to form a ring, the ring may be, for example, a pyrazole ring, an imidazole ring, a pyrrole ring, a pyrrolidine ring, a pyrimidine ring, a pyridine ring, or a piperidine ring. In some embodiments, R₃ is substituted or unsubstituted alkyl, aryl, heteroaryl, aryloxy, alkoxy, or heterobicyclicyl. R₃ may be substituted with, for example, one or more hydroxyl, methyl, isobutyl, or carboxylate groups, or combinations thereof. In certain non-limiting examples, R₃ is selected from the group consisting of tert-butyl, 2,6-di-tert-butylphenolyl, 3,5-di-hydroxybenzoate, 1,3-di-tert-butyl-4,5-dimethyl-imidazolyl, and 1-hydroxy-2,3,6-trimethylbenzo-2-methyloxanyl.

Any salt of Formula I, including but not limited to those defined above as examples of suitable pharmaceutically acceptable salts, is encompassed herein.

Some compounds of Formula I have the general structural formula of Formula II:

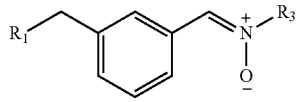

Formula II where R₁ is substituted or unsubstituted amino, amidinyl, guanidinyl, protonated amidinyl, protonated guanidinyl, protonated amidinyl sulfide, aminoguanidinyl, thiophenyl, ethyl amidinyl, or pyridinyl, and R₃ is a stable radical which allows for NO to be given off as a radical. In some embodiments, R₃ is substituted or unsubstituted alkyl, aryl, heteroaryl, aryloxy, alkoxy, or heterobicyclicyl. R₃ may be substituted with, for example, one or more hydroxyl, methyl, isobutyl, or carboxylate groups, or combinations thereof. In certain non-limiting examples, R₃ is selected from the group consisting of tert-butyl, 2,6-di-tert-butylphenolyl, 3,5-di-hydroxybenzoate, 1,3-di-tert-butyl-4,5-dimethyl-imidazolyl, and 1-hydroxy-2,3,6-trimethylbenzo-2-methyloxanyl.

Some compounds of Formula I have the general structural formula of Formula III:

where R₁ is substituted or unsubstituted amino, amidinyl, guanidinyl, protonated amidinyl, protonated guanidinyl, protonated amidinyl sulfide, aminoguanidinyl, thiophenyl, ethyl amidinyl, or pyridinyl.

Some compounds of Formula I have the general structural formula of Formula IV:

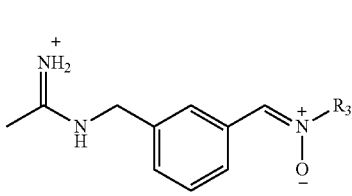

Formula IV where R₃ is a stable radical which allows for NO to be given off as a radical. In some embodiments, R₃ is substituted or unsubstituted alkyl, aryl, heteroaryl, aryloxy, alkoxy, or heterobicyclicyl. R₃ may be substituted with, for example, one or more hydroxyl, methyl, isobutyl, or carboxylate groups, or combinations thereof. In certain non-limiting examples, R₃ is selected from the group consisting of tert-butyl, 2,6-di-tert-butylphenolyl, 3,5-di-hydroxybenzoate, 1,3-di-tert-butyl-4,5-dimethyl-imidazolyl, and 1-hydroxy-2,3,6-trimethylbenzo-2-methyloxanyl.

One non-limiting example of a compound of Formula I is compound 5, which has the following structural formula:

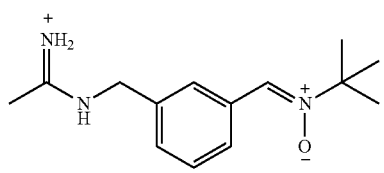

(5)

Figure 2:
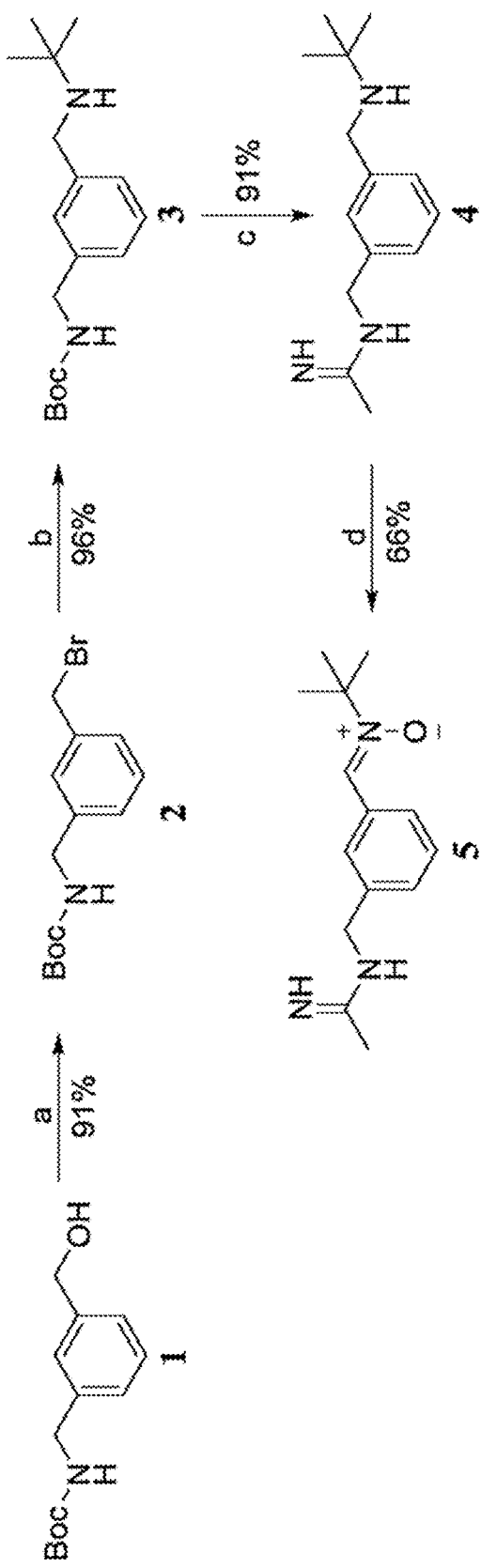
FIG. 2: Scheme 1, depicting the synthesis of compound 5 and intermediates. [a](a) $CBr_4$, $PPh_3$, $CH_2Cl_2$, 0° C.→rt 30 hr; (b) tert-butylamine, $K_2CO_3$, DMF, 3 hr; (c) (i) TFA, $CH_2Cl_2$, 0° C., 2 hr; (ii) ethyl acetimidate, EtOH, rt, 12 hr; (d) $H_2O_2$, $Na_2WO_4(H_2O)_2$, MeOH, 0° C.→rt, 12 hr.

Compound 5 can be synthesized by an efficient route, depicted in FIG. 2, though other routes of synthesizing compound 5 are possible and entirely encompassed within the present disclosure. The examples herein show evidence of ROS-induced formation of the respective NOS inhibitor, as well as stroke site-specific formation of the NOS inhibitor in vivo.

Figure 3A:
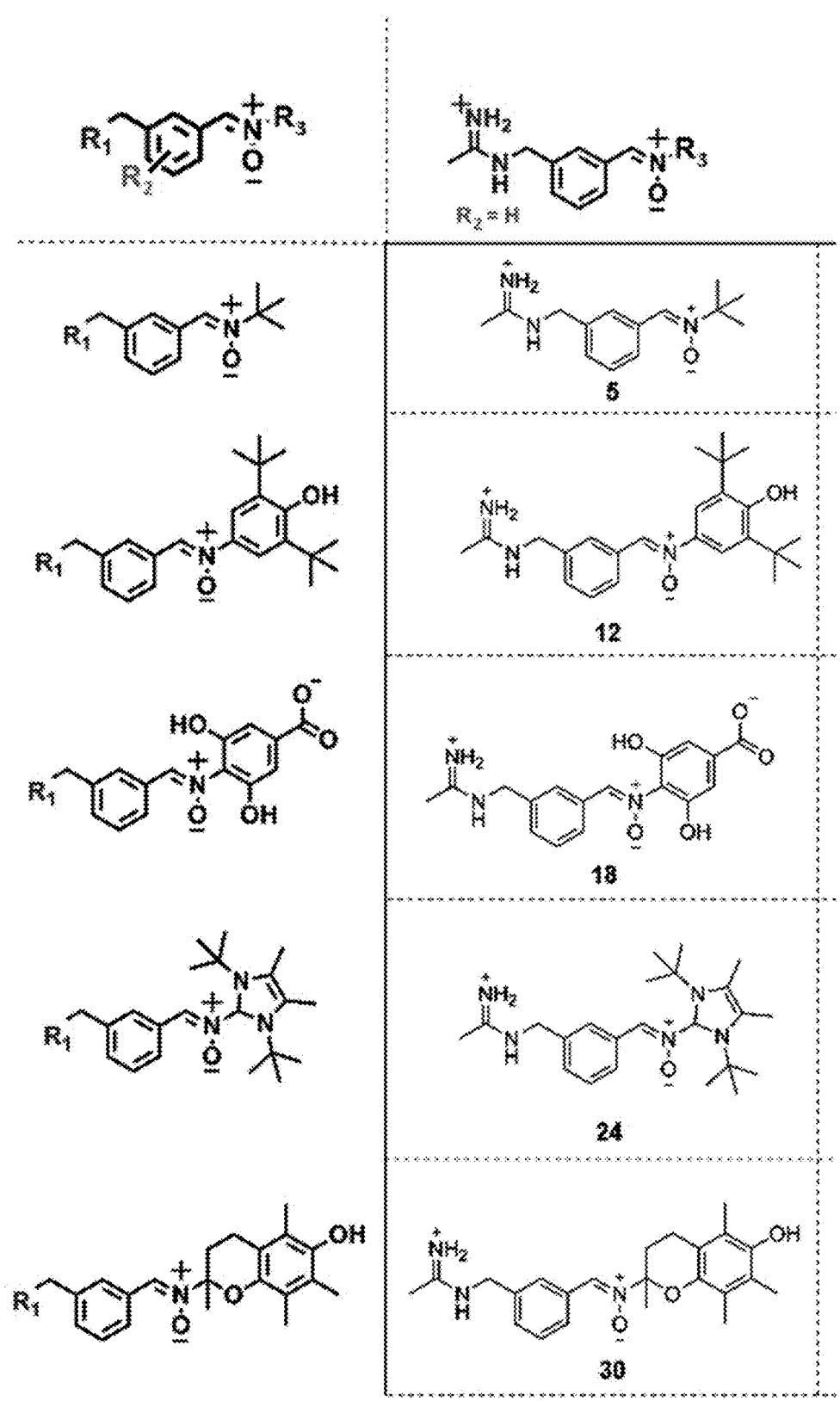
FIGS. 3A-3B: Non-limiting example compounds of Formula I (FIG. 3A) and non-limiting example synthetic route to produce compounds of Formula I through a one-step microwave process (FIG. 3B). The functional groups $R_1$, $R_2$, and $R_3$ are color coded in FIGS. 3A-3B for ease of illustration.
Figure 3A:
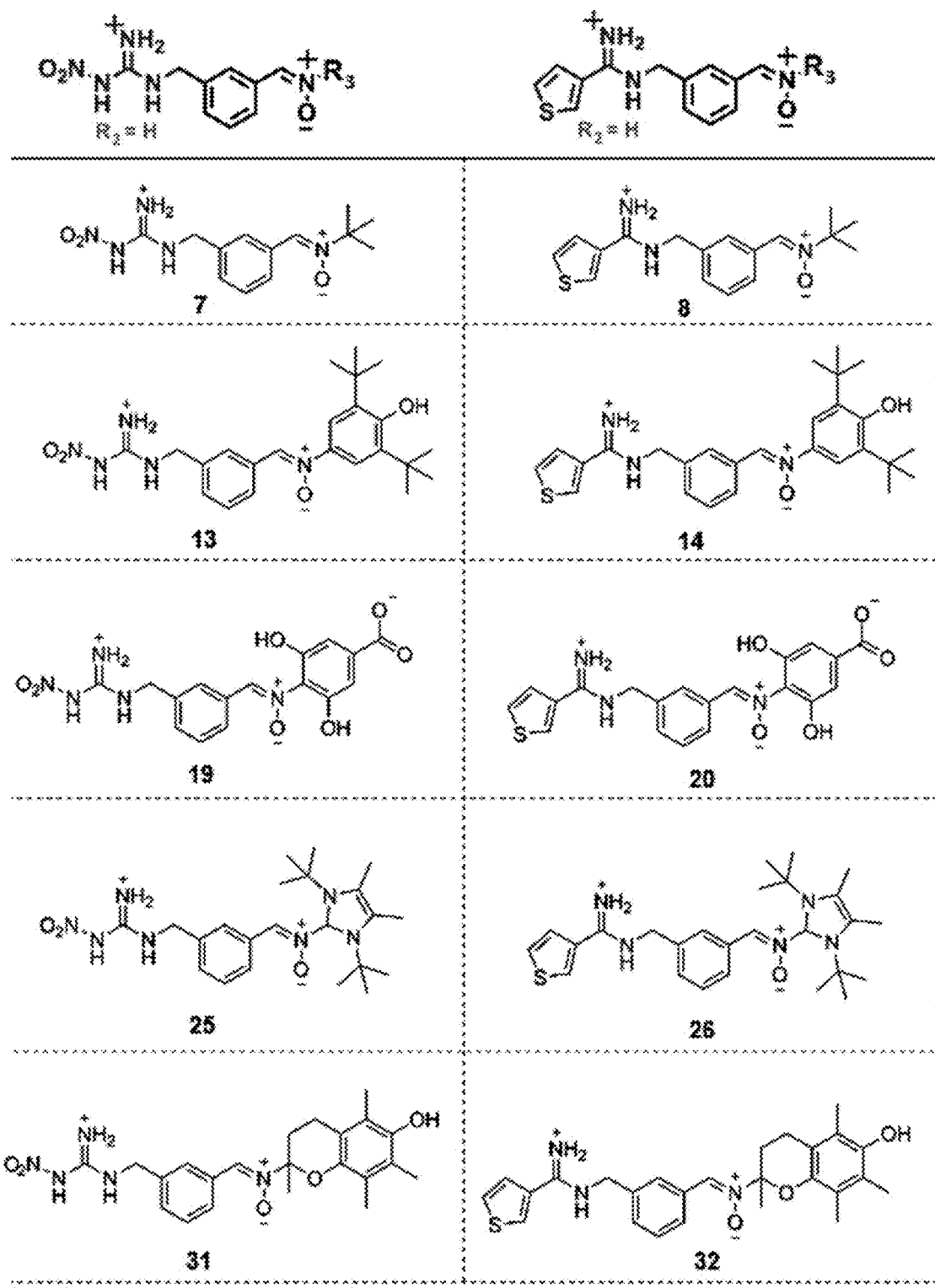
Figure 3A:
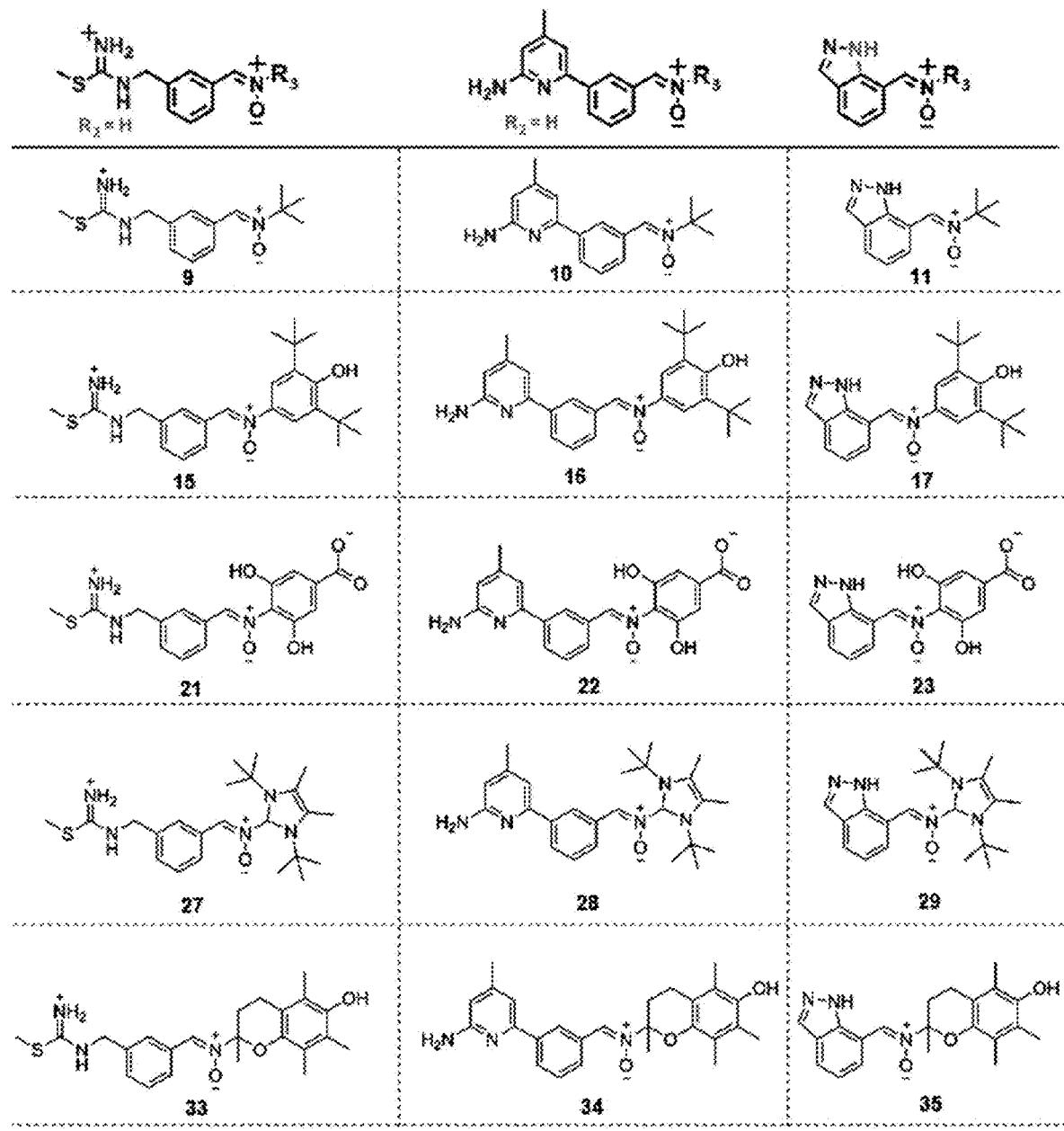
Figure 3B:
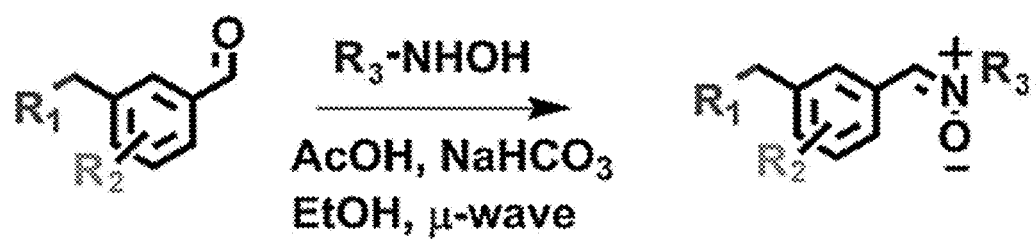

FIG. 3A shows a variety of other non-limiting example compounds of Formula I (i.e., in addition to compound 5), namely compounds 7-35. FIG. 3B shows a non-limiting example synthetic route to prepare such compounds. As shown in FIG. 3B, the compounds of Formula I can be obtained in one step through a microwave synthesis from a substituted benzaldehyde starting material. The substituted benzaldehyde is reacted with a reactant in the presence of microwaves, where the reactant is an N-alkyl hydroxylamine, N-aryl hydroxylamine, N-heteroaryl hydroxylamine, N-aryloxy hydroxylamine, N-alkoxy hydroxylamine, or N-heterobicyclicyl hydroxylamine.

Figure 4A:
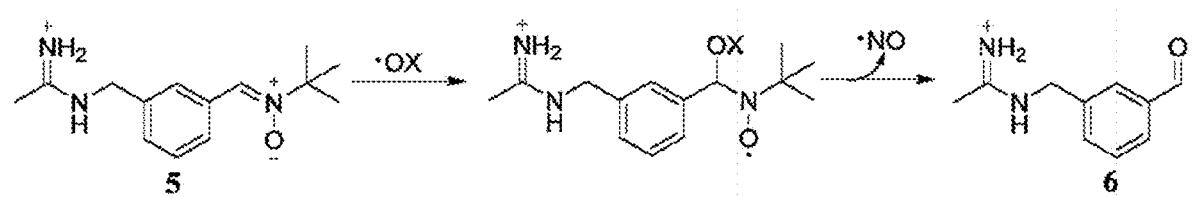
FIGS. 4A-4H: General scheme for the formation of compound 6 after the reaction of compound 5 with oxygen-centered free radicals (—OX) (FIG. 4A).
Figure 4B:
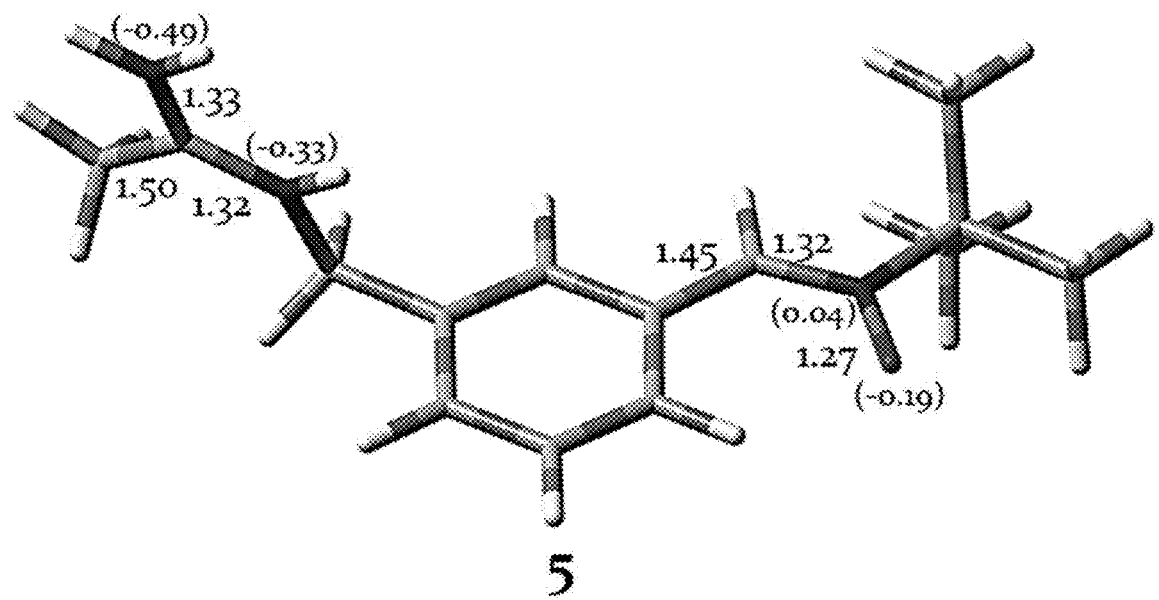
Figure 4C:
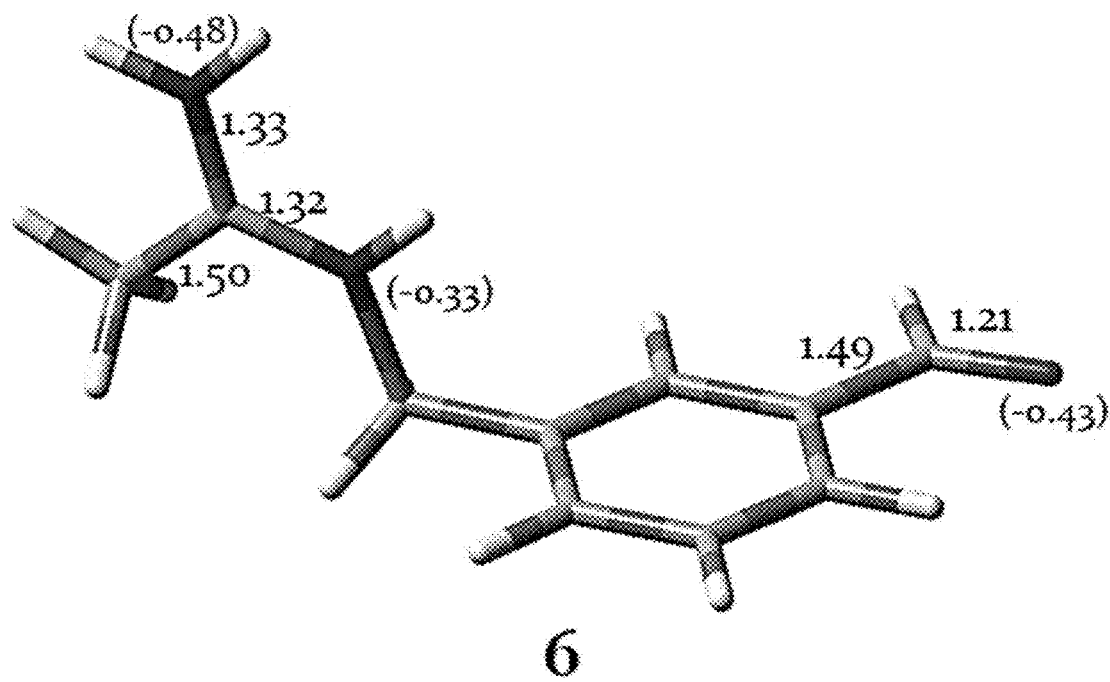
Figure 4D:
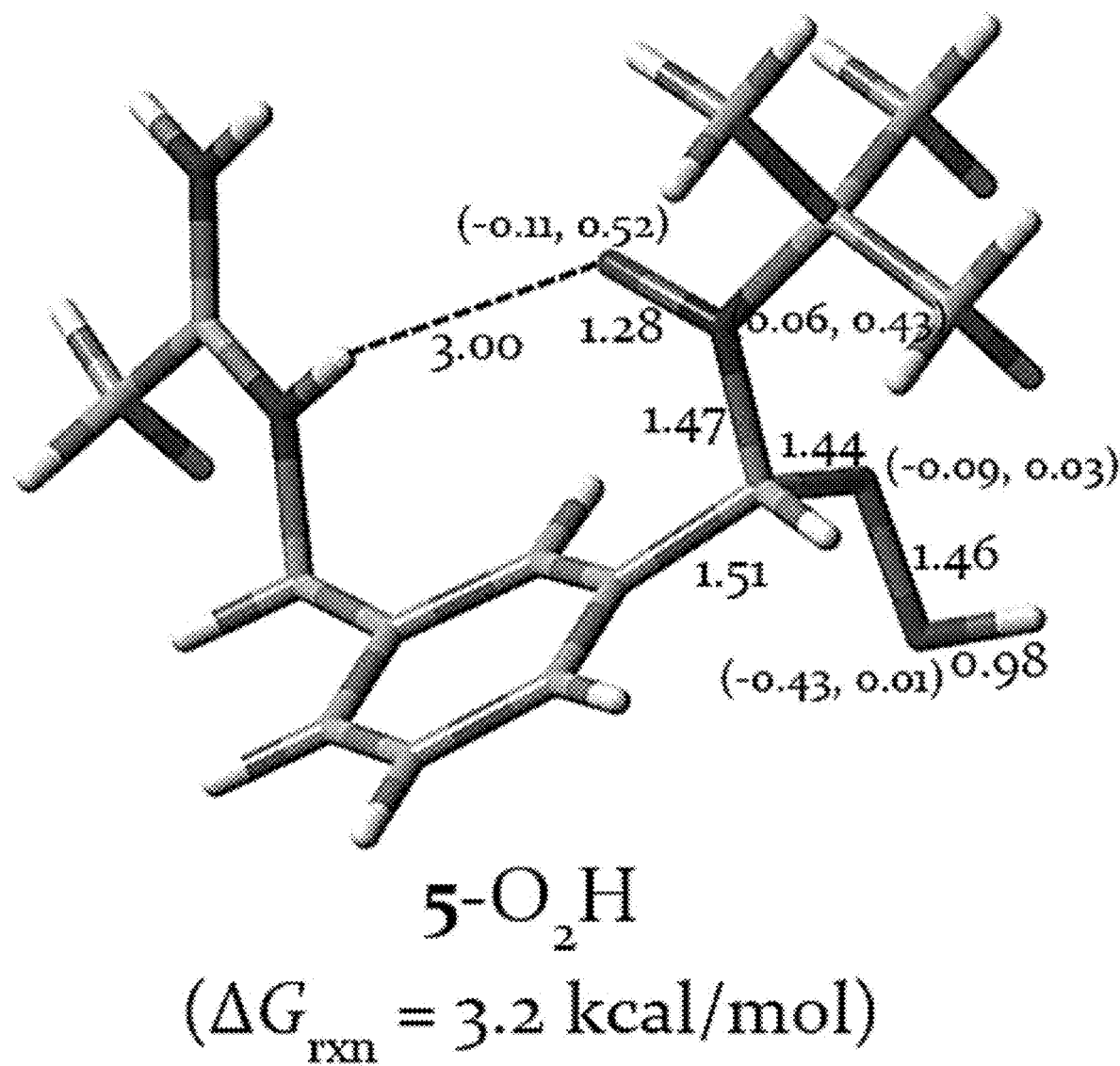
Figure 4E:
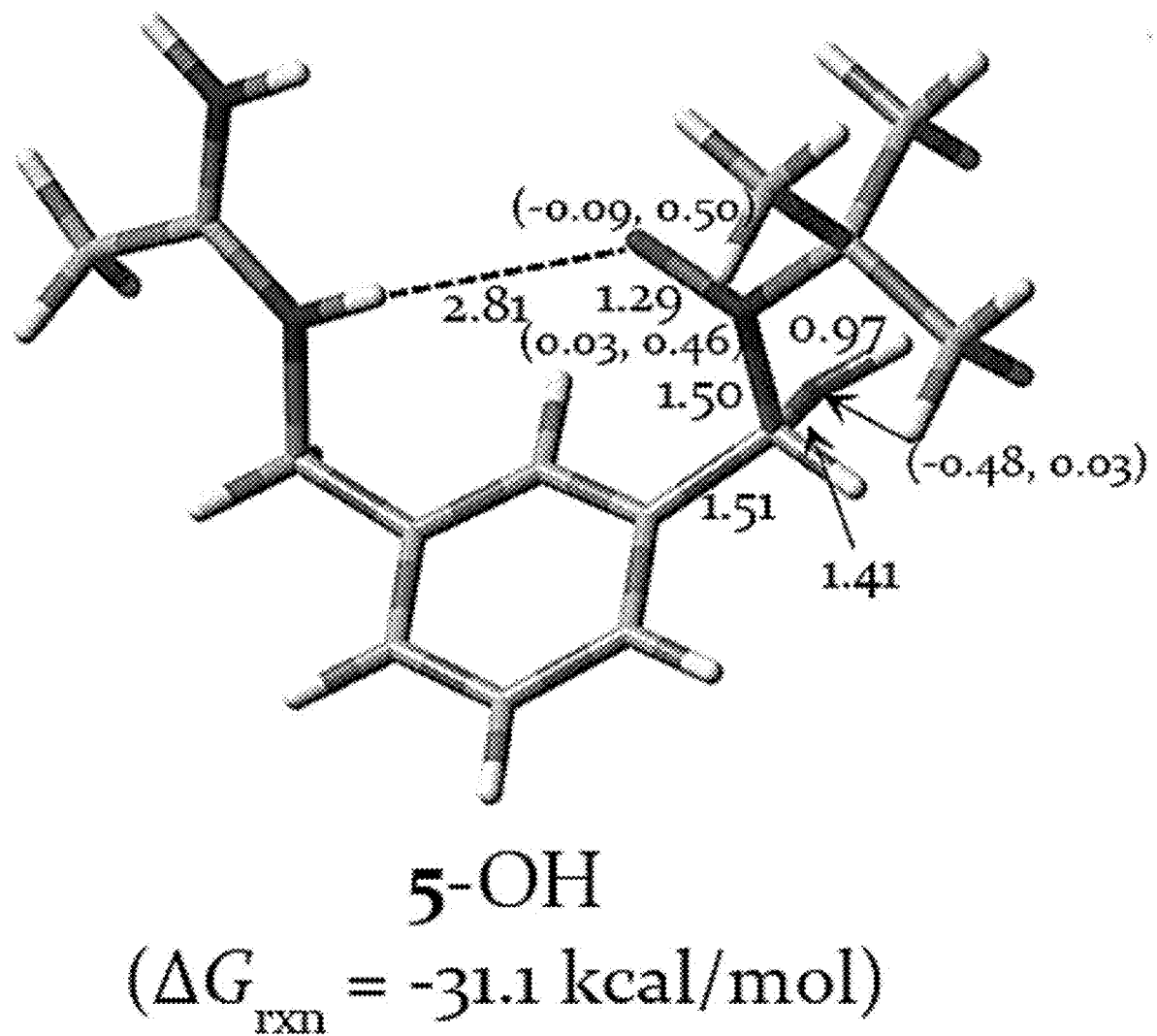
Figure 4F:
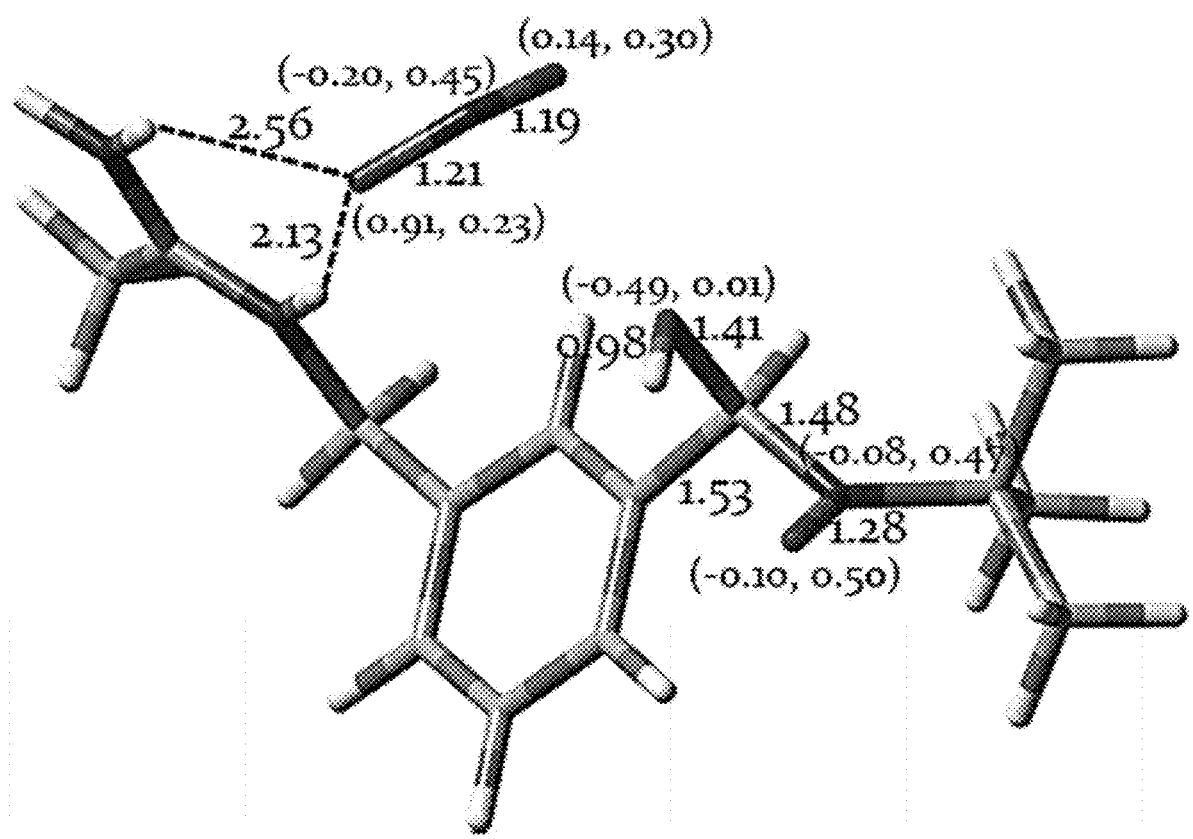
Figure 4G:
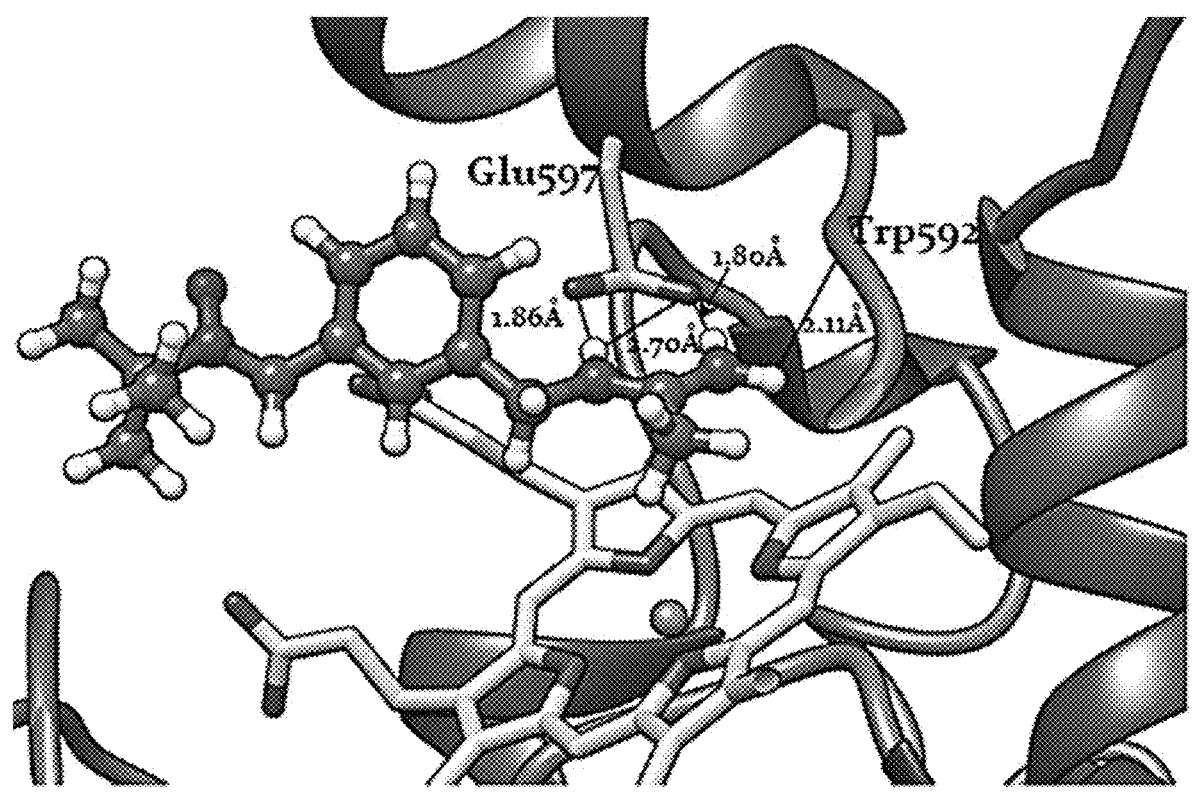
Figure 4H:
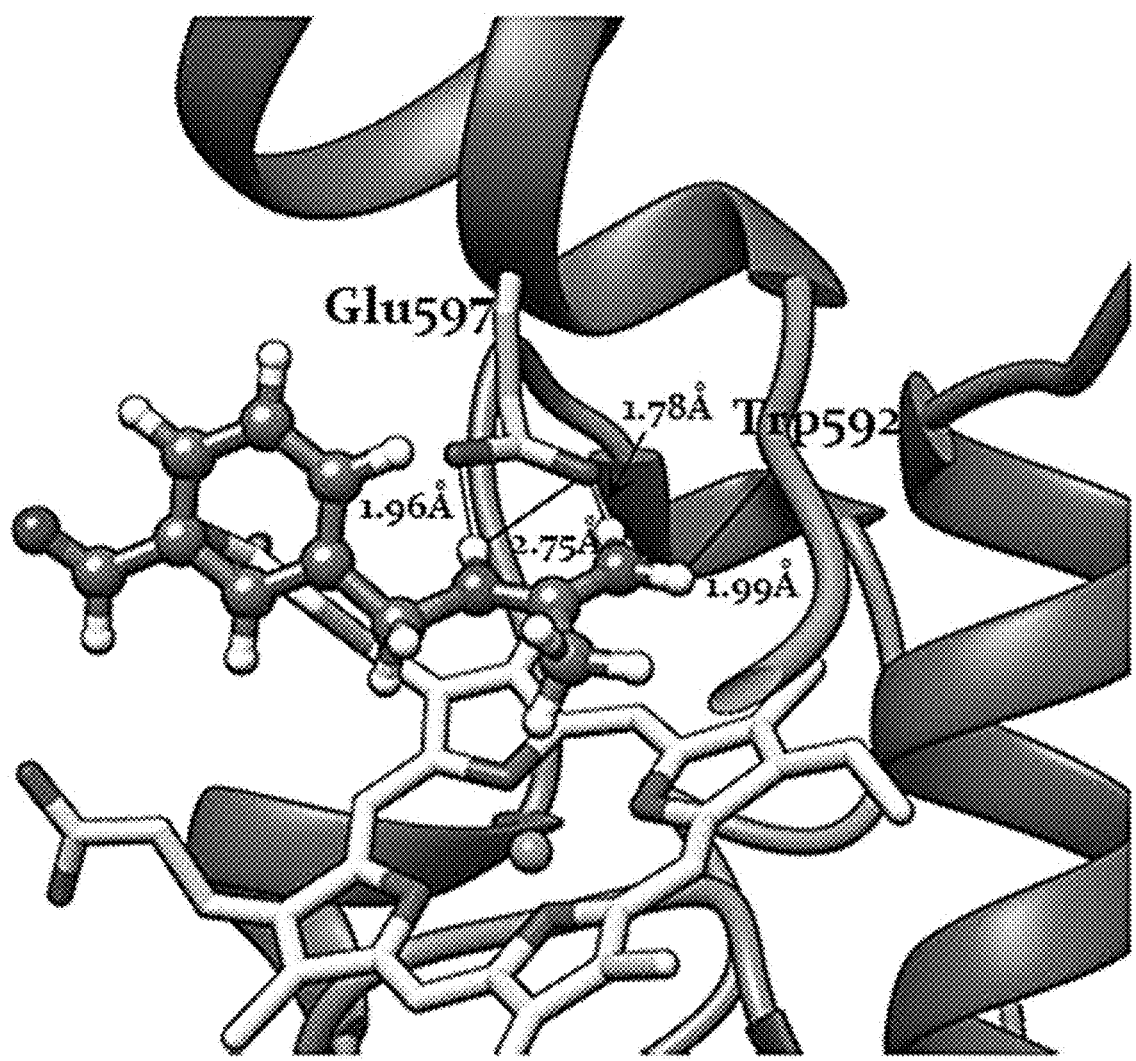
Figure 7A:
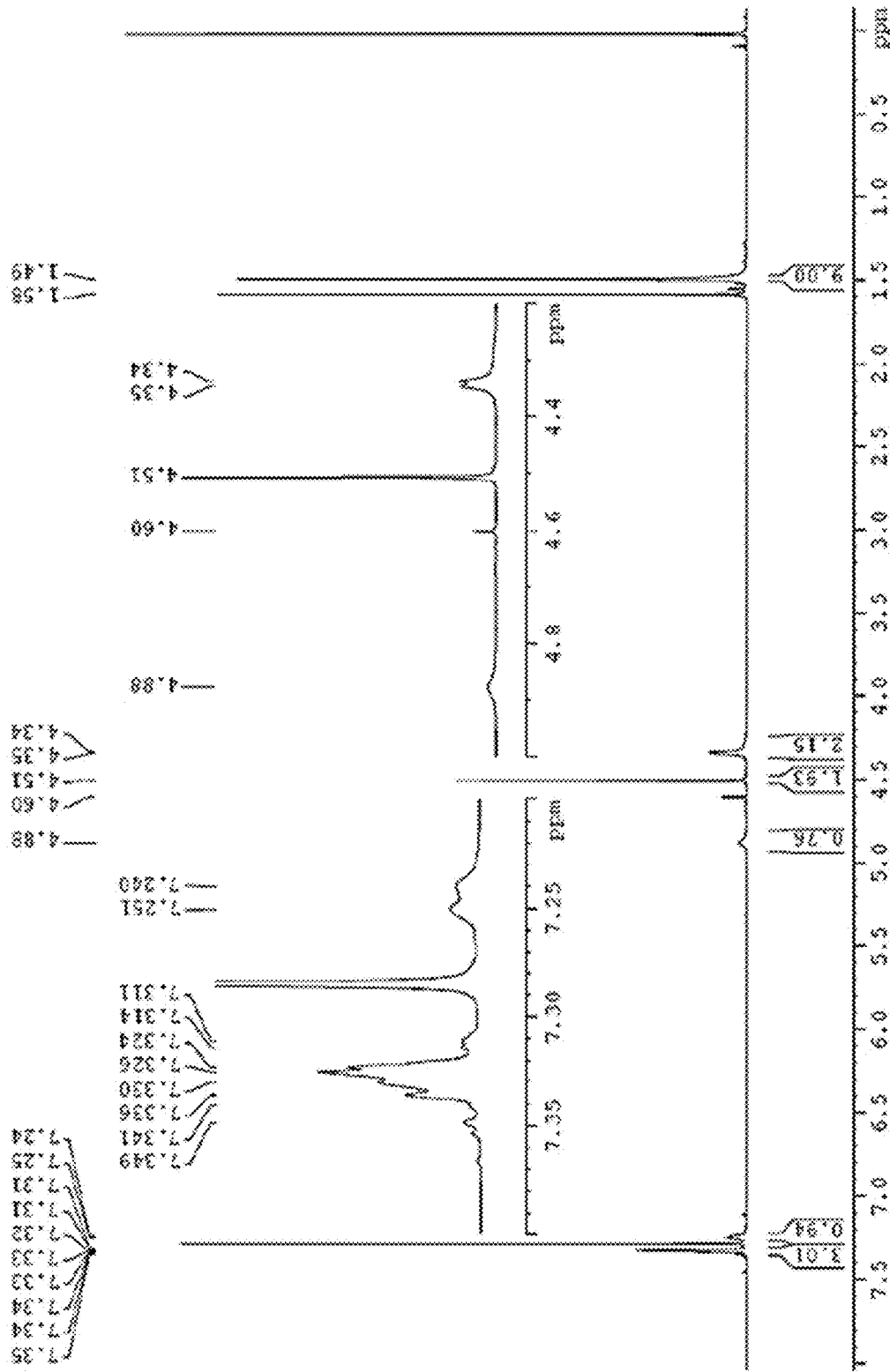
FIGS. 7A-7D: $^1$H NMR (FIG. 7A), $^{13}$C NMR (FIG. 7B), HPLC-PDA purity (FIG. 7C), and LRMS (FIG. 7D) of compound 2.
Figure 7B:
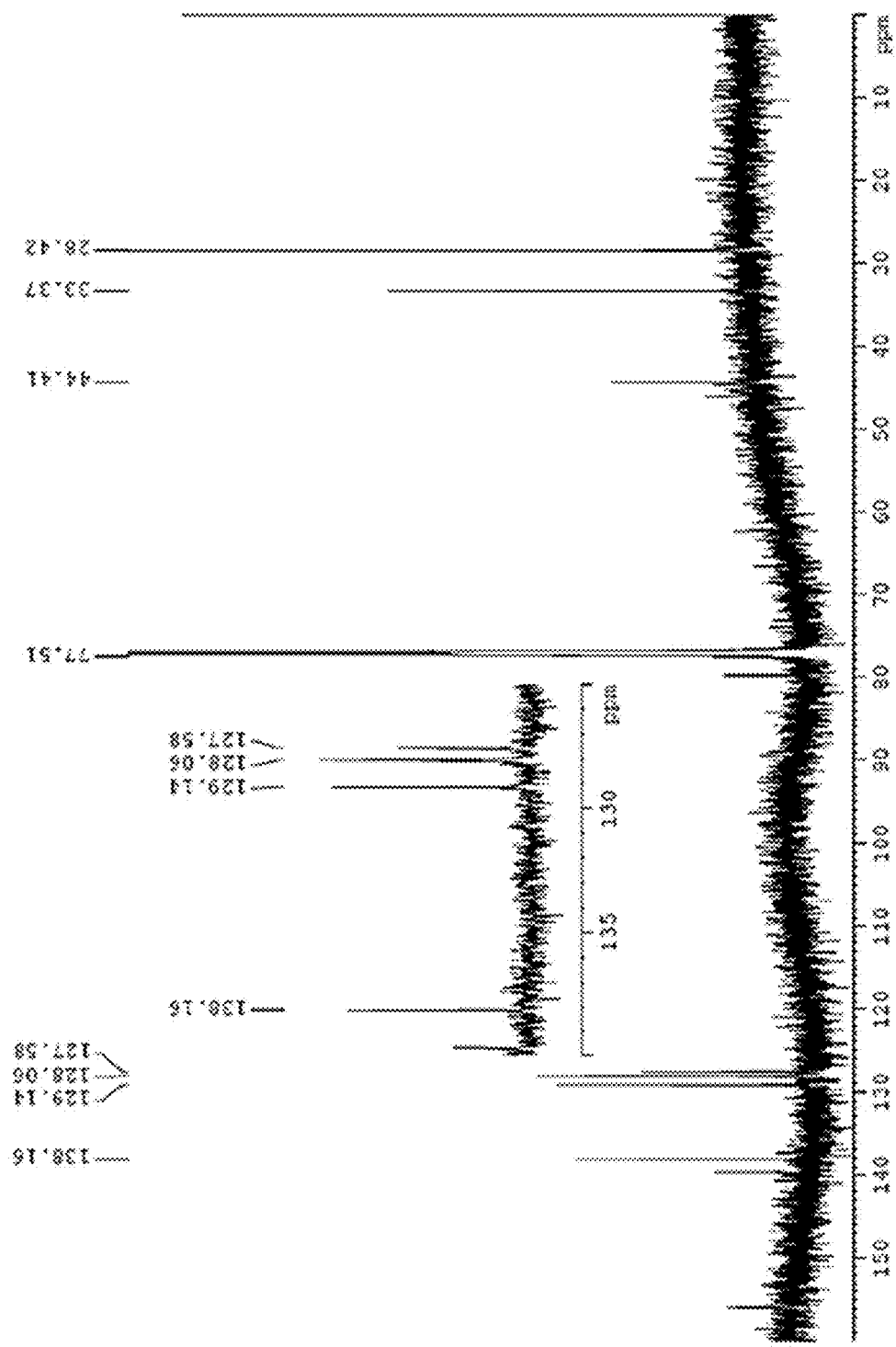
Figure 7C:
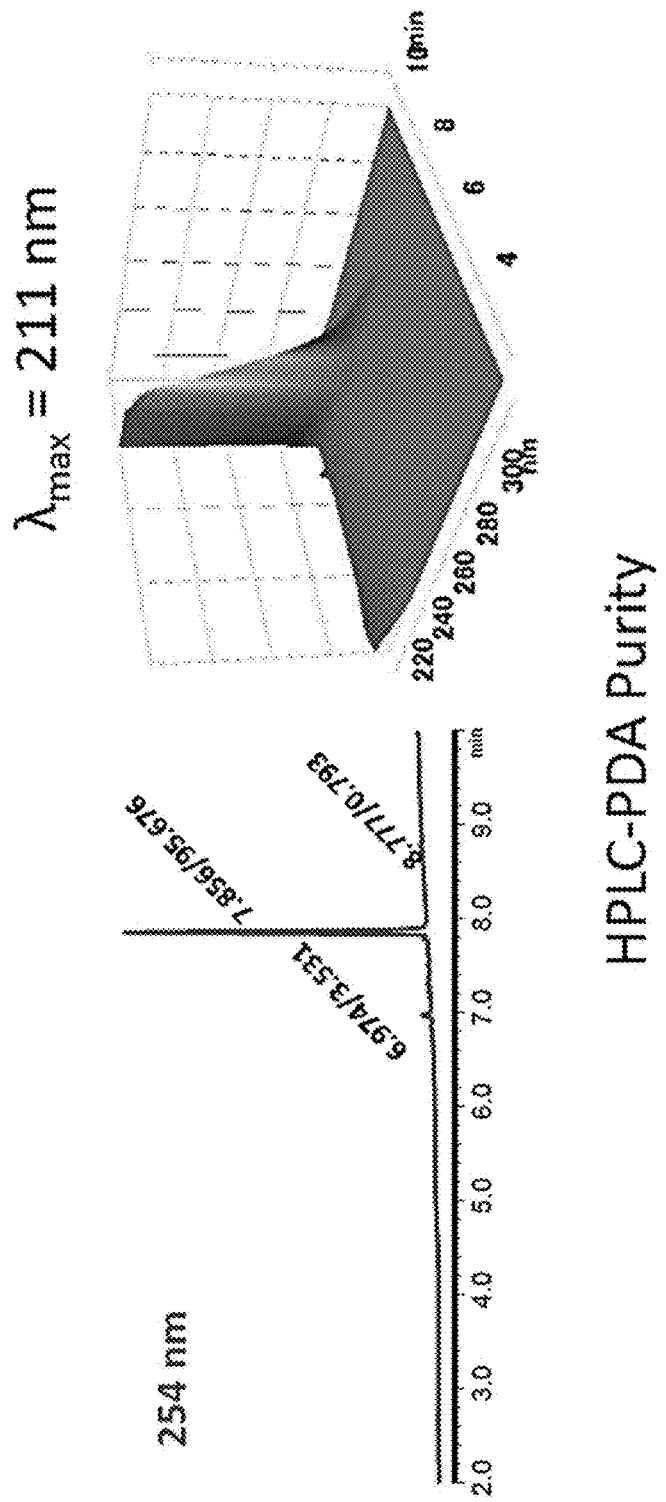
Figure 7D:
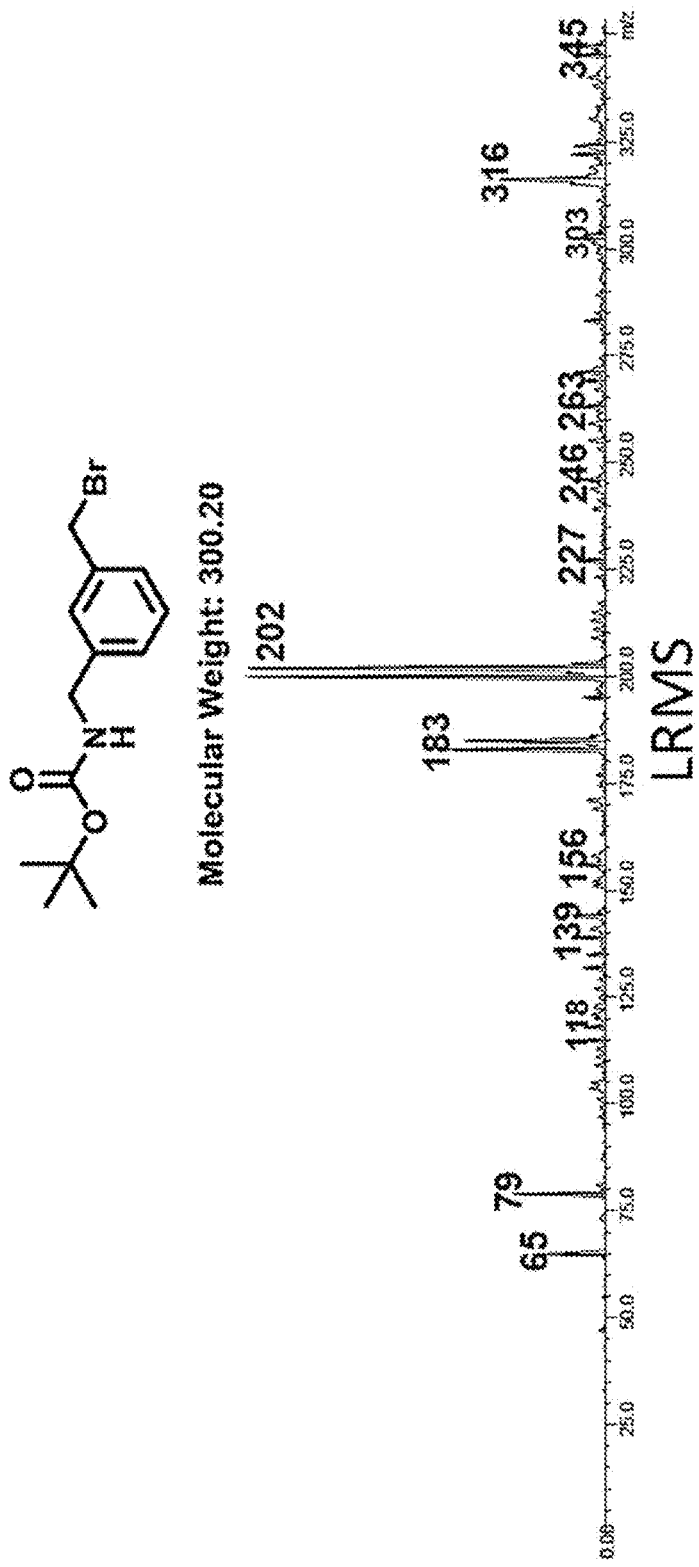
Figure 8A:
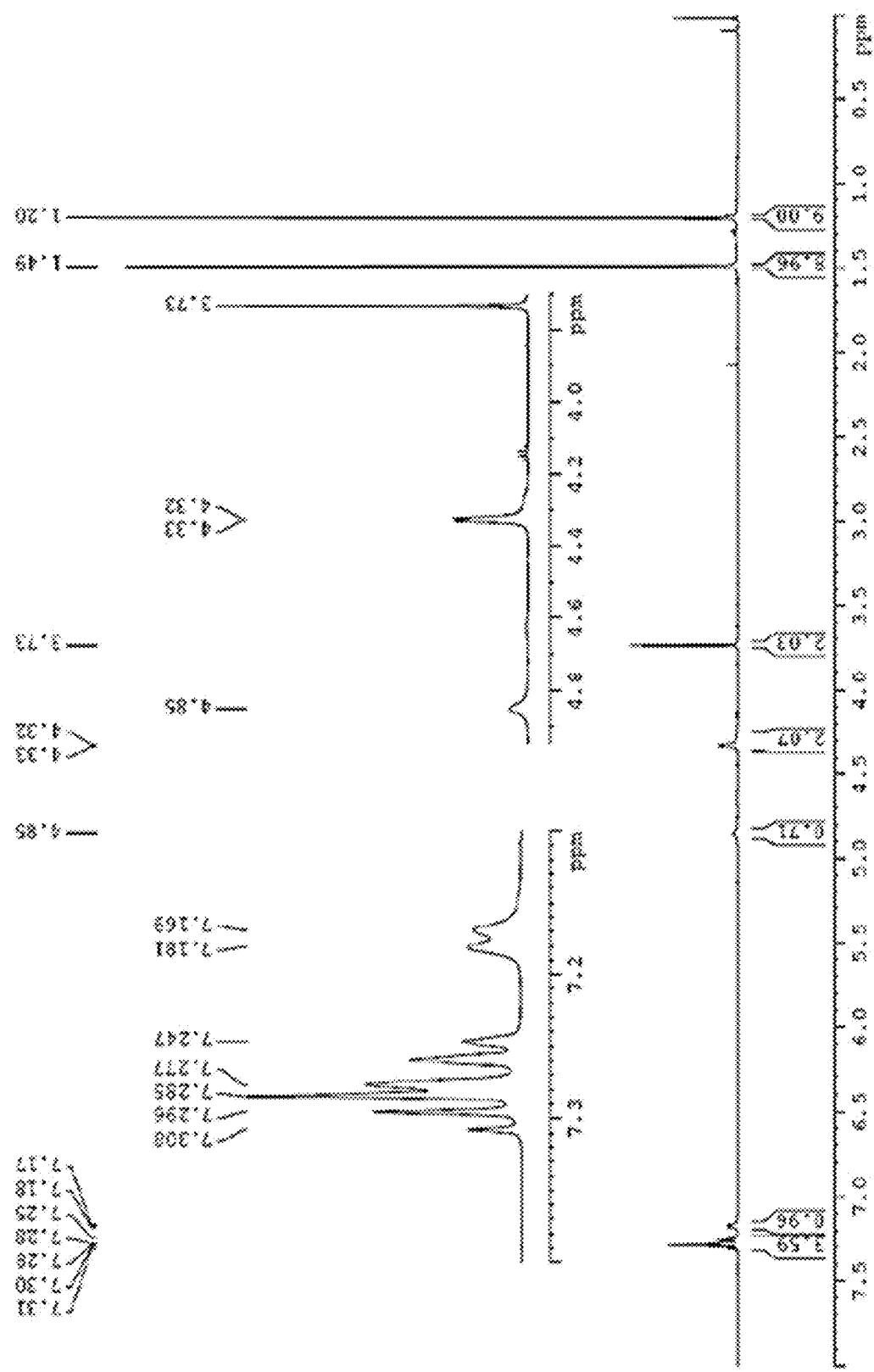
FIGS. 8A-8D: $^1$H NMR (FIG. 8A), $^{13}$C NMR (FIG. 8B), HPLC-PDA purity (FIG. 8C), and LRMS (FIG. 8D) of compound 3.
Figure 8B:
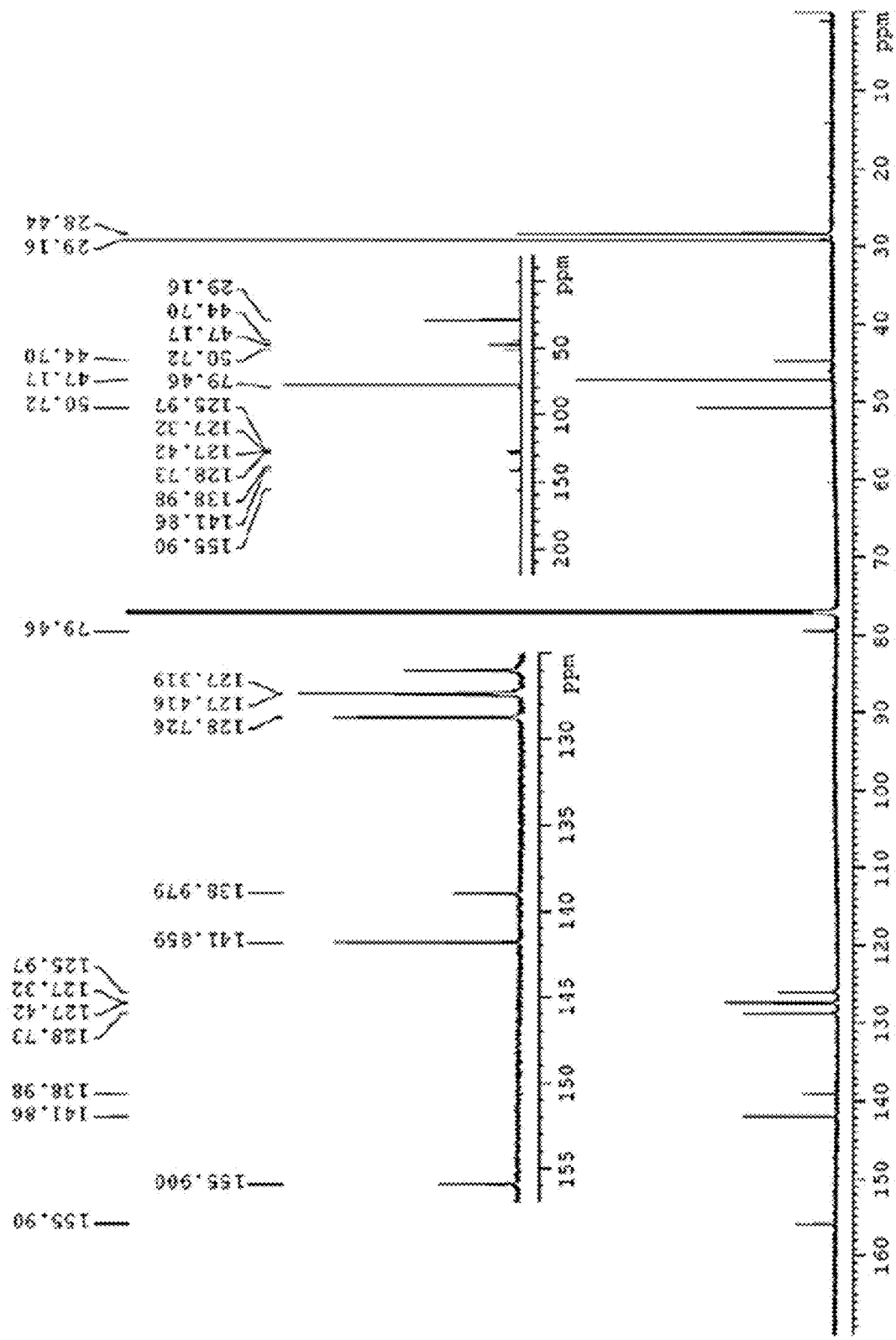
Figure 8C:
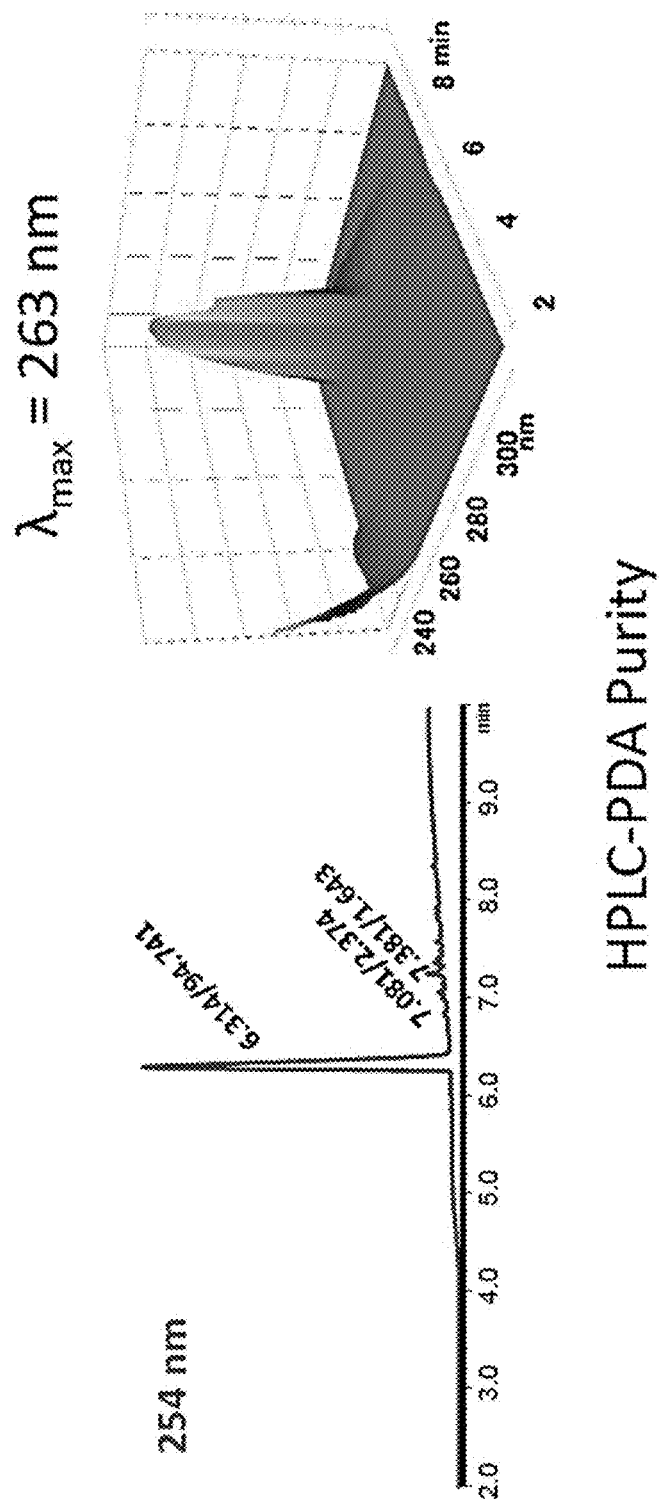
Figure 8D:
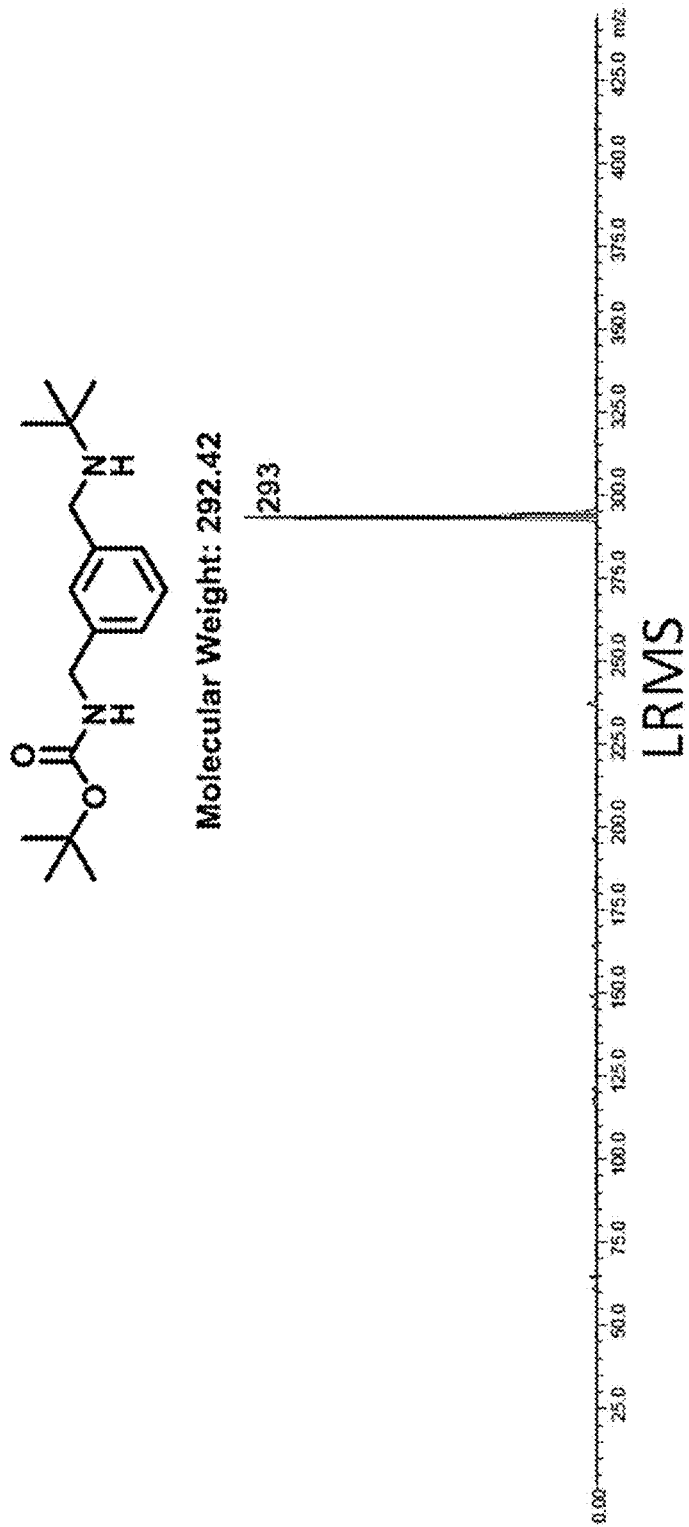
Figure 9A:
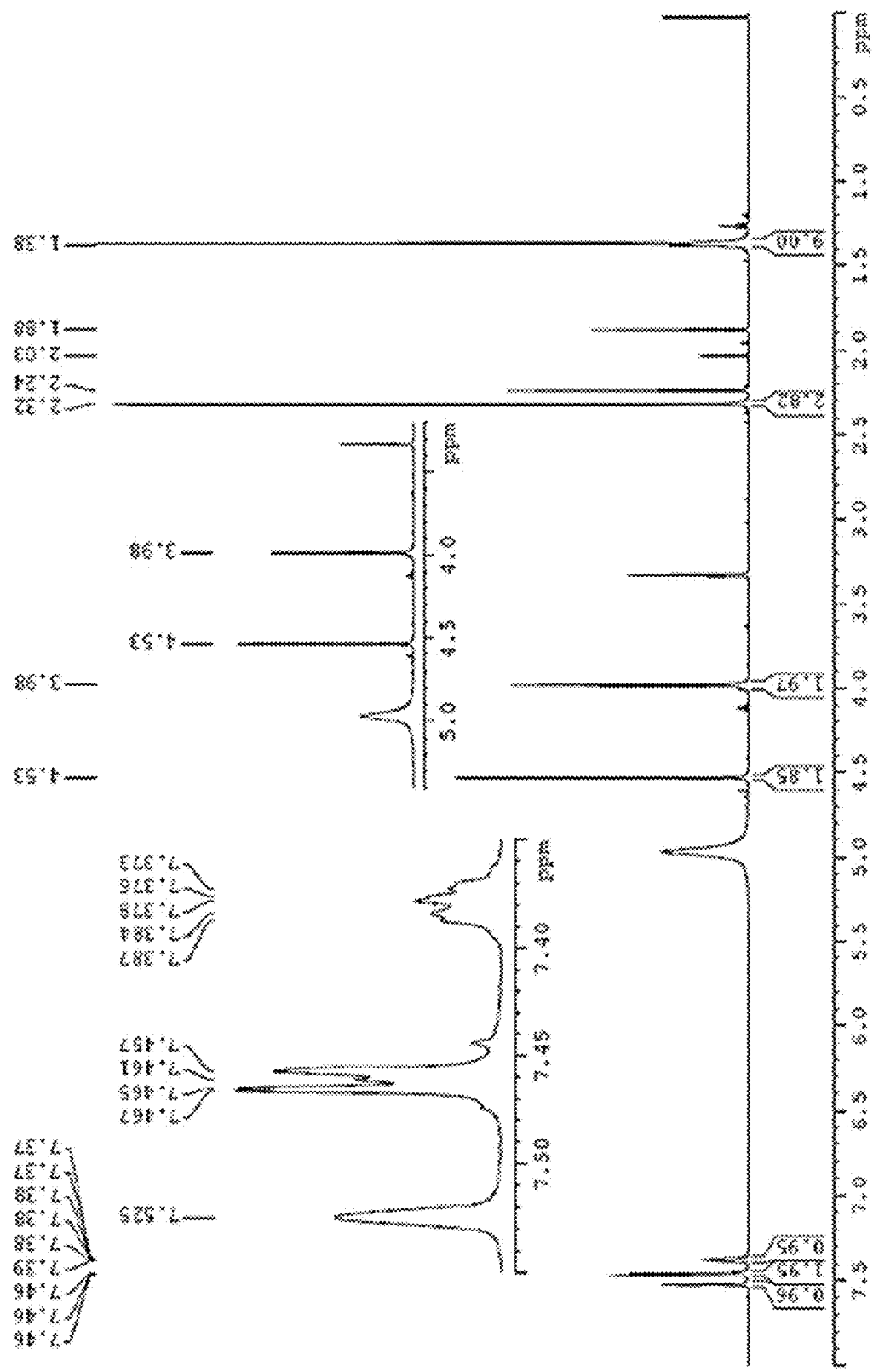
FIGS. 9A-9D: $^1$H NMR (FIG. 9A), $^{13}$C NMR (FIG. 9B), HPLC-PDA purity (FIG. 9C), and LRMS (FIG. 9D) of compound 4.
Figure 9B:
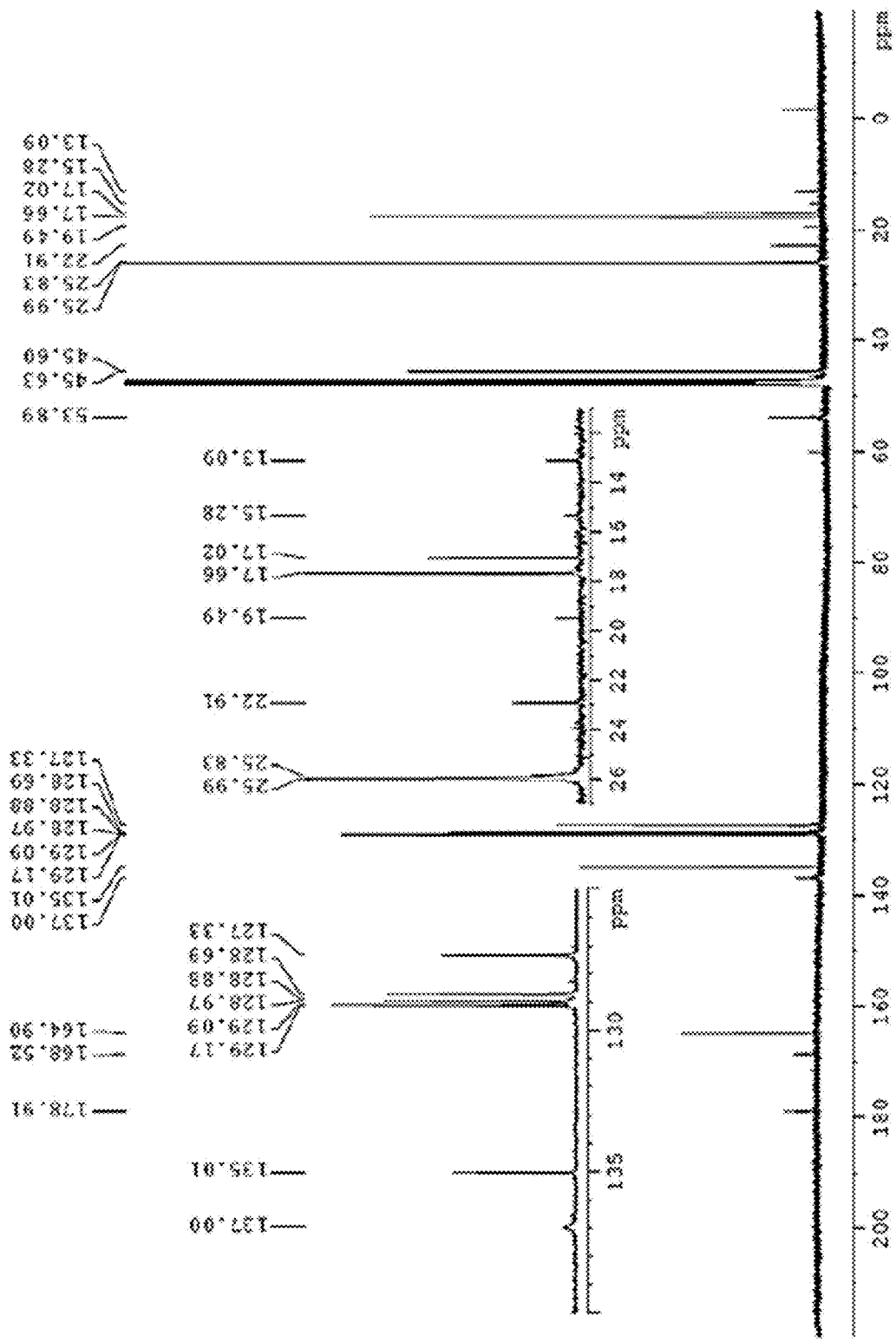
Figure 9C:
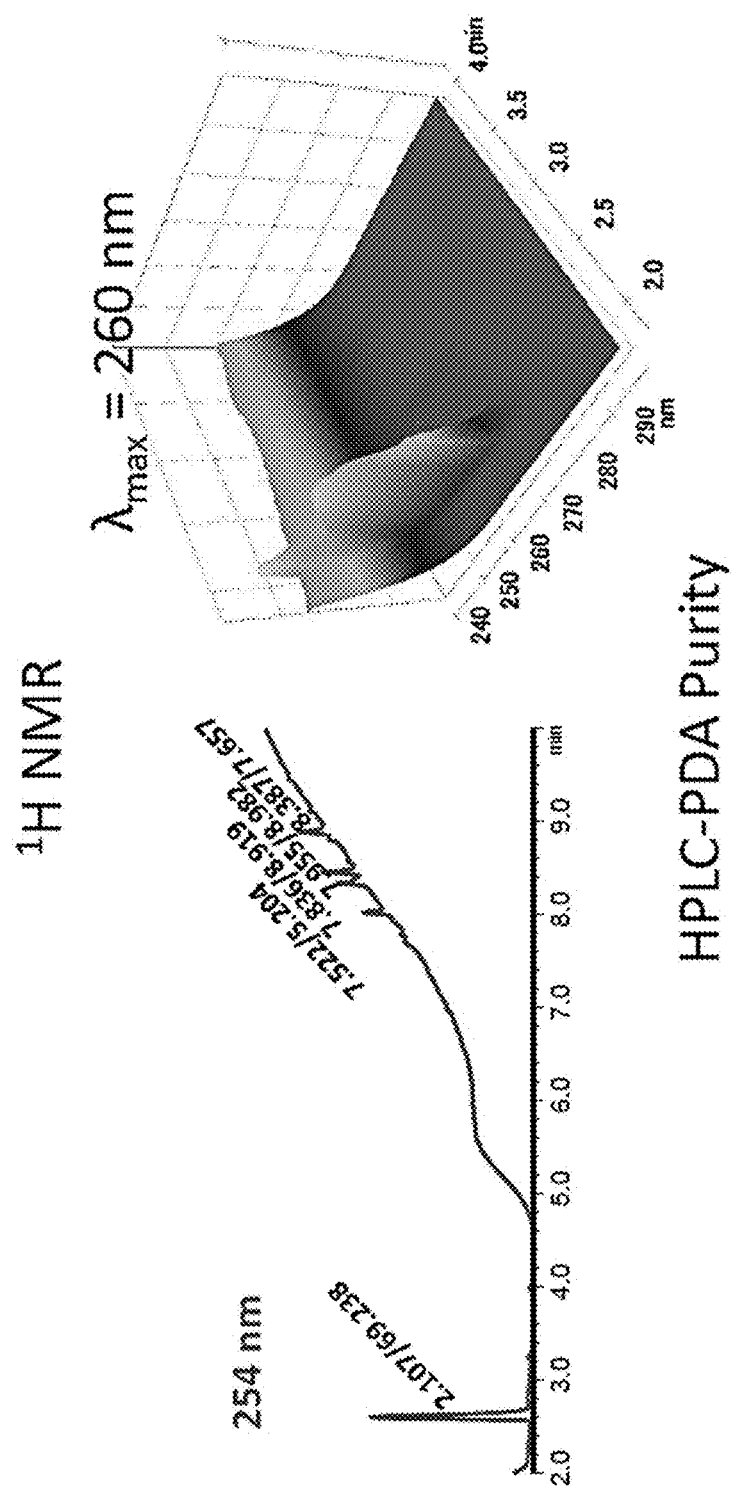
Figure 9D:
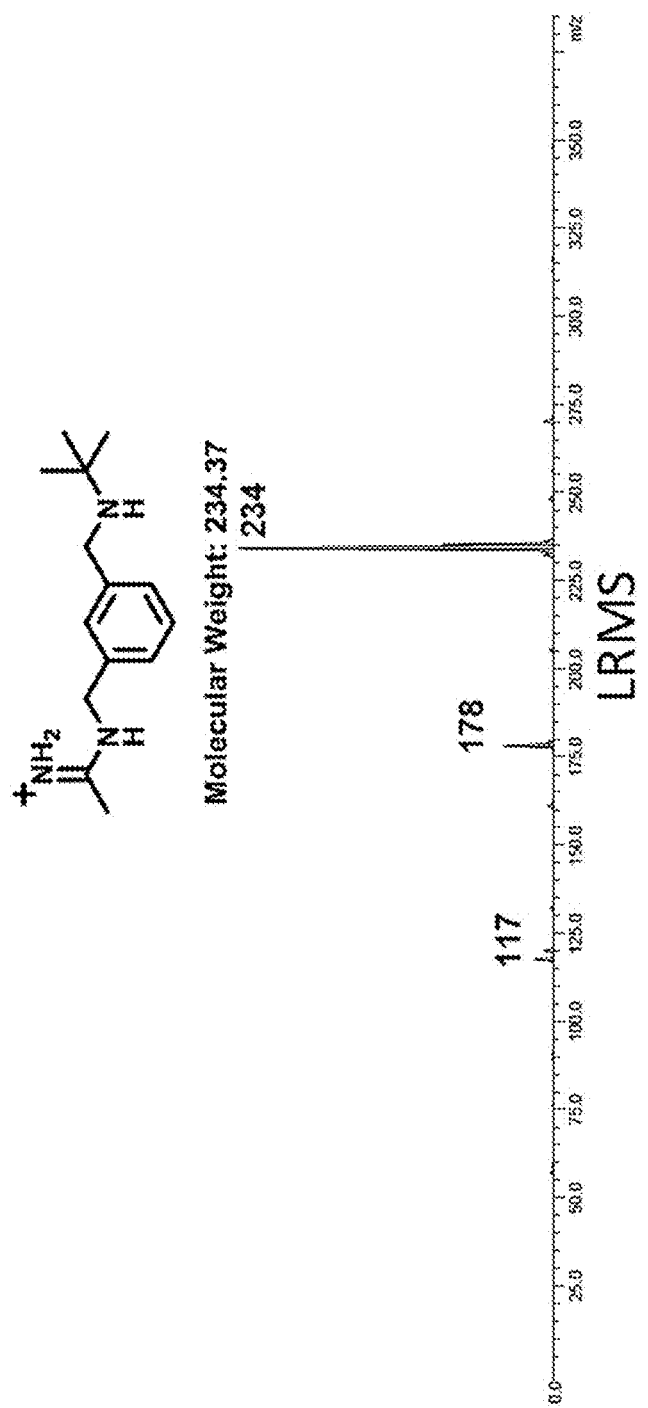
Figure 10A:
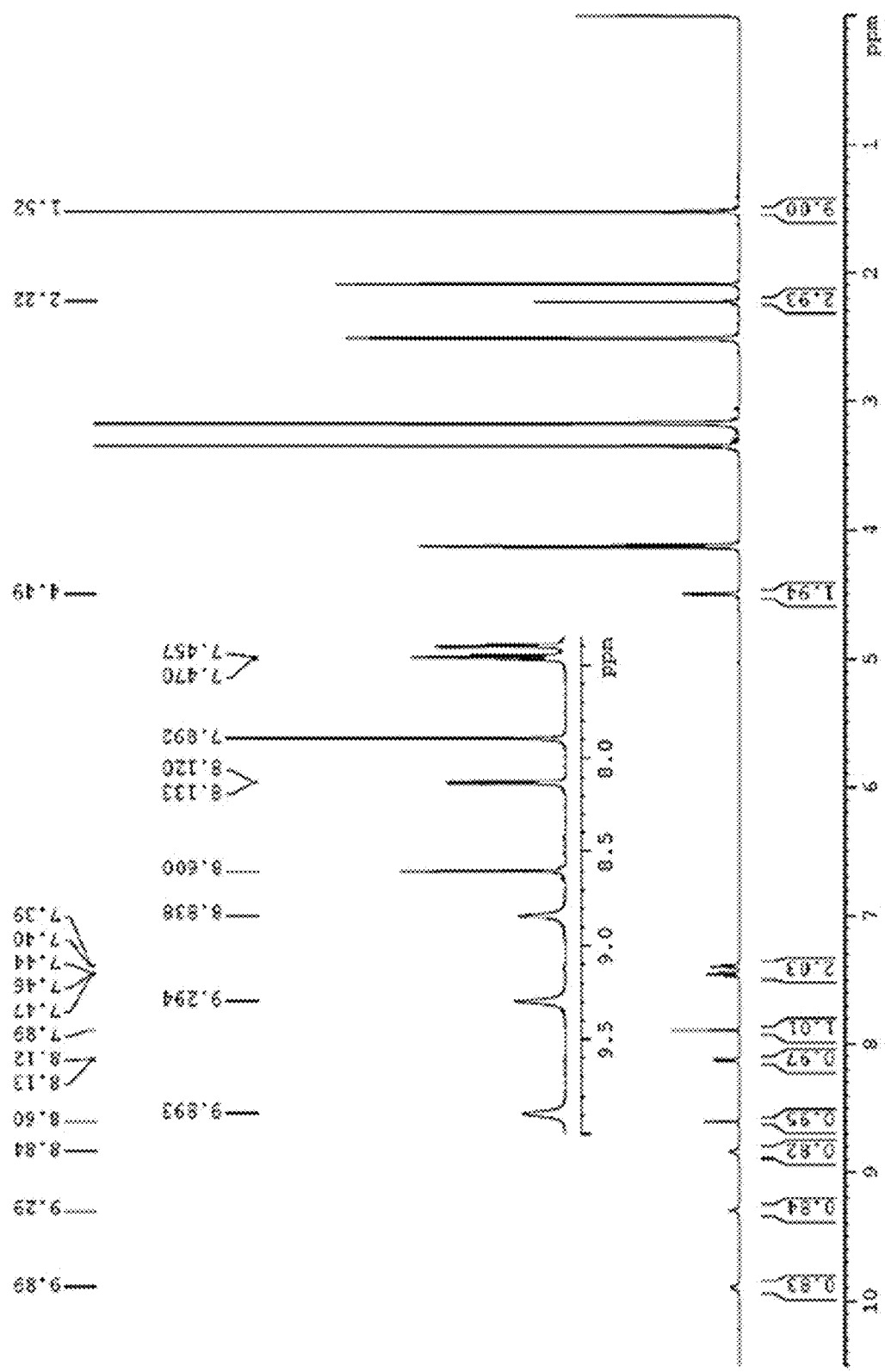
FIGS. 10A-10D: $^1$H NMR (FIG. 10A), $^{13}$C NMR (FIG. 10B), HPLC-PDA purity (FIG. 10C) and LRMS (FIG. 10D) of compound 5.
Figure 10B:
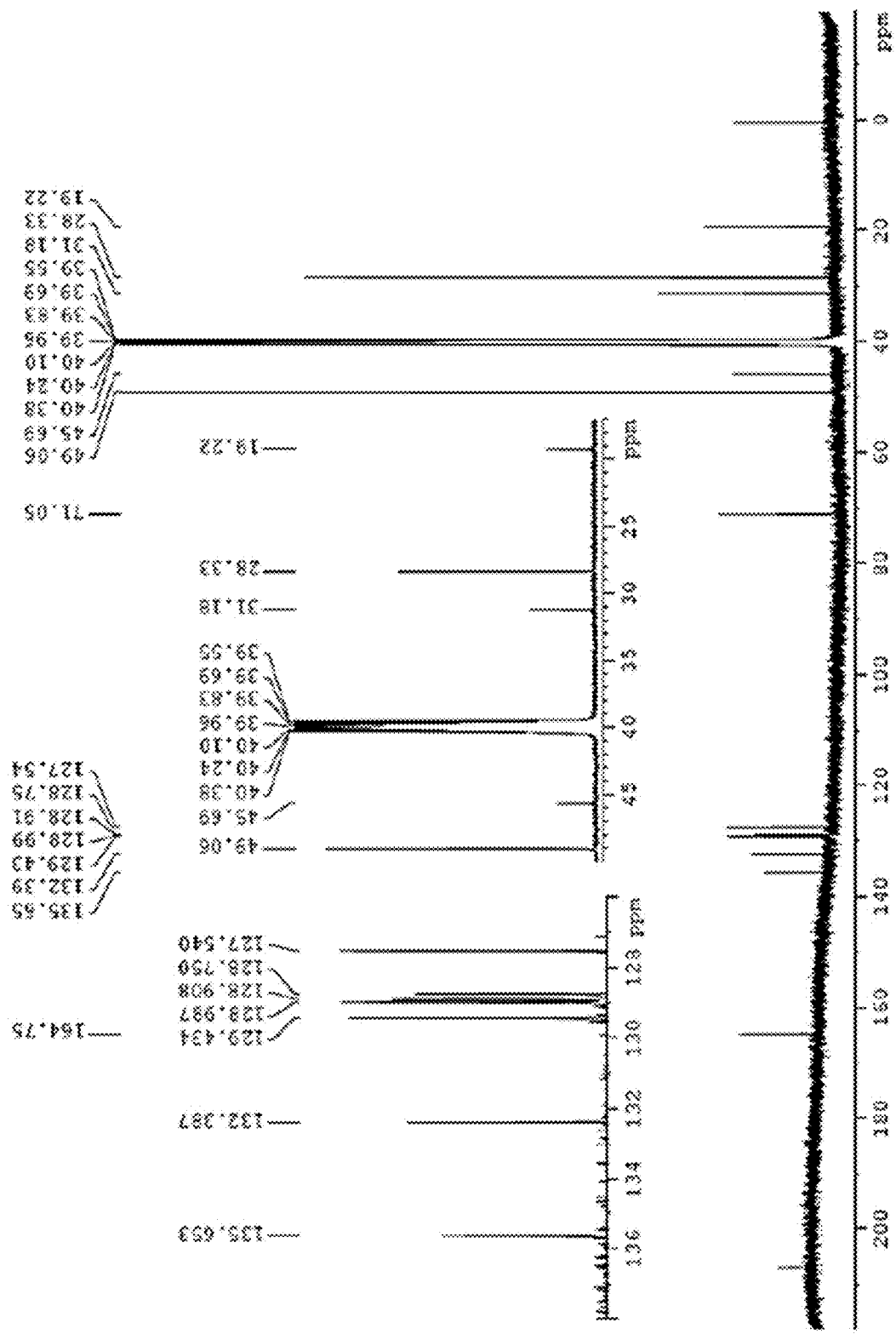
Figure 10C:
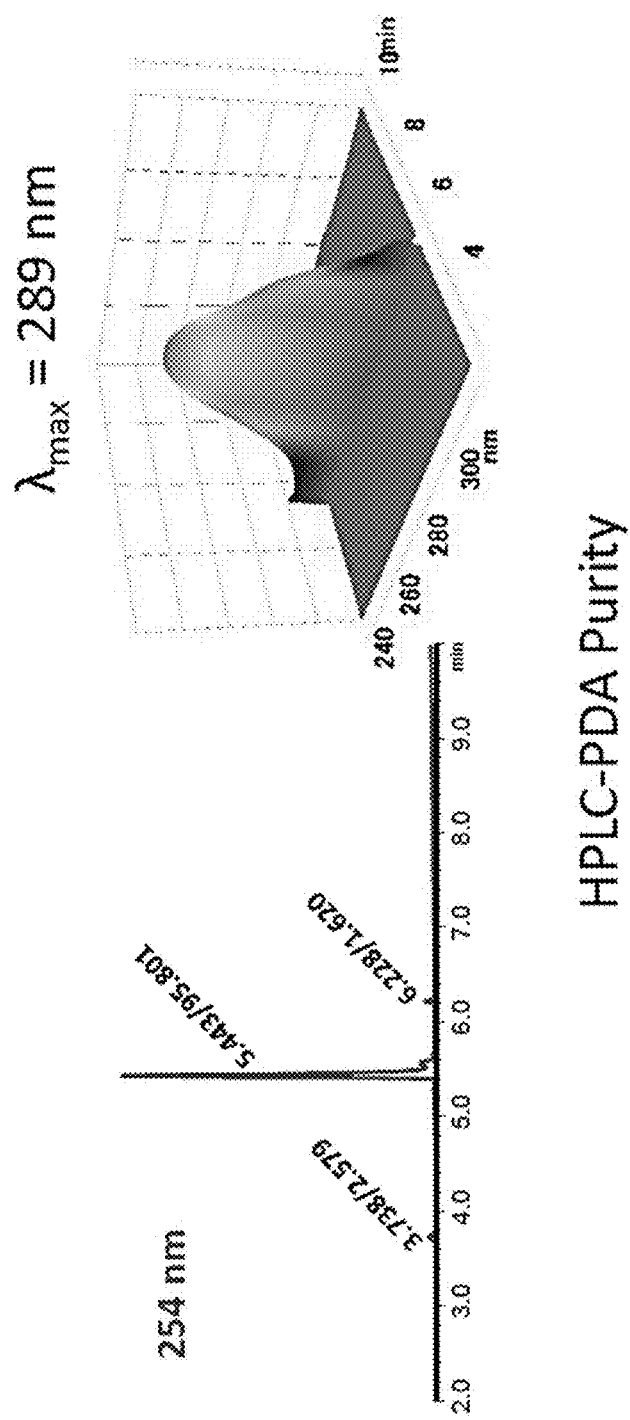
Figure 10D:
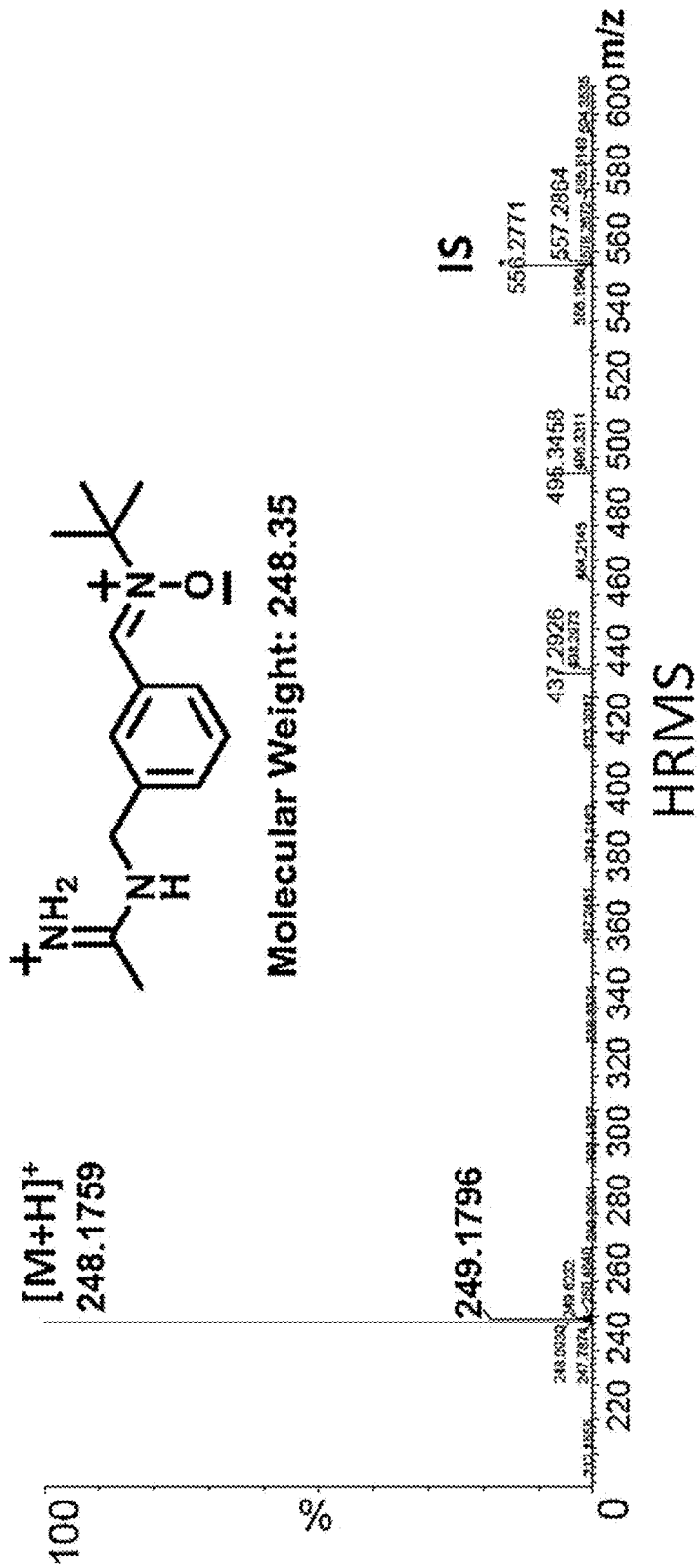

In general, the compounds of Formula I react with ROS to form NOS inhibitors (FIG. 1A, 4A) having the following general structural formula of Formula V:

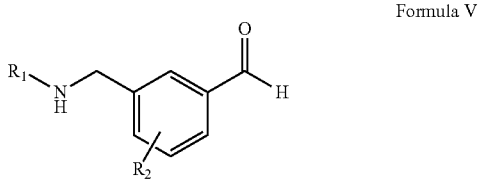

Formula V where $R_2$ is the same as the $R_2$ of the Formula I compound which reacted with ROS to produce Formula V, and $R_1$ amino, aminyl, amidinyl, nitroamidinyl, protonated aminyl, protonated amidinyl, protonated aminyl sulfide, thiopheneaminyl, ethyl aminyl, a heteroatom ring formed with the adjacent N, or a bridging group that binds to $R_2$ to form a ring. Thus, $R_2$ may be H or a bridging group that binds to $R_1$ to form a ring. Nitrone decomposition to benzaldehydes has been previously observed with other, distinct nitrones.

Conventional nitrones rely on an anti-oxidation mechanism. However, the compounds herein possess an additional action to yield benefits beyond those from conventional nitrones. Furthermore, conventional NOS inhibitors act globally, causing off-target effects. However, the compounds herein provide for site-specificity, which may solve the problem of major off-target effects to NOS inhibition. Without wishing to be bound by theory, it is believed this is due to the spin trapping mechanism.

Pharmaceutical compositions of the present disclosure comprise an effective amount of a compound of Formula I, and/or additional agents, dissolved or dispersed in a pharmaceutically acceptable carrier. The phrases "pharmaceutical" or "pharmacologically acceptable" refer to molecular entities and compositions that produce no adverse, allergic, or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety, and purity standards as required by FDA Office of Biological Standards.

A composition disclosed herein may comprise different types of carriers depending on whether it is to be administered in solid, liquid or aerosol form, and whether it needs to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, intraosseosly, periprosthetically, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543, 158; 5,641,515; and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In some cases, the form should be sterile and should be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In some cases, it may be desirable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution may be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed are known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, but not limited to, water or a saline solution, with or without a stabilizing agent.

In other embodiments, the compositions may be formulated for administration via various miscellaneous routes, for example, topical (i.e., transdermal) administration, mucosal administration (intranasal, vaginal, etc.), and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum, as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation is composed of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age and weight, as well as the severity and response of the symptoms.

In particular embodiments, the compositions described herein are useful for treating ischemic stroke. Furthermore, the compositions may be used in combination therapies. That is, the compositions may be administered concurrently with, prior to, or subsequent to one or more other desired therapeutic or medical procedures or drugs. The particular combination of therapies and procedures in the combination regimen will take into account compatibility of the therapies and/or procedures and the desired therapeutic effect to be achieved. Combination therapies include sequential, simultaneous, and separate administration of the active ingredient in a way that the therapeutic effects of the first administered procedure or drug is not entirely disappeared when the subsequent procedure or drug is administered.

By way of a non-limiting example of a combination therapy, the compositions described herein can be administered in combination with one or more suitable other treatments for ischemic stroke, including, but not limited to, tissue plasminogen activator (tPA), which is generally administered intraveneously. One or more compounds of Formula I may be administered simultaneously to, before, or after administration of tPA.

Another non-limiting example of a combination therapy is the combination of a Formula I compound, or composition containing a Formula I compound, with one or more surgical interventions, such as draining or removing blood that is in or around the brain.

The compositions and methods described herein can be embodied as parts of a kit or kits. A non-limiting example of such a kit is a kit for preparing a compound of Formula I, comprising a substituted benzaldehyde and at least one of an N-alkyl hydroxylamine, N-aryl hydroxylamine, N-heteroaryl hydroxylamine, N-aryloxy hydroxylamine, N-alkoxy hydroxylamine, or N-heterobicyclicyl hydroxylamine, in separate (or at least two or more) containers, where the containers may or may not be present in a combined configuration. Many other kits are possible, such as kits further comprising a pharmaceutically acceptable carrier, adjuvant, or diluent. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

Embodiments of the present disclosure further include methods of determining coverage or denial of health insurance reimbursement and/or payment for treatments of disease comprising the compositions or methods described herein. In certain embodiments, the treatment comprises a compound of Formula I, and a provider of health insurance denies coverage or reimbursement for the treatment.

EXAMPLES

In this example, the PBN-type nitrone 5 was designed such that its decomposition product is a NOS inhibitor, effectively leading to NOS inhibition specifically at the site of ROS production. The ability of 5 to spin-trap radicals and decompose into the putative NOS inhibitor was observed using EPR and LC-MS/MS. The pro-drug concept was tested in vitro by measuring cell viability and inhibitor formation in SH-SY5Y cells subjected to oxygen glucose deprivation (OGD). Compound 5 was found to be more efficacious and more potent than PBN, and was able to increase pAkt while reducing nitrotyrosine and cleaved caspase-3 levels. Doppler flowmetry on anesthetized mice showed an increased cerebral blood flow upon intravenous ad-ministration of 1 mg/kg 5, but a return to baseline upon administration of 10 mg/kg, likely due to its dual nature of antioxidant/NO-donor and NOS-inhibition properties. Mice treated with 5 after permanent middle cerebral artery occlusion (pMCAO) performed better in neurobehavioral assessments and exhibited a >30% reduction in infarct volume. This efficacy is believed to be due to higher formation of the NOS inhibitor decomposition product in ischemic tissue observed by LC-MS/MS, resulting in region specific effects limited to the infarct area.

Stroke remains one of the leading causes of death and disability in the United States, most notably ischemic stroke which accounts for over 80% of all stroke cases. Despite decades of promising research, clinical trials of potential therapeutics have not successfully led to novel treatments for the devastating effects of cerebral ischemia. Ischemic stroke is associated with inflammatory and free radical-mediated cell death due to obstruction of blood flow to the brain. Reactive oxygen species (ROS) such as superoxide ($O_2.^-$) are generated under hypoxic and inflammatory pathologies by the mitochondrial electron transport chain (ETC), NADPH oxidase, and xanthine oxidase (XO). This oxidative burst causes direct DNA, protein, and cell membrane damage which ultimately leads to cell death in the core of the ischemic lesion. Additionally, $O_2.^-$ is known to cause vasoconstriction independent of its effect on nitric oxide (NO), which is detrimental to patient outcome. Increased levels of oxidative stress markers and decreased levels of antioxidant markers have a strong correlation with worse ischemic stroke outcome.

NO is a free-radical, paracellular signaling molecule produced by $Ca_2^+$-dependent endothelial NO synthase (eNOS) and neuronal NOS (nNOS), and inducible NOS (iNOS). Canonical NO signaling involves the increase in cGMP through activation of guanylyl cyclase to cause vasodilation through vascular smooth muscle relaxation. It has been shown that NO is also involved in GABA4 and 5-HT neurotransmission, neurogenesis, mitochondrial signaling, and post-translational protein modification. During cerebral ischemia, a dramatic increase in intracellular $Ca_2^+$ causes increased NOS activity through calmodulin binding concomitant with the generation of ROS and activation of pro-apoptotic pathways. The overall role of NO in ischemic stroke is still unclear; inhaled NO was shown to be clinically ineffective, while endogenous NO generated by NOS is observed to have beneficial effects. NOS can uncouple under ischemic conditions through direct oxidation or oxidation of cofactors to instead produce $O_2.^-$, which is scavenged by NO to form the highly reactive peroxynitrite ($ONOO^-$). This phenomenon was initially observed with eNOS, but has since been detected from each NOS isoform.

The pan-NOS inhibitor Nω-nitro-L-arginine methyl ester (L-NAME) has been shown to subdue $O_2.^-$ production in tissues with NOS dysfunction. L-NAME administered to tissue with functional NOS increased $O_2.^-$ production. However, this indicates a targeted approach to dysfunctional NOS inhibition would be preferable to total NOS inhibition. Isoform-specific inhibitors for nNOS or iNOS have shown reduced in vivo stroke volume in animal models, while pan-NOS inhibitors exhibit mixed results. This may be due to the inhibition of functional NOS as well as uncoupled NOS which can cause global adverse effects that limit their protective effects in ischemia.

Antioxidant molecules that scavenge oxidative species such as Edaravone, Ebselen, and uric acid have shown pre-clinical promise in ischemia, but have fallen short in clinical applications. The nitrone NXY-059 had advanced to phase III clinical trials, showing good safety and tolerability before it was deemed ineffective in the treatment of acute ischemic stroke. Nitrones (FIG. 1B) are synthetic antioxidants that are shown to both scavenge ROS and produce NO upon decomposition to yield neuroprotective effects under ischemic conditions. Linear, N-tert-butyl-α-phenylnitrone (PBN)-type nitrones have been extensively developed for use in pre-clinical models of stroke including innovative derivations such as a tetra-methylpyrazine nitrone (TBN), which possesses anti-platelet activity, and a PBN-containing, PEGylated nanoparticle capable of extended exposure.

Synthetic nitrones and NOS inhibitors have thus far failed to yield favorable clinical outcomes in diseases mediated by oxidative pathologies. This example resolves their limitations through a pro-drug approach to the elimination and prevention of oxidative species. The molecule described in this example, 5, is a nitrone designed based on its radical adduct decomposition product. This decomposition product is a putative NOS inhibitor that is effectively formed at the site of oxidative stress, selectively targeting dysfunctional, uncoupled NOS. In this example, an in silico computational approach for designing 5 and its product 6 is described, along with in vitro and in vivo models of cerebral ischemia pathology.

Results

Thermodynamics of Free Radical Addition to 5

It has been shown that oxygen-centered radical addition to PBN nitrones causes nitronyl bond cleavage to form a tert-butyl hydroxylamine and a benzaldehyde. The amidine-containing NOS inhibitor 1400W exhibits strong selectivity for iNOS, while also showing inhibition of nNOS and eNOS at higher concentrations. For this example, the PBN-type nitrone 5 was designed to form the putative NOS inhibitor 6 after reaction with oxygen-centered radicals (FIGS. 4A-4H). Amidine moieties typically exhibit an NH pKa>10, thus the protonated forms of 5 and 6 were used for all in silico calculations. Multiple bio-logically relevant oxygen-centered free radicals were chosen for calculation of reaction thermodynamics. FIGS. 4A-4H show calculated geometries of 5 and adducts formed from $O_2^{.-}/HO_2$. (pKa 4.8), .OH, and $ONOO^-/ONOOH$ (pKa 6.8). Calculated $\Delta G_{rxn}$ for radical addition to 5 and PBN are summarized in Table 1. FIGS. 5A-5E show the thermodynamic parameters of ROS-PBN and 5 adducts.

TABLE 1

Calculated free energies of reaction ($\Delta G_{298K}$, kcal/mol) of oxygen-centered free radical species to form nitronyl spin adducts at the PCM/B$_3$LYP/6-$_{31}$ + G(d, p)//B$_3$LYP/6-$_{31}$G(d) level of theory

| Radical Adduct | PBN | 5 |
|---|---|---|
| —$O_2^-$ | 19.8 | 1.6 (12.6)[a] |
| —$O_2H$ | 2.1 | 3.2 |
| —OH | −32.7 | −31.1 |
| —OONO[b] | 32.5 | −6.7 |
| —HOONO[c] | −23.4 | −20.4 |

[a]With two explicit water molecules
[b]Triplet products of a O-3 cis-OONO adduct
[c]Triplet products of a O-3 trans-HOONO adduct Optimized geometries of $O_2^{.-}$ addition to 5 calculated by Gaussian 09 predict proton abstraction of the amidine-NH to protonate the peroxyl anion adduct. While this resulted in a lower $\Delta G_{rxn}$ (1.6 kcal/mol), it is more likely that the peroxyl anion would abstract a proton from solution. Indeed, when the calculation was performed with two explicit water molecules, the $\Delta G_{rxn}$ of 5-$O_2^{.-}$ was closer to that of PBN—$O_2^{.-}$ (12.6 kcal/mol and 19.8 kcal/mol, respectively).

Peroxynitrite and its conjugate acid ONOOH are highly oxidizing species that have been shown to react with nitrones to yield radical products as detected by EPR. The $\Delta G_{rxn}$ of potential triplet products was calculated, and predicted a favorable reaction of 5 with the relatively stable cis-ONOO— to give $NO_2$, as compared to an unfavorable reaction with PBN (−6.7 kcal/mol and 32.5 kcal/mol, respectively). Overall, the effect of the H-bond donating amidine group is predicted to have favorable effects on the $\Delta G_{rxn}$ with anionic ROS. This is in line with previous observations with nitrones containing intramolecular H-bond donors.

Predictive Binding of 5 and 6 with NOS Isozymes

To predict if the nitrone 5 and its decomposition product 6 interact with the active site of each NOS isoform, docking using Swissdock.ch was performed. PDB structures of each NOS isoform bound with native ligand L-arginine, and those with bound 1400W were used (6 structures total). FIGS. 6A-6D show the docketing parameters of 5, 6, and L-arginine and 1400W with NOS isozymes used. Results of predicted interaction with the orthosteric binding site are summarized in Table 2. The ΔG of ligand binding for 5 and 6 were found to be similar for each NOS isoform; the most favorable interaction was with iNOS, and the least favorable interaction was with nNOS. Both molecules gave similar predicted ΔG as that of L-arginine for each structure, with the exception of nNOS in which 5 and 6 had more favorable predicted binding for both nNOS structures. 1400W showed the most favorable binding for each structure, although seemingly similar to L-arginine for iNOS binding ΔG in spite of its high affinity (Ki=7 nM). Upon calculating favorable interactions with NOS active sites and promising $\Delta G_{rxn}$ for free radical reactions, compound 5 was synthesized.

TABLE 2

Predicted free energies of binding ($\Delta G_{298K}$, kcal/mol) of ligands with NOS isozymes (L-arginine/1400 W x-ray crystallo-graphic structures)[a]

| Ligand | eNOS[b] | iNOS[c] | nNOS[d] |
|---|---|---|---|
| L-arginine | −10.32/−9.31 | −10.64/−10.21 | −7.78/−8.43 |
| 1400 W | −10.37/−10.34 | −10.68/−11.56 | −8.62/−10.26 |
| 5 | −9.99/−10.11 | −10.07/−10.75 | −8.29/−9.88 |
| 6 | −9.73/−9.88 | −9.76/−10.09 | −8.83/−9.77 |

[a]Docking performed by Swissdock.ch
[b]eNOS L-arginine PDB: 4D1O; 1400 W PDB: 1FOI
[c]iNOS L-arginine PDB: 1NSI; 1400 W PDB: 1QW5
[d]nNOS L-arginine PDB: 4D1N; 1400 W PDB: 1QWC Synthesis and Characterization of Compound 5

The four-step synthesis of 5 was carried out with a favorable overall yield of 52.5% as shown in Scheme 1 (FIG. 2). The intermediates allow for multiple points of derivatization for the synthesis of a focused library. Due to the instability of some intermediates, namely the brominated 2 and nitrone 5, reactions were carried out under an argon atmosphere, and products were stored at −20° C. Activation of the boc-protected benzyl alcohol 1 allows for substitution with tert-butyl amine (3), then further de-protection permits substitution with an amidine (4). These two steps can be used for further derivatization to modulate activity of the nitrone and NOS-inhibitor aspects of the molecule, respectively. The final step is oxidation of the secondary amine to the nitrone 5 by $NaWO_4$—$H_2O_2$. While no oxidation of the amidine was observed, other intermediates may be sensitive to this oxidation step. Analysis by and $^{13}$C NMR, HRMS, and HPLC-PDA showed the successful synthesis of 5 at >95% purity.

The separation of 2 was first carried out using a manual column, and afforded 83% yield, however switching to flash chromatography separation increased the recovery to a 91.2% yield. The SN2 reaction of 2 with tert-butylamine was then carried out at room temperature in the presence of $K_2CO_3$. It was observed that adding 2 in DMF dropwise to a stirring solution of tert-butylamine and $K_2CO_3$ resulted in higher yield of 3 (96.4%) than if tert-butylamine was added dropwise to 2 followed by addition of $K_2CO_3$ (84%). The synthesis of 4 from 3 was performed in two steps: the de-protection of the boc-protected amine by trifluoroacetic acid, followed by formation of the amidine through an SN2 reaction with ethylacetimidate. 4 was isolated after lyophilization of the ether and EtOAc-washed aqueous layer, as a highly hygroscopic, sticky solid that was insoluble in chloroform and acetone. The formation of the nitrone 5 from oxidation of 4 by $NaWO_4$—$H_2O_2$ was first attempted at 0° C. over 2 hours. This resulted in negligible formation of 5 that was not recovered. Upon increasing both the reaction temperature (0° C. to rt) and the time (2 hr to 12 hr), coupled with more vigorous stirring, 5 was formed at 66.2% yield. Normal phase separation by flash chromatography required high polarity (~18% MeOH in $CH_2Cl_2$) to elute 5, which indicates that derivative compounds that are more polar than 5 should be purified by a different method.

FIGS. 7-10 show NMR, $^{13}$C NMR, HPLC-PDA purity, and LRMS characterization of the prepared compounds 2-5. Specifically, FIGS. 7A-7D show characterization of compound 2, FIGS. 8A-8D show characterization of compound 3, FIGS. 9A-9D show characterization of compound 4, and FIGS. 10A-10D show characterization of compound 5.

5 EPR Spin Trapping and Formation of 6

Figure 11A:
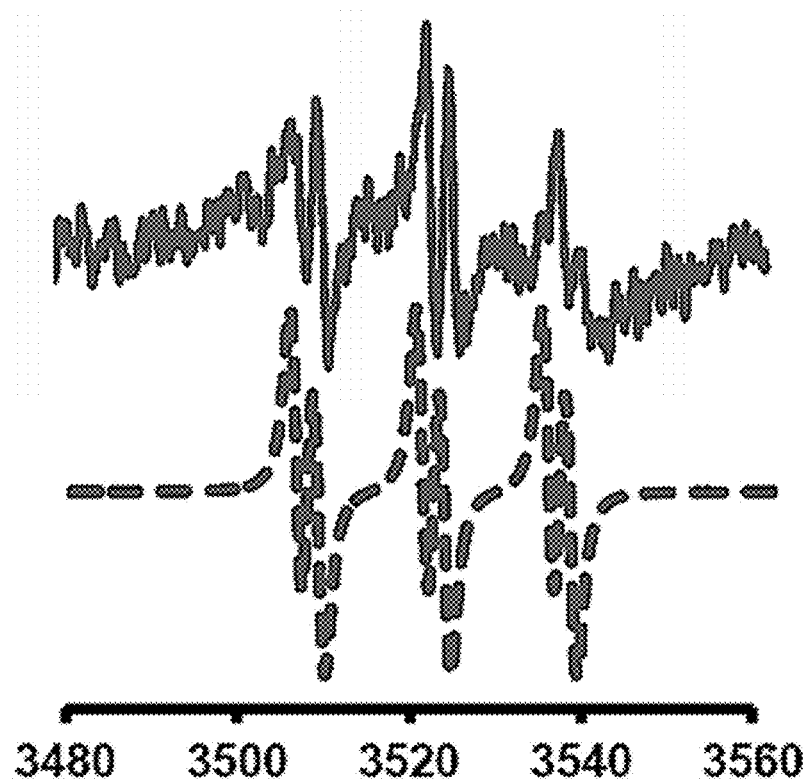
FIGS. 11A-11F: X-Band EPR spectra and simulations of 5 (35 mM) in the presence of $O_2.^-/HO_2.$ ($KO_2$ in 20% PBS/DMSO; $HO_2$. ad-duct, aN: 14.19, aHβ: 2.48; aHγ: 0.52) (FIG. 11A), .OH/.$CH_3$ ($Fe_2^+/H_2O_2$ in 30% PBS/ DMSO; OH adduct, aN: 15.56, aHβ: 3.24; aHγ: 0.61, [30.6%]; $CH_3$ adduct, aN: 14.24, aHβ: 2.41, [69.4%]) (FIG. 11B), and ONOO$^-$/HCl (10 mM, pH-6 in 30% PBS/DMSO; nitroxyl, aN: 12.80) (FIG. 11C).
Figure 11B:
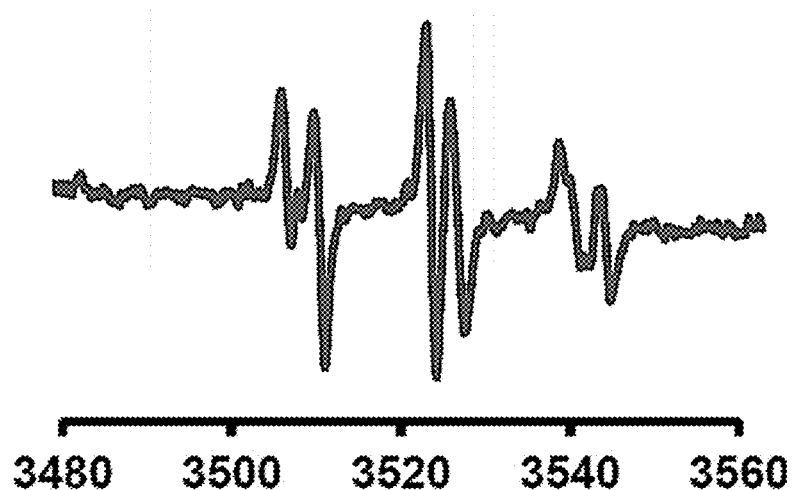
Figure 11C:
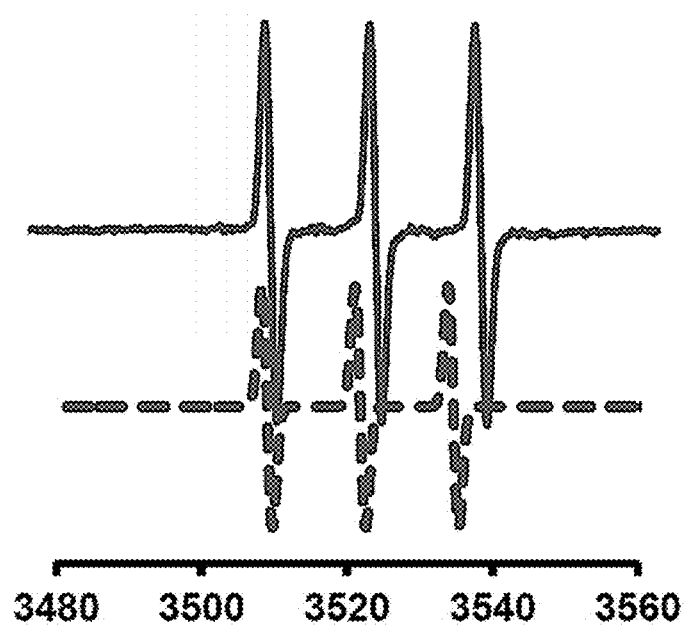
Figure 11D:
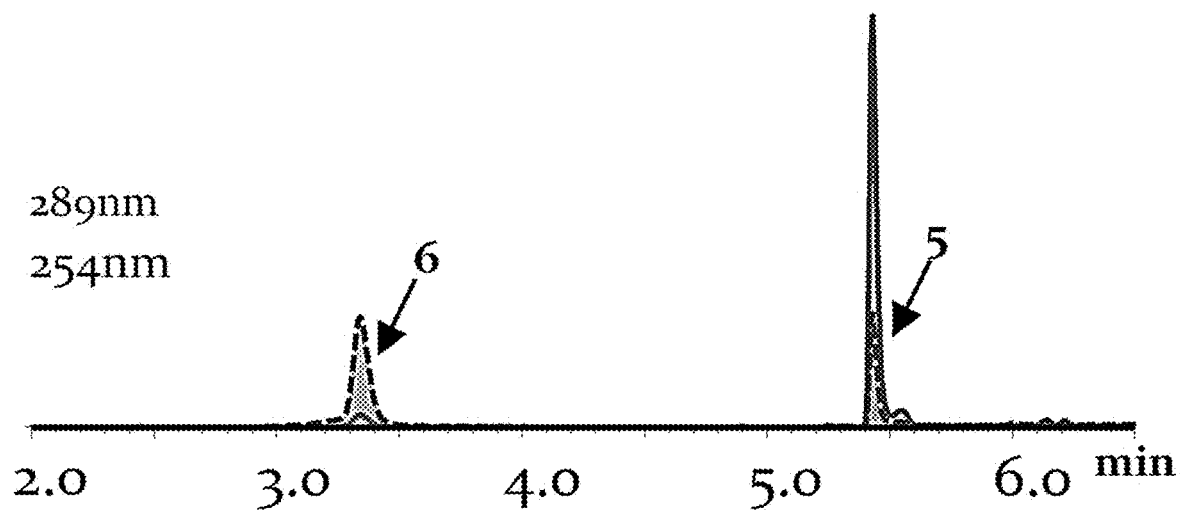
Figure 11E:
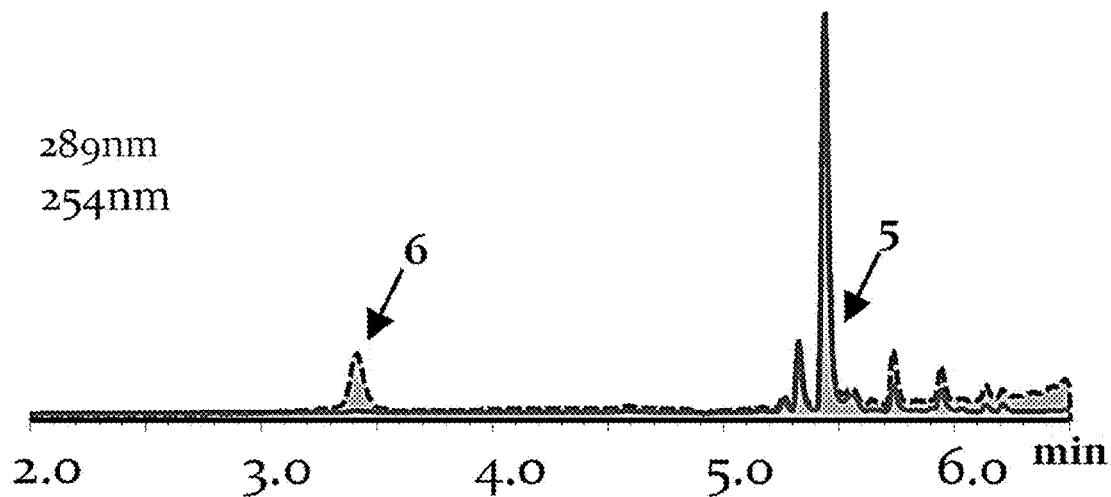
Figure 11F:
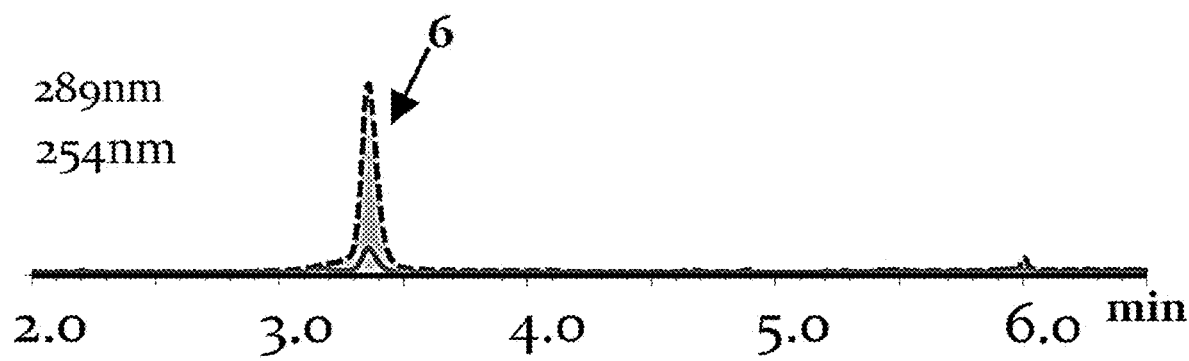

EPR characterization of radical adducts of 5 were carried out using conventional ROS systems. Spectra for PBN were obtained using the same systems, and matched previous observations. Resulting EPR spectra from addition of 5 to $O_2.^-/HO_2.$, .OH/.$CH_3$, and $ONOO^-/HCl$ systems are shown in FIGS. 11A-11C. Solutions of $O_2.^-$ and .OH generated oxygen and carbon-centered radicals whose spectra closely resemble that of PBN. 5 was observed to spin trap $O_2.^-/HO_2.$, .OH, and .$CH_3$ to yield EPR spectra that strongly resemble those of PBN. The amidine moiety is outside of EPR coupling range, so the substitution has a small influence in the hfsc's observed for 5 compared to the 'unsubstituted' PBN.

There was no observable difference in signal intensity between 5 and PBN, which indicates a similar reactivity, and is in agreement with the in silico ΔG calculations above. Interestingly, an identical three-line EPR signal was observed for both 5 and PBN in the presence of $ONOO^-/HCl$ (no signal was observed for nitrone or $ONOO^-/HCl$ alone). Due to the absence of Hβ splitting, this spectra is believed to pertain to a tert-butyl nitroso formed after nitronyl N—C bond cleavage. Previous EPR studies with PBN and $ONOO^-$ have been performed, but no direct detection of free radicals have been observed, instead incidental radicals formed from proteins, uric acid, or dihydropyridines were used for characterization. In this example, however, addition of $ONOO^-$ to 5 or PBN resulted in the same three-line EPR spectra with a much larger signal intensity than that of the two other radical systems. A similar three-line spectra has been observed from PBN hydrolysis to form a tert-butyl nitroso, 2-methyl-2-nitrosopropane (MNP) in the presence of Amyloid-β, which was believed to be due to $H_2O_2$ oxidation of PBN to cause hydrolysis, followed by further oxidation of MNP. ONOOH exists as a bi-radical, which is capable of oxidizing the nitrone to cause hydrolysis, then further oxidizing the tert-butyl nitroso to yield an EPR-detectable species. Importantly, this species would give the same hfsc's for 5 as for PBN, which would correlate to the observed spectra. The in silico prediction of a 5-O— or 5-OH adduct from the reaction with $ONOO^-/ONOOH$ was not observed by EPR, however such an adduct would yield hfsc's similar to that of the $Fe_2^+/H_2O_2$ system. This indicates that either the 5-O— adduct is highly unstable, and converts very rapidly to the aldehyde species, or that $ONOO^-/ONOOH$ causes a non-radical decomposition of PBN and 5 to then allow the formation of a tert-butyl nitroso radical by oxidation.

The formation of benzaldehyde from the decomposition of PBN in the presence of free radicals has been shown. To demonstrate that this mechanism was conserved for the nitrone 5, the EPR systems described above were analyzed by HPLC-PDA to confirm the formation of benzaldehyde from PBN, then the molecule 6 from 5. Multiple free radicals are known to be formed under ischemic and ischemia/reperfusion conditions, making it important to ensure that 6 is formed from 5 for each radical species to ensure its activation at the desired site. Benzaldehyde was formed from PBN in significant quantities for each of the $O_2.^-/HO_2.$, $Fe_2^+/H_2O_2$, and $ONOO^-/HCl$ systems. These systems were attempted to be analyzed by LC-MS/MS, however, due to the difficulty of ionizing benzaldehyde for detection, such experiments did not produce meaningful data. After PBN decomposition was confirmed, the EPR solutions of 5 were analyzed by HPLC-PDA to observe the formation of a new peak at 3.35 min for each system, a dramatic shift from 5 (pure 5 RT=5.43 min). This shift in RT was accompanied by a change in λmax, from 289 nm for 5, to 249 nm for the new peak. The shift in λmax correlates with PBN decomposition, as the nitronyl bond is cleaved. While benzaldehyde exhibits an increase in RT from PBN due to its more-non-polar nature, the decomposition of 5 to 6 would cause an increase in hydrophilic character, such as that seen in the synthetic precursor, 4. This new peak was observed to be the only peak in the 5-$ONOO^-/HCl$ system, mirroring that of PBN—$ONOO^-/HCl$. LC-MS/MS analysis of this solution produced a strong signal corresponding to the molecular weight of 6. Using this to create an LC-MS/MS MRM analysis method, the same compound was observed in the other radical systems as well. Taken together, these data strongly indicate the formation of 6 after reaction of 5 with physiologically relevant free radicals. This method may also be used for rapid screening of derivative compounds to confirm they exhibit a pro-drug character before proceeding to in vitro assays.

Figure 12:
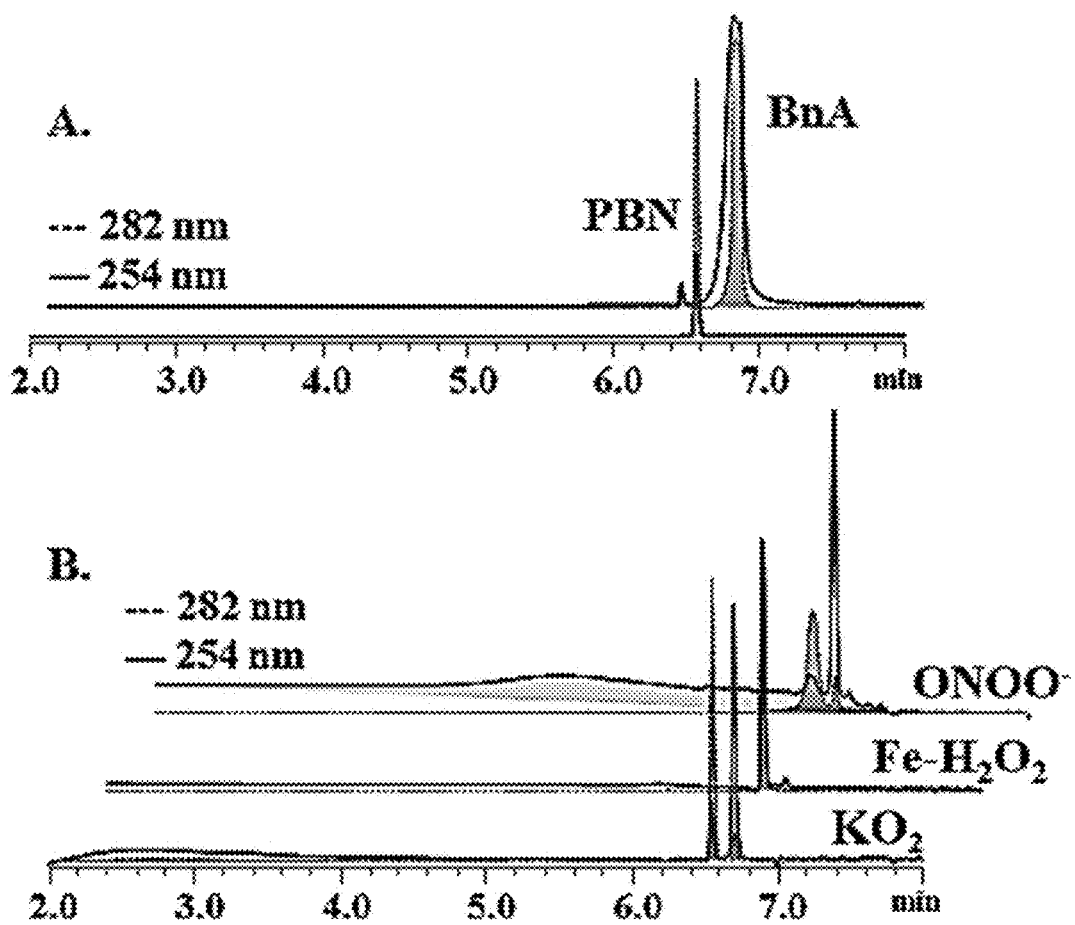
FIG. 12: HPLC-PDA analysis of free radical reactions with PBN and 5. (A) HPLC chromatograms of PBN (RT=6.50 min) and benzaldehyde (BnA; RT=6.65 min). (B) Chromatograms of PBN incubated with the incubated radical system for 24 hr. Significant BnA formation was observed for $KO_2$ and ONOO$^-$ systems, with minor formation in the Fe—$H_2O_2$ system. (C) HPLC chromatograms of 5 (RT=5.40 min) and 6 (RT=3.36 min). (D) Chromatograms of 5 incubated with the incubated radical system for 24 hr. Minor 6 formation in the Fe—$H_2O_2$ system, and significant 6 formation was observed for $KO_2$ and ONOO$^-$ systems with no observed 5 remaining in the ONOO$^-$ system.
Figure 12:
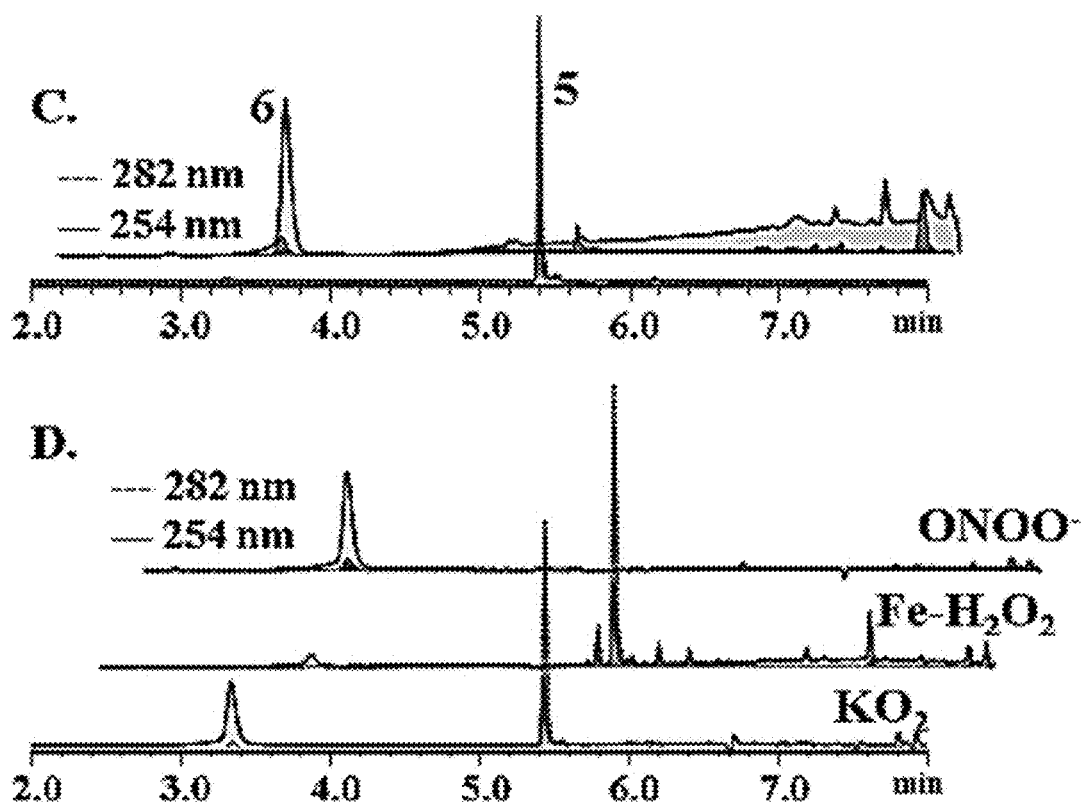

Solutions of the 5-ROS systems used to acquire EPR spectra were replicated, and allowed to incubate at 37° C. for 24 hr before analysis by HPLC-PDA at 254 nm. (FIG. 12.) A new peak at 3.4 min was observed for each of the three radical systems tested (5 RT=5.4 min). This more-polar compound was formed in varying amounts for each system, and was found to be the only peak in the 5-$ONOO^-/HCl$ system. Additionally, the λmax of the new peak was lower than that of 5 (249 nm vs 289 nm), indicating a loss of conjugation likely due to nitronyl N=C modification or cleavage. Low-resolution LC-MS/MS was performed on the 5-$ONOO^-/HCl$ solution, and found a strong signal of an m/z matching the predicted mass of the aldehyde 6 (M+H=177; M+NH4=195; M+K=215). This m/z was used to create an MRM analysis by fragmentation. LC-MS/MS analysis of the other 5-ROS solutions using this MRM showed the presence of 6 in each. The ROS systems were also replicated with PBN, and the formation of benzaldehyde was similarly observed. These data demonstrate the ability of 5 to trap ROS and decompose to the putative NOS inhibitor 6.

Confirmation of 6 Formation

EPR, HPLC-PDA, and LC-MS/MS analysis of the 5-radical systems show the formation of a more-polar compound with a molecular weight matching that predicted for 6. However, this system yielded too little 6 for isolation and structural characterization. The conditions for the 5-ONOO$^-$/HCl system were replicated and scaled up after it was found that simply adding ONOO$^-$ to 5 in ddH$_2$O did not yield 6. This change in reactivity is likely due to the strongly basic solution ONOO$^-$ (0.3 M NaOH), which would not allow protonation to the more reactive ONOOH (pKa=6.8). Upon using PBS and HCl to lower the pH to 6, ONOO$^-$ addition was found to decompose nearly all of 5 to 6 as observed by HPLC-PDA. Isolation of 6 from the aqueous solution allowed acquisition of $^1$H-NMR to observe a peak at 10.0 ppm that confirms the formation of a benzaldehyde while retaining the amidine moiety. The isolation of 6 from the aqueous salt solution was non-trivial due to its high polarity. The $^1$H-NMR confirms that 6 is being formed from free-radical reactions with 5, and confirms that the LC-MS/MS MRM analysis method for 6 is accurate for the monitoring of 5:6 levels in vitro and in vivo.

Isolation and Characterization of 6

Figure 13:
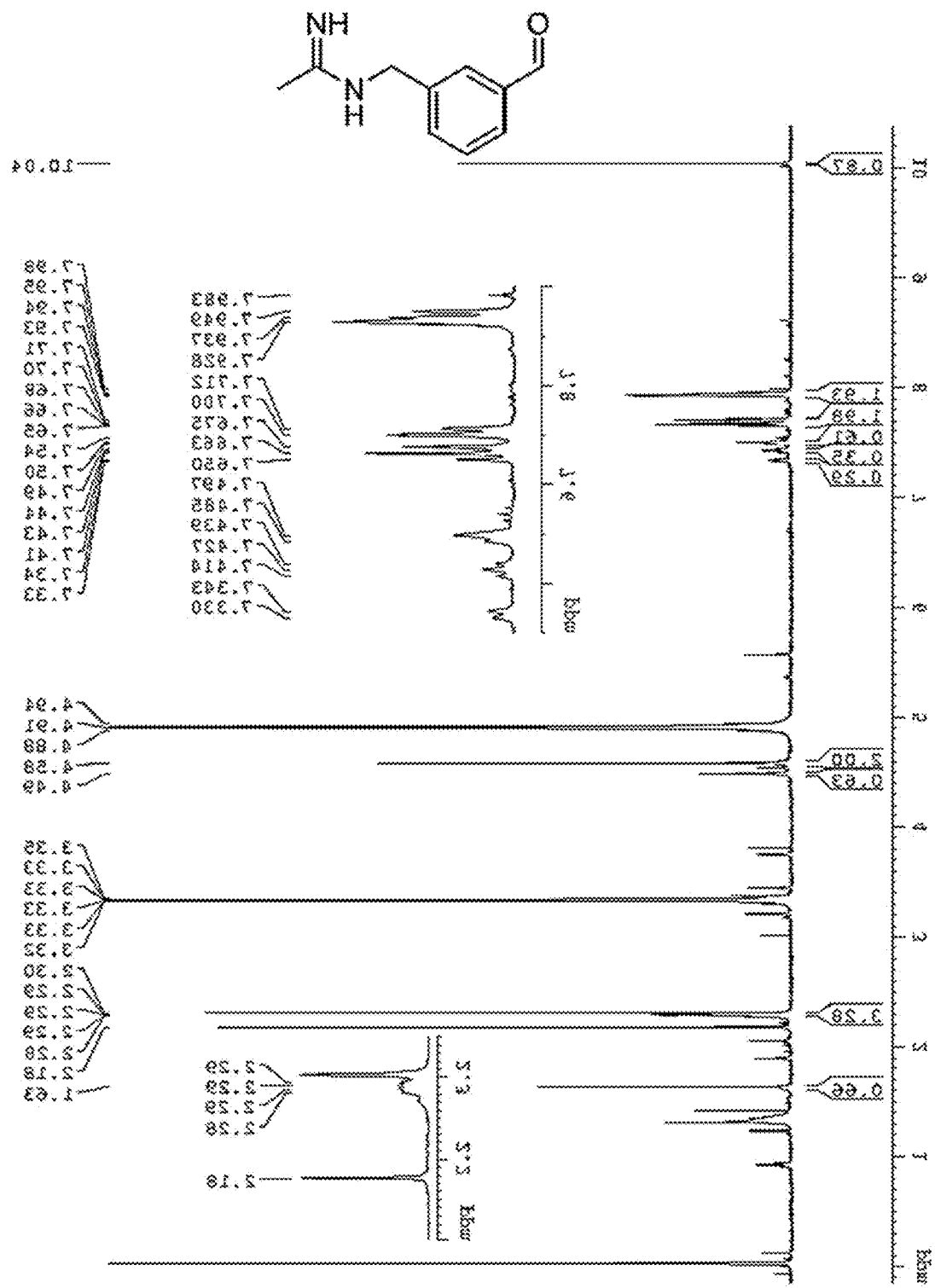
FIG. 13: $^1$H-NMR ($CD_3OD$, 400 MHz) of 6 isolated from the 5-ONOO$^-$/HCl system. The peak at δ 10.04 (1H, s) is characteristic of a benzaldehyde.

The 5-ONOO$^-$/HCl system was mimicked at a larger scale to produce sufficient quantity of 6 for isolation and characterization. Interestingly, 0.50 eq of ONOO$^-$ was enough to convert nearly all 5 to 6 as observed by HPLC-PDA (95.4%) after one hour. pH was observed to be critical to this reaction; it was initially attempted in dH$_2$O without the addition of HCl for the ease of purification, but this resulted in no observable 6 formation, and the products formed that were not identified. The 5-ONOO$^-$/HCl reaction was extracted with CH$_2$Cl$_2$, and then the aqueous fraction was lyophilized to give a white solid containing 6 and various salts. Addition of ACN to this solid followed by filtration allowed the insoluble salts to be removed, and 6 isolated. $^1$H NMR in CD$_3$OD showed the absence of the nitronyl-Hβ and tert-butyl group, and a new peak at 10.0 ppm which is characteristic of a benzaldehyde (FIG. 13). LC-MS/MS analysis of the isolated 6 yielded the same parent mass and fragmentation pattern as was previously found for 5-ONOO$^-$/HCl.

In Vitro Neuroprotective and Anti-Inflammatory Properties of 5

Figure 15A:
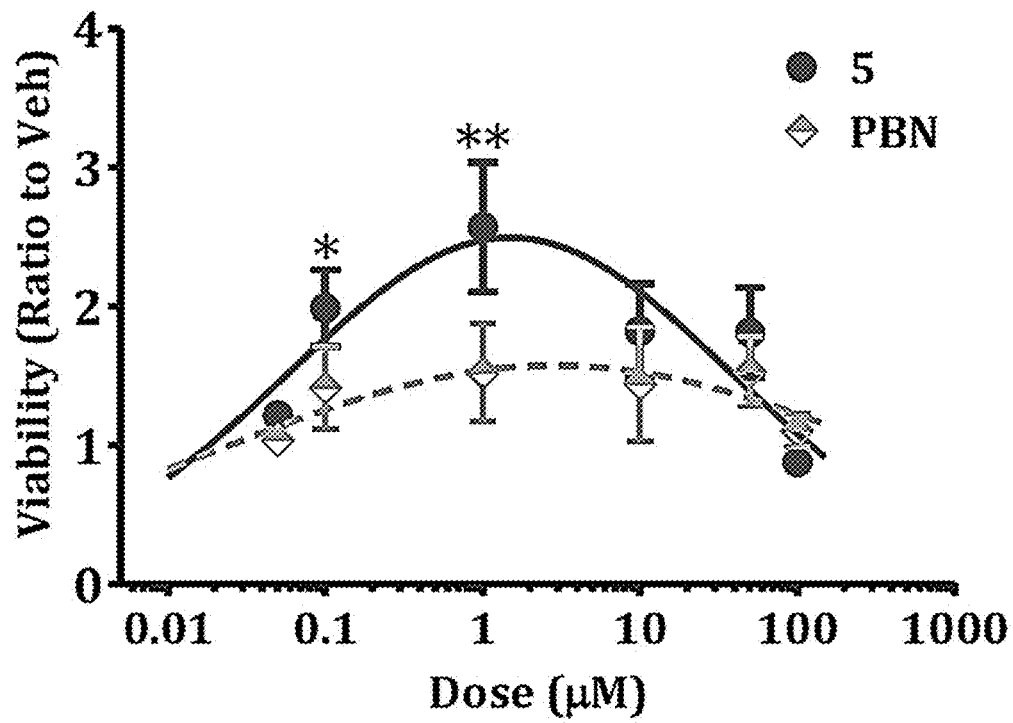
FIGS. 15A-15F: In vitro dose-response plot of SH-SY5Y viability after oxygen-glucose deprivation (OGD) and 24 hr treatment relative to vehicle control. 5 showed the highest neuroprotection at 1.0 µM, which was significantly higher than that of 1.0 µM PBN (n=6, p<0.05).
Figure 15B:
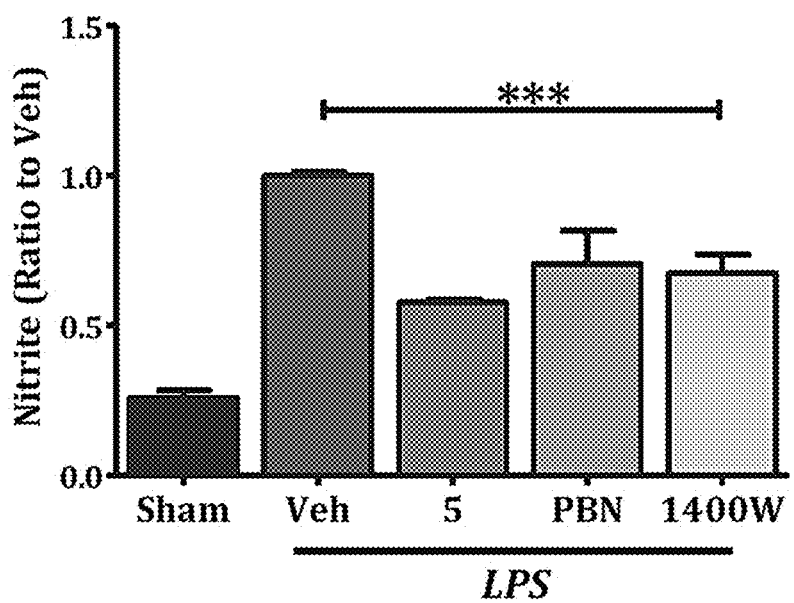

5 was tested in an in vitro model of neuronal ischemia/reperfusion, oxygen-glucose deprivation (OGD), to assess its neuroprotective potential. A dose-finding study was first performed to determine the optimal concentration. SH-SY5Y cells exposed to 1.5 hr OGD treated with 5 or PBN (0.05 μM to 100 μM) were assayed for viability and plotted as ratio to vehicle control (FIG. 15A). A bi-phasic trend was observed for 5 treatment, with increasing viability from 0.1 μM to 1.0 μM (1.21 to 2.57 times greater than vehicle; p<0.05, p<0.01 respectively), giving way a decline to baseline at 100 μM. PBN trended in a similar fashion, but did not approach significance at any concentration tested. Additionally, 1.0 μM 5 showed significantly greater neuroprotection than PBN at the same dose (p<0.05). 1.0 μM was thus determined to be the optimal dose of 5, and was used in further in vitro studies.

The mechanisms into the neuroprotection afforded by 5 were investigated by Western blotting. SH-SY5Y cells subjected to OGD and treated with 1.0 μM 5 showed a dramatically increased phospho-Akt/total Akt ratio (4.1 times higher, p<0.05). This increase was also observed for PBN, and the combination of PBN and 1400W (1.0 uM), albeit each to a lesser extent than 5 alone. Treatment with 5 also showed a reduction in OGD-induced protein nitration. 3-Nitrotyrosine (3-NT), formed due to direct nitration of protein tyrosines by ONOO$^-$, was increased by OGD 1.5-fold in vehicle groups, and ameliorated by 48% upon treatment with 5 (p<0.01). Similarly, the pro-apoptotic cleavage of caspase-3 was induced by OGD, but was significantly reduced with 5-treatment compared to vehicle (47% reduction, p<0.01).

Figure 14:
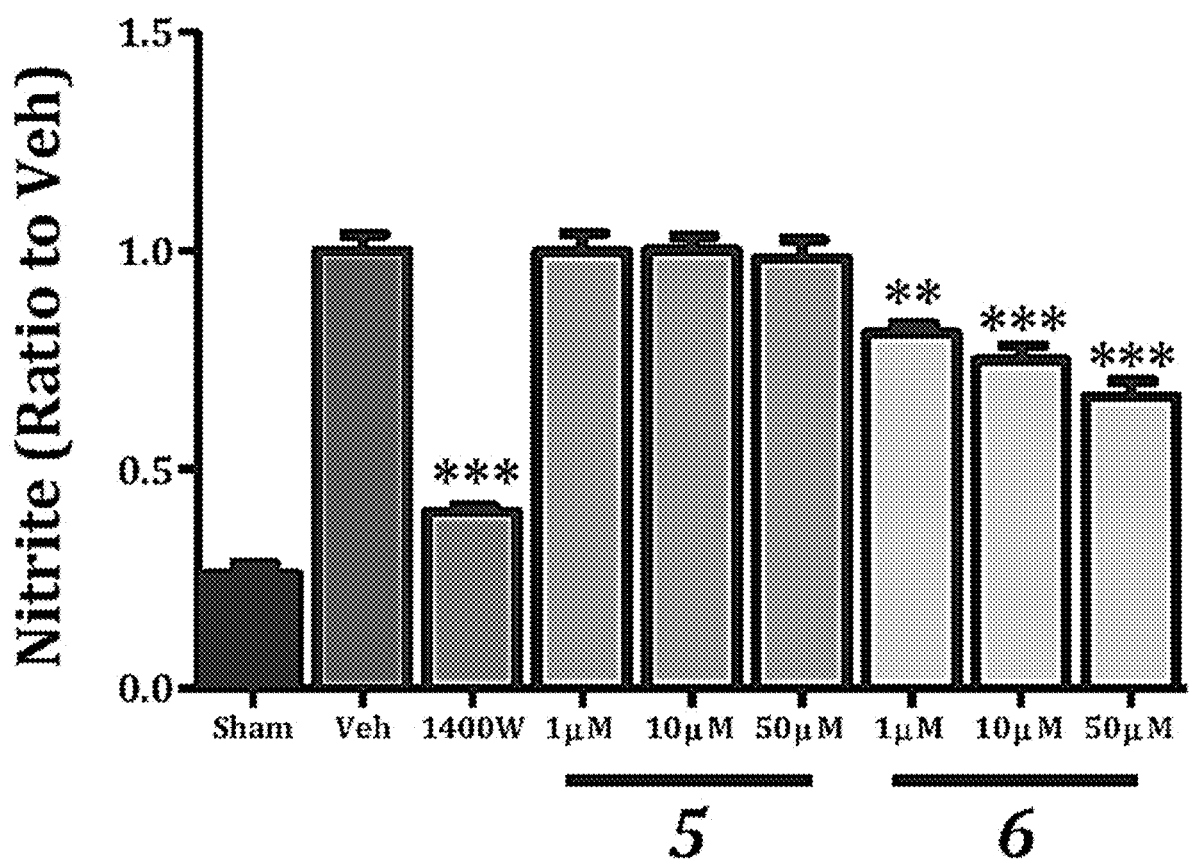
FIG. 14: Griess assay of LPS-stimulated SIM-A9 cells following 24 hr treatment indicates anti-inflammatory ability for 6 and 1400W, but not 5 (n=6). 6 treatment, but not 5 treatment, decreased nitrite in a dose-dependent manner which indicates iNOS inhibition. Data represented as mean±SEM, p<0.01, and *p<0.001, from vehicle control, One-way ANOVA followed by Newman-Keuls post-hoc test.

Microglia express iNOS and convert to an inflammatory phenotype upon stimulation with LPS. Both PBN and 1400W have been previously shown to exhibit anti-inflammatory properties. To investigate the anti-inflammatory potential of 5, SIM-A9 microglia were stimulated with LPS (100 ng/mL), and treated with vehicle or drug for 24 hr. Nitrite, as measured by Griess assay, was increased as expected after LPS, but this was attenuated with each of 5, PBN, and 1400W at 1.0 μM (p<0.001). (FIG. 14.) 5 was not observed to lower NO production at concentrations as high as 50 μM, although the highest dose appeared to cause a slight decrease. Doses from 1.0 μM to 50 μM of 6 exhibited a dose-dependent decrease in nitrite (from a ~19% to −33% decrease, p<0.01 and p<0.001, respectively). PBN was not observed to cause a reduction in nitrate at the same concentrations. This indirect measurement of NO production indicates a reduction in iNOS activity due to 6 treatment but not 5, which indicates that 5 needs to be converted to 6 to allow iNOS inhibition.

OGD-Induced Formation and Localization of 6 from 5

Figure 16:
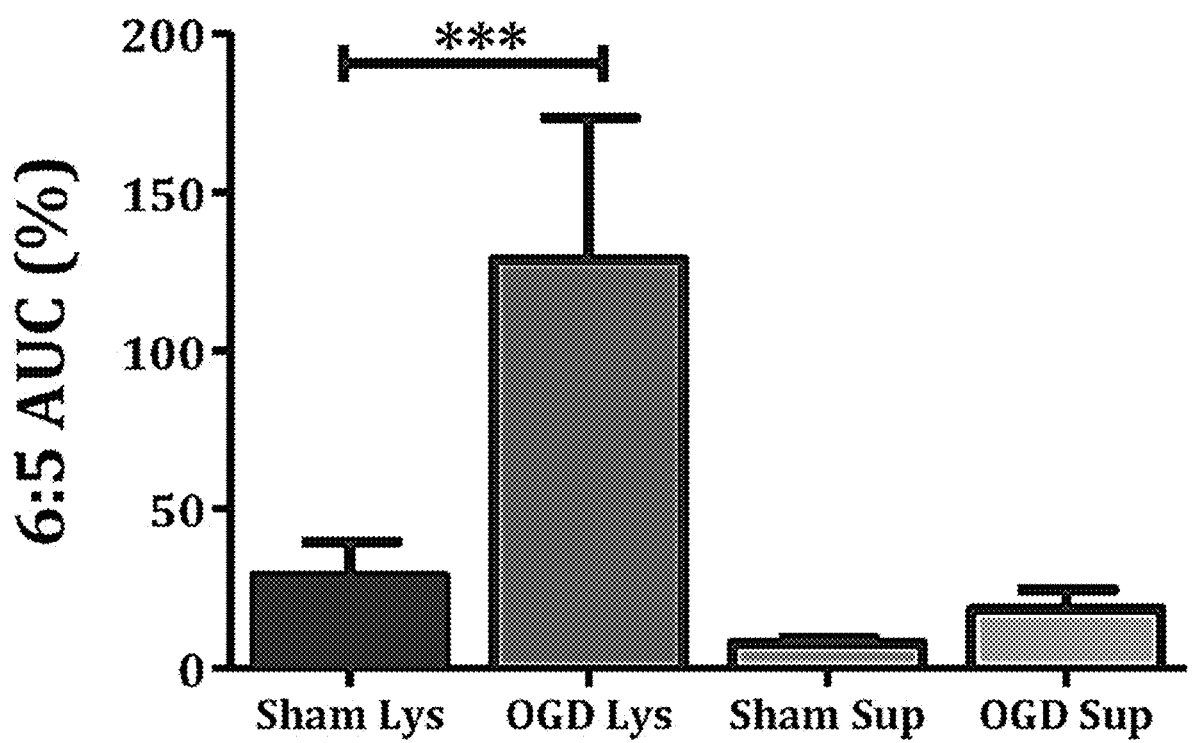
FIG. 16: Levels of 6 with respect to intra-run 5 in supernatant and lysate fractions of sham and OGD-exposed SH-SY5Y cells treated with 5 as measured by LC-MS/MS. 6 was observed to be formed at comparable levels in the supernatant, but at considerably higher levels in the lysate of OGD-exposed cells compared to sham cells. AUC normalized between samples with IBA internal standard. Data represented as mean±SEM, n=3-6, ***p<0.001, from respective sham control, One-way ANOVA followed by Newman-Keuls post-hoc test.

5 was observed to be converted to 6 in situ in the presence of oxygen-centered free radicals as measured by EPR and HPLC-PDA. This decomposition occurs in vitro; 6 is formed at higher levels in cells exposed to ischemia/reperfusion conditions. SH-SY5Y cells exposed to OGD and treated for 24 hr with 10 μM 5 as before were used to measure the extracellular and intracellular formation of 6. Medium of sham and OGD-exposed, 5-treated cells and their respective cell lysates were worked up and analyzed by LC-MS/MS using the MRM methods developed previously. The AUC for 6 was normalized between samples by the internal standard, then divided by the intra-run AUC for 5 to express levels of 6 as a ratio of 5 (FIG. 16). The supernatant fractions were found to have comparable ratios of 6:5 for both sham and OGD-exposed cells. 6 was found to be formed in considerably higher levels in the intracellular fractions of OGD-exposed cells compared to sham cells (129% and 29% 6:5 AUC, respectively, p<0.001). Due to its high polarity, 6 may be formed by intracellular ROS from 5, but not be able to diffuse out, leading to localization within ROS-stressed cells. These data indicate that 5 is cell permeable, and that 6 is preferentially formed in cells undergoing ischemia. Taken together, the in vitro data show that 5 is a cell permeable, neuroprotective nitrone that forms the anti-inflammatory 6 upon ischemia/reperfusion. This neuroprotection is believed to be due to its upregulation of pAkt, and decrease of 3-NT and cleaved Caspase-3 levels.

Effect of 5 on Cerebral Blood Flow (CBF)

Figure 17A:
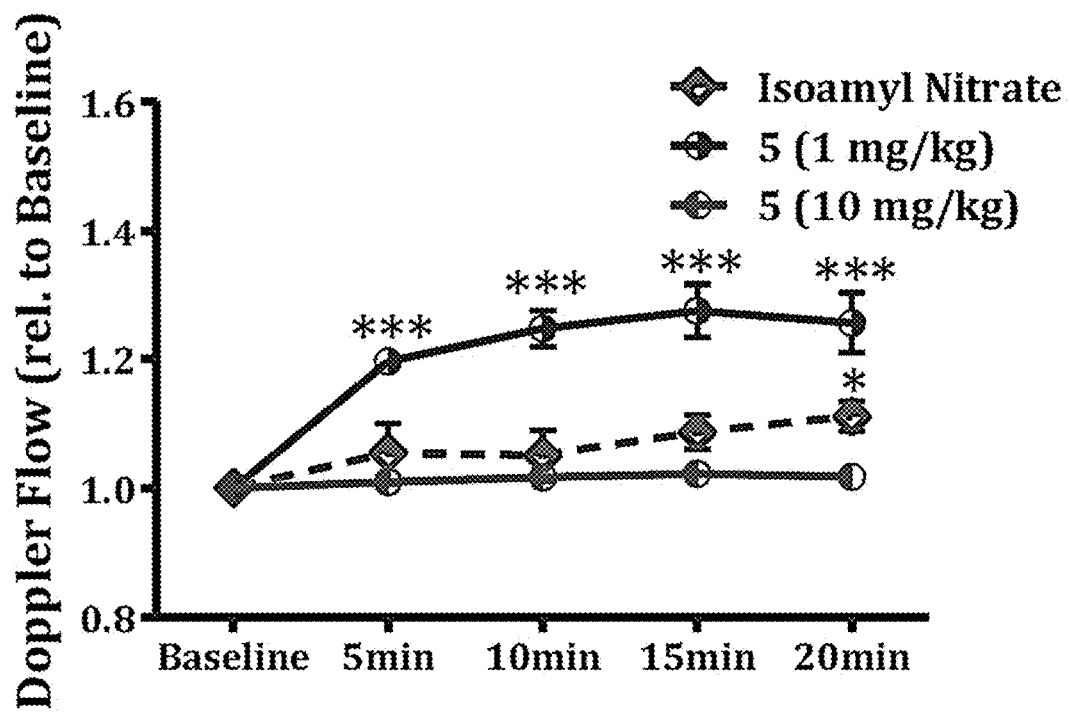
FIGS. 17A-17F: Doppler CBF measurement after intravenous injection of isoamyl nitrate or 5 to anesthetized mice over 20 minutes relative to baseline.
Figure 17B:
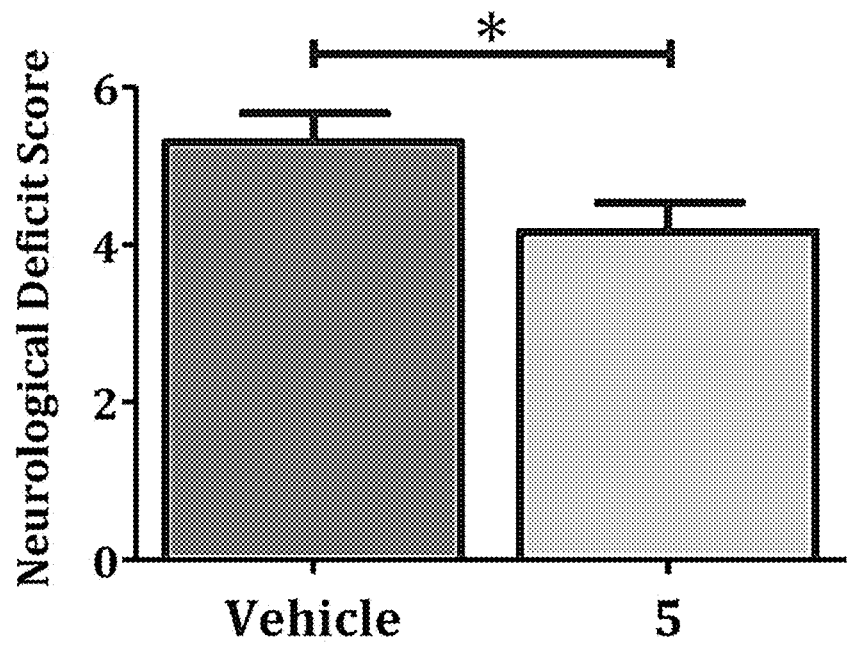
Figure 17C:
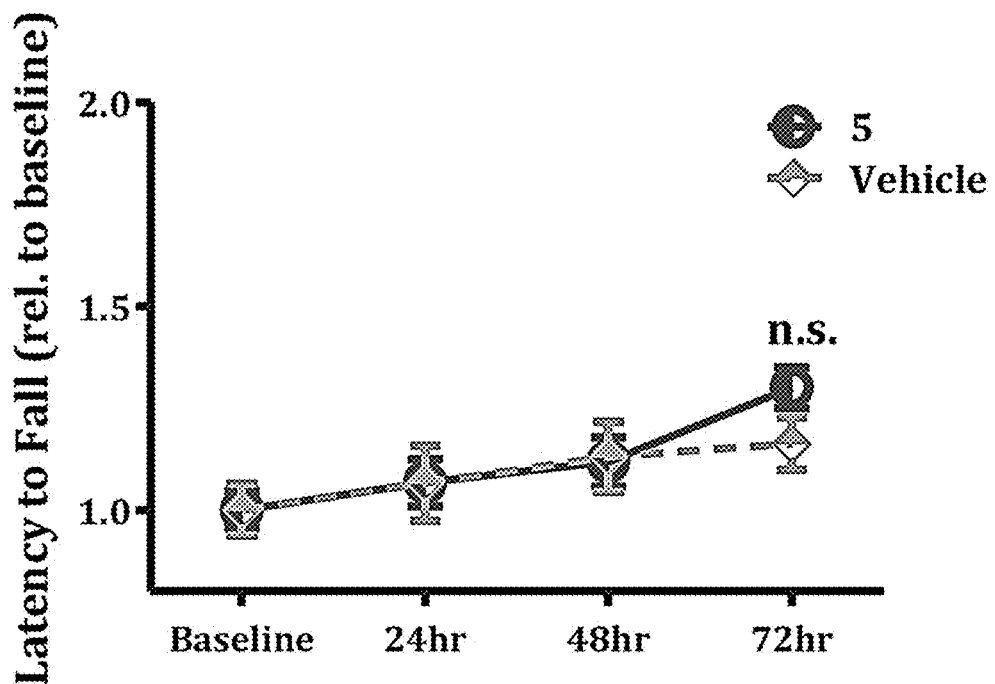
Figure 17D:
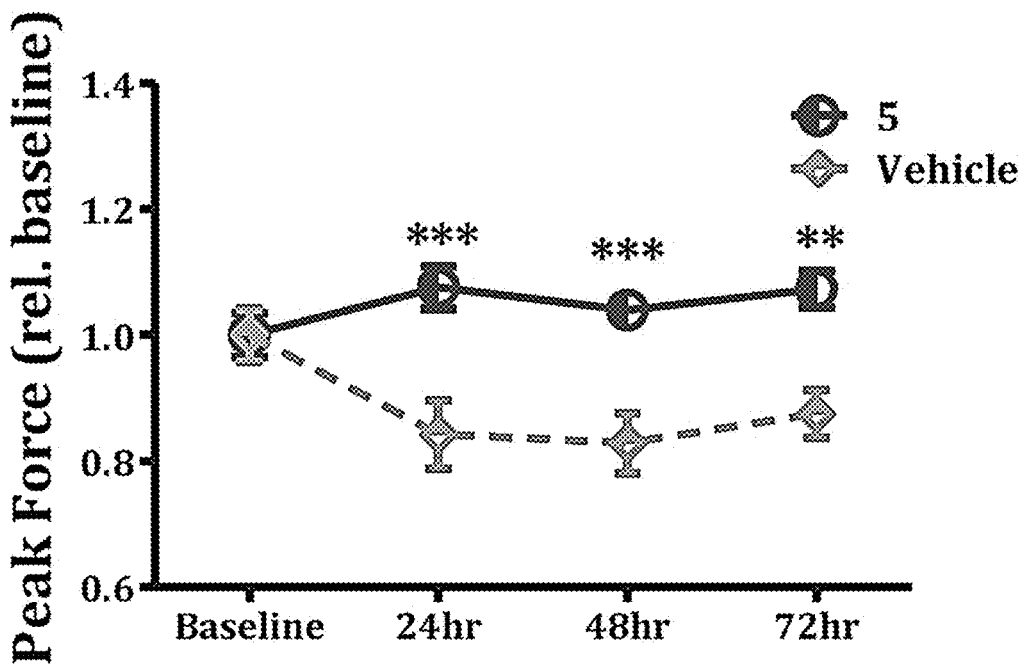

Due to the complex interplay of O$_2$.-scavenging, NO donation, and NOS inhibition, the effects of 5 on CBF were investigated. CBF correction in acute ischemic stroke has a strong correlation with positive patient outcome, and is an often overlooked aspect of neuroprotective therapies. Doppler flowmetry measurement over the middle cerebral artery (MCA) for 20 min after intravenous administration was performed on anesthetized, C57BL/6 mice. Doppler flowmetry measures the Doppler shift of a laser positioned over a blood vessel caused by the movement of vascular red blood cells. A known vasodilator, isoamyl nitrate, was found to increase CBF over 20 min (111%±4.0% baseline, p<0.05). Paradoxically, the lower dose of 5 (1 mg/kg) caused a significant increase in CBF (126%±4.6% baseline, p<0.001), while a higher dose (10 mg/kg) produced baseline readings (102%±0.7% base-line, FIG. 17A). Compared to isoamyl nitrate, the low dose of 5 increased CBF at an earlier time point (20 min and 5 min, respectively). Plasma and brain samples collected immediately after sacrifice (25 min from drug administration) and analyzed by LC-MS/MS confirmed that the animals in the higher-dose group were exposed to larger doses of 5 in plasma (1,681±881 nM for 10 mg/kg; 171.7±51.8 nM for 1 mg/kg) and brain (17.97±2.23 nM for 10 mg/kg; 6.41±2.03 nM for 1 mg/kg). A similar effect was previously observed where administration of the NOS-inhibitor L-NAME abrogated an increase in MCA blood flow after PBN administration in rats.

The average brain:plasma ratio after 25 min for the two treatments of 5 was found to be 0.029±0.010 (n=6). The decomposition product 6 was detected by LC-MS/MS using the MRM method attained previously, and was observed to be present at higher levels in the brain than plasma (24.5%±0.1% and 12.7%±0.2%, respectively, expressed as percent of 5 AUC within the same run, n=6).

In Vivo Neuroprotection in a Murine Model of Permanent Ischemia

After exploring the effects of chosen doses of 5 on CBF, the neuroprotective effects of 5 were explored in a whole animal model of acute permanent ischemia. Wild-type, male C57BL/6 mice were subjected to permanent MCA occlusion (pMCAO) followed by a bi-phasic dosing regimen of 5 to assess in vivo neuroprotection and effects on neurobehavioral parameters. Vehicle (n=10) or 5 (10 mg/kg in normal saline, n=12) were administered intravenously by lateral tail vein injection at 3 and 6 hr after pMCAO followed by 1 mg/kg 5 twice daily separated by 8 hr thereafter. Both doses were well tolerated, and there were no observed adverse effects at any time point. Animals were trained on neurobehavioral assessments for 3 days prior to surgery, then were tested at 24, 48, and 72 hr post-ischemia.

No effect on rota rod performance was observed for both treatment groups, which remained near baseline levels after ischemia through 72 hr (FIGS. 17A-17F). 5 treatment trended toward an increase in rotarod performance at 72 hr from vehicle, however this was not statistically significant. Vehicle treated animals showed a decline in forelimb grip strength after pMCAO, while the 5-treated group did not exhibit a post-surgical decline, and obtained higher readings than vehicle treated animals at each time point. Neurological deficit scoring (NDS), an optimized 28-point system, was conducted prior to sacrifice at 72 hr, in which 5-treated animals showed a less-severe deficit than vehicle treated animals (4.2±0.4 and 5.3±0.4, respectively, p<0.05, unpaired t-test). 5-treated animals showed a less-severe deficit than vehicle treated animals (4.2±0.4 and 5.3±0.4, respectively, p<0.05, unpaired t-test). Thus, 5 treatment moderately ameliorated neurobehavioral deficits induced by permanent ischemia while showing good tolerability and no adverse effects for acute administration.

Figure 17E:
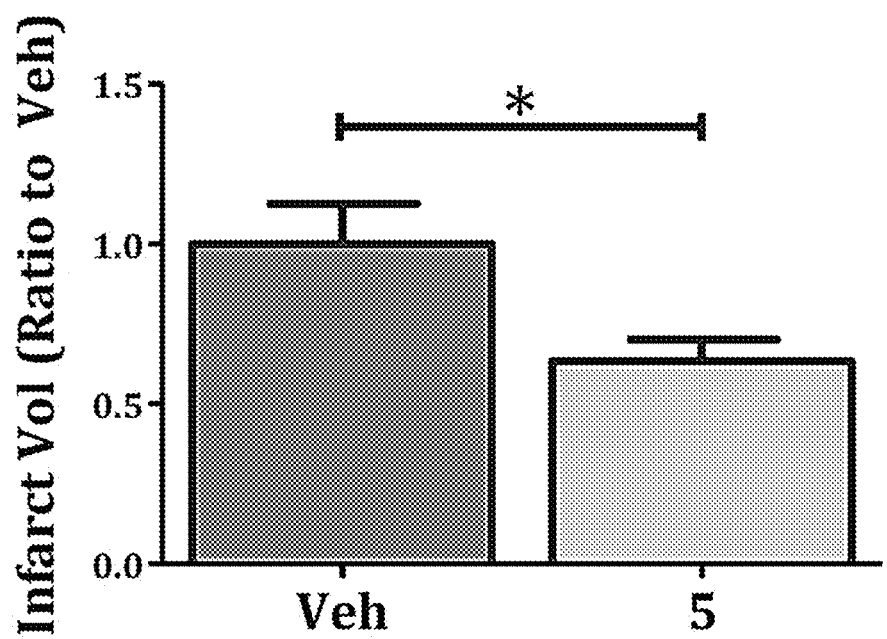
Figure 17F:
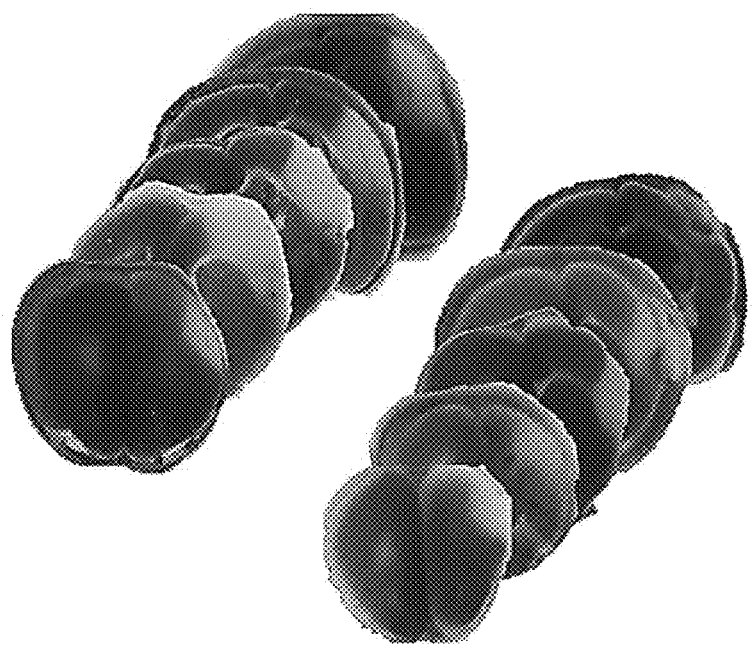

Animals from both groups were sacrificed by $CO_2$ 72 hr post-pMCAO (4 hr from the last dose), brains were rapidly harvested, sectioned into 2-mm thick coronal slices, and stained by 2,3,5-Triphenyl-tetrazolium chloride (TTC) in normal saline to visualize the infarct area (FIGS. 17E-17F). TTC stains viable tissue red, while leaving the dead tissue of the ischemic core and penumbra white. Sections were quickly imaged, and infarct volume was determined by the ratio of unstained tissue in the ipsilateral cortex to the total contralateral area. Mice treated with 5 were found to have a 37% decrease in infarct volume compared to vehicle animals (p<0.05, unpaired t-test). In 5-treated mice, the dead tissue in the penumbra was observed to be reduced in volume compared to vehicle controls despite a similar ischemic core. Analogous to the conversion of 5 to 6 in OGD-treated cells in vitro, 5 is decomposed in the penumbra and ischemic areas in larger amounts than in the contralateral areas or periphery, resulting in the observed efficacy.

Figure 18:
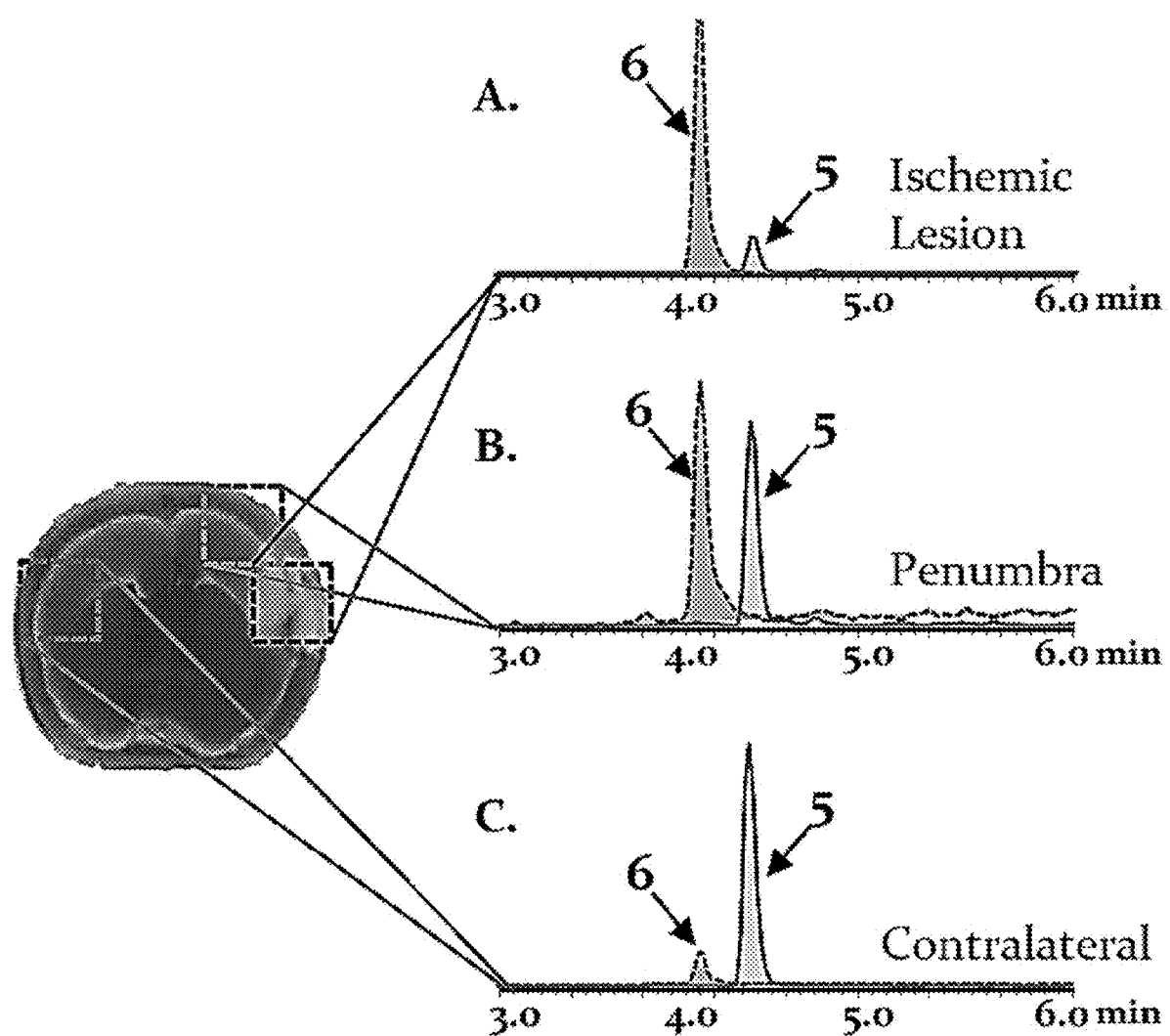
FIG. 18: LC-MS/MS analysis of 5 and 6 levels in ischemic (A), penumbra (B), and contralateral (C) brain regions of mice 72 hr after pMCAO. Brains were rapidly removed after sacrifice by $CO_2$, sectioned into 2 mm coronal slices, and stained by TTC to visualize the ischemic area. 6 was observed to be formed at higher levels in ischemic tissues, giving way to higher levels of the parent compound, 5, moving outward from the infarct area.

Infarct volume was measured by TTC staining of 2-mm thick coronal brain slices immediately after sacrifice at 72 hr post-pMCAO (4 hr from last dose). Mice treated with 5 were found to have a 37% decrease in infarct volume compared to vehicle (p<0.05, unpaired t-test). Directly after imaging, sections of brain regions were rapidly frozen pertaining to ischemic (no TTC staining), penumbra (mild staining), and contralateral (full staining) areas. Sections were chosen as representative of a full spectrum of ischemic damage after pMCAO. Samples were worked up as with in vitro OGD samples above to assess the levels of 5 and 6 formation. LC-MS/MS analysis of these regions for the levels of 5:6 show decreasing levels of 6 and increasing levels of 5 from the core of the ischemic area (high oxidative stress) outward towards the contralateral area (reduced oxidative stress, FIG. 18). This data indicates that 5 is converted to 6 at higher levels in tissues undergoing oxidative stress, and confirms the observations of higher 6 formation in OGD-treated cells in vitro. This conversion can be used to identify not only NOS inhibitor formation, but tissue-ROS formation and nitrone-NO formation.

Discussion

Design of a ROS-Sensitive NOS Inhibitor

NOS presents a unique target in the treatment of ischemia due to seemingly conflicting results from NOS inhibition or genetic knockouts, which have shown both beneficial and deleterious effects, and may additionally have sex-specific outcomes. Indeed, the precise design criteria for potent and selective NOS inhibitors has seen significant exploration to minimize off-target effects. The co-administration of NOS inhibitors with nitrones for treating neuronal pathology has been previously explored, as well as administration of a nitrone to NOS knockout animals in cardio myocytes, each of which show complimentary beneficial effects.

The active constituent of NXY-059 used in the SAINT-I/SAINT-II clinical trials for acute ischemic stroke may not have been the drug itself, but a decomposition product, N-tert-butylhydroxylamine, formed after the oxidation of the nitrone, and cleavage of the N—C bond. It has been repeatedly shown that the nitrone PBN decomposes to release NO and benzaldehyde under oxidative conditions. This mechanism may account for much of its therapeutic effects. Bi-functional nitrones are being developed to treat ischemic stroke, including a tetramethylpyrazine-functionalized nitrone that was shown to reduce ADP-induced platelet aggregation. However, there has not been an attempt to design nitrones from their decomposition products as pro-drug molecules that are activated under oxidative conditions.

In order to form a putative NOS inhibitor, knowing the oxidative decomposition product would result in formation of a benzaldehyde, the molecule 6 was designed to structurally mimic the NOS inhibitor 1400W. Amidine-containing NOS inhibitors such as 1400W have been shown to be irreversible NOS inhibitors through a heme-oxygenase mechanism that does not cause break-down of the inhibitor. This benzaldehyde would be formed from the nitrone 5. The structure of 5 and its synthesis are such that many derivatives can be rapidly made to separately modulate ROS reactivity and NOS affinity and selectivity. The screening of future derivatives can begin in silico as described herein, by predicting reactivity to biologically relevant ROS, and interaction with NOS isozyme active sites. These approaches have been taken separately for the design of nitrones and NOS inhibitors, and yielded successful results.

ROS Reactivity Calculations

Figure 19:
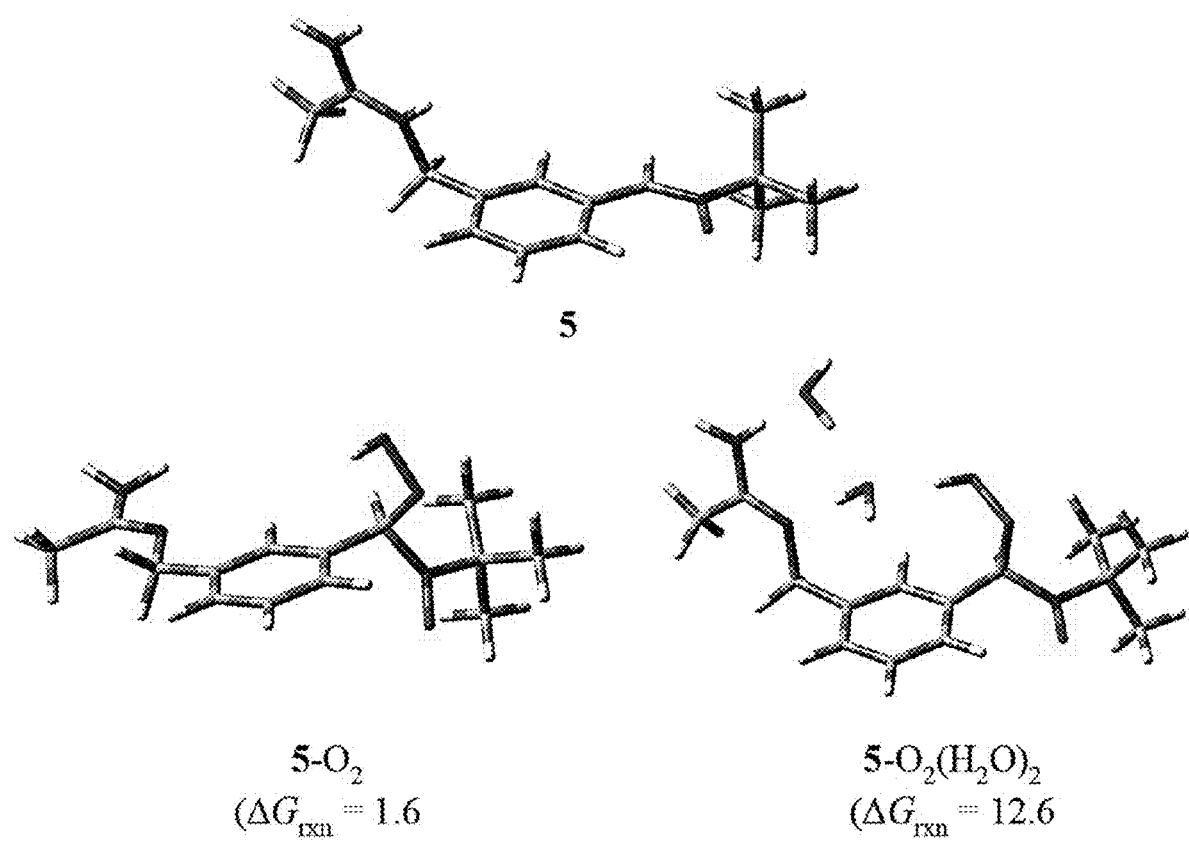
FIG. 19: Optimized structures for 5, $O_2^-$ adducts, and calculated $\Delta G_{rxn}$, formed from $O_2^-$ with and without explicit $H_2O$ molecules at the PCM/B3LYP/6-31+G(d,p)//B3LYP/6-31G(d) level of theory.

Gaussian calculations at the PCM/B3LYP/6-31+G(d,p)//B3LYP/6-31G(d) level of theory of ROS adducts to 5 yielded similar $\Delta G_{rxn}$ to that of PBN except for the anionic species $O_2 \cdot^-$ and $ONOO^-$ that are capable of H-bonding and proton abstraction. It is still unknown if, at neutral pH, $O_2 \cdot^-$ becomes protonated before attack of the nitrone (pKa 4.6), if it reacts with the nitrone and the subsequent peroxyl adduct would become protonated, or if the nitrone itself becomes protonated to form a N-hydroxy imino cation before attack by $O_2 \cdot^-$. It has been shown that intramolecular H-bond donors increase the reactivity of $O_2 \cdot^-$ by disrupting the natural delocalization of its unpaired electron to the non-bonding oxygen, allowing for an increased reactivity towards nitrones. Calculations of the $O_2 \cdot^-$ adduct of 5 with and without explicit $H_2O$ molecules indicate that the peroxyl adduct is basic enough to abstract a proton from the amidine NH in both conditions. In each case, the proximal NH is deprotonated (FIG. 19).

Figure 20:
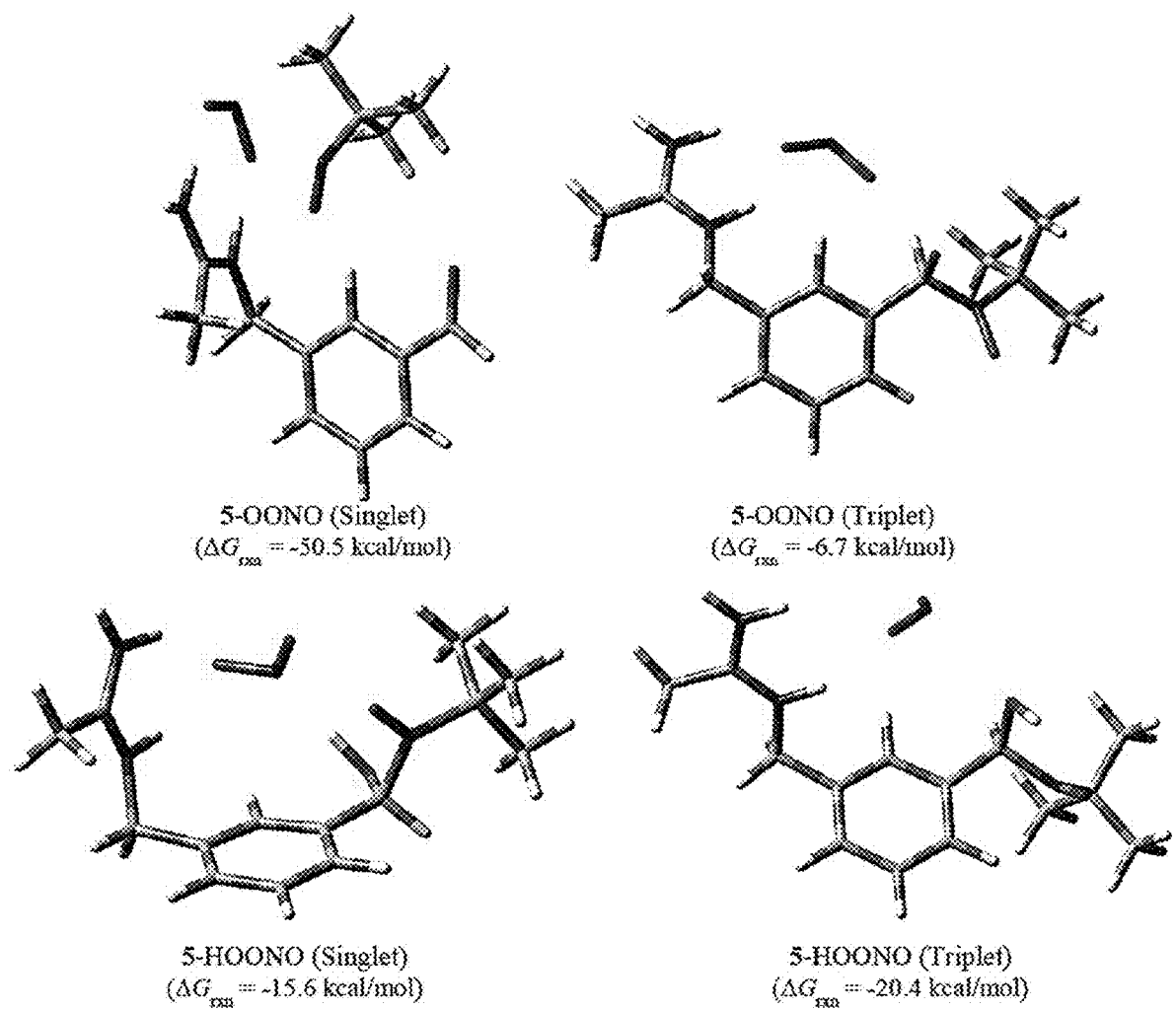
FIG. 20: Optimized structures for 5 $ONOO^-$, ONOOH singlet and triplet adducts, and calculated $\Delta G_{rxn}$ at the PCM/B3LYP/6-31+G(d,p)//B3LYP/6-31G(d) level of theory.

The reaction of 5 with $ONOO^-/ONOOH$ is very interesting, as an EPR spectrum was obtained for $ONOO^-$ with a linear nitrone, and this reaction was shown to completely convert 5 to 6 in situ. Gaussian calculations were performed for both the nucleophilic attack and the radical addition of $ONOO^-/ONOOH$ to PBN and 5. The two mechanisms were found to have similar $\Delta G_{rxn}$ for ONOOH (−15.6 kcal/mol for singlet, and −20.4 kcal/mol for triplet products, respectively) but dramatically different predicted $\Delta G_{rxn}$ for $ONOO^-$ (−50.5 kcal/mol for singlet, and −6.7 kcal/mol for triplet products, respectively) (FIG. 20). In each case, $NO_2$ was predicted to be formed and H-bond with the amidine moiety, which may stabilize a transition state between the reactants and adduct formation. While it is not yet clear if these two mechanisms would ultimately yield different products, the predicted $\Delta G_{rxn}$ matches the observation that a different mechanism predominates in mildly acidic pH, favoring ONOOH formation, than at strongly basic pH. ONOOH is known to exist as a bi-radical trapped in a 'solvent cage' ($\cdot OH - NO_2$), and is significantly less stable than $ONOO^-$. The observation of an EPR spectrum for both 5 and PBN in the presence of $ONOO^-/HCl$ indicates that the mechanism at least in part acts by forming triplet products. However, this EPR spectra was not of an O-centered adduct to the nitrone, which would resemble an $\cdot OH^-$ spectra, but instead a nitroxyl with no H-splitting, which indicates that either the predicted O-centered radical adduct is very short lived and thus not observed, or decomposition of the nitrone occurs before formation of the nitroxyl. This mechanism is physiologically relevant because the uncoupled NOS is a known producer of $ONOO^-$.

Predictive Docking

After in silico calculations showed that 5 would neutralize ROS with $\Delta G_{rxn}$ on par or better than that of PBN, the second part of the proposed mechanism of action, NOS inhibition, was also explored in silico. The NOS inhibitor moiety chosen for 5/6, a methyl amidine, is known to act as a permanent inhibitor of NOS through destruction of the active site heme by a heme-oxygenase mechanism to release carbon monoxide and billiverdin. Interestingly, the enzyme Heme Oxygenase-1 (HO-1), which catalyzes the breakdown of free heme, is beneficial in ischemic stroke, although it is unclear if methyl amidines effect heme-containing proteins beyond that of the NOS family. The predicted ΔG shown in Table 2 indicate that both 5 and 6 are able to coordinate with the active site Glu at energies that are comparable to that of the native ligand L-arginine and potent iNOS inhibitor 1400W. A closer look at the values indicates some differences in the x-ray crystal structures of L-arginine versus 1400W bound proteins: L-arginine ligand ΔG of binding for L-arginine x-ray crystal structures were very near to 1400W ΔG (e.g. −10.32 kcal/mol compared to −10.37 kcal/mol for L-Arginine and 1400W binding to L-arginine eNOS, respectively) while binding to 1400W x-ray crystal structures produced at least a −1.0 kcal/mol difference (e.g. −9.31 kcal/mol compared to −10.34 kcal/mol for L-arginine and 1400W binding to 1400W eNOS, respectively). This is likely due to differences in the active site conformation of the x-ray crystal structures between the two bound ligands. Because the molecules 5 and 6 more closely resemble the structure of 1400W, the ΔG values from the 1400W-bound NOS isozymes are likely to more closely simulate the true interaction.

The 'pro-drug' 5 was shown to bind to each NOS isozyme as well or better than the 'active drug' 6. This is not ideal as it would indicate that the parent molecule could inhibit NOS globally, which is preferably avoided. However, the modeling approach taken here may be used to design derivations of 5 and 6 that would cause decreased favorability of binding for the 'pro-drug' form, which would be lost upon reacting with ROS. Such derivations may, for example, be made to the tert-butyl moiety that may increase bulk and steric hindrance, or increase electrostatic repulsion from the nearby carboxylate of the active site heme.

5 as a Hit Molecule—ROS-Induced Formation of 6

Protein docking of both 5 and 6 to each NOS isoform indicates a similar affinity for the protein active site for both compounds. Ideally, derivative compounds possess reduced affinity of the nitrone prodrug for NOS compared to its decomposition product. After synthesis of 5, EPR spectra were acquired of radical adducts which confirm its antioxidant potential. NO formation from PBN was confirmed to be due to nitrone decomposition in similar systems as well as both in vitro and ex vivo by EPR using 15N—PBN. Furthermore, analysis of these systems by HPLC-PDA and LC-MS/MS strongly indicates the formation of 6 in each of the ROS systems. The development of an MRM method by LC-MS/MS fragmentation of 6 allowed for the sensitive detection of its formation in vitro and in vivo. The decomposition product 6 was detected in vitro by LC-MS/MS in the supernatant and cell lysate of SH-SY5Y cells exposed to OGD. After OGD, levels of 6 were observed to be similar in supernatant fractions (7.88% and 18.6% of 5 AUC for sham and OGD, respectively), but significantly higher in the lysate of OGD-exposed cells (129% vs. 29% of 5 AUC in sham, respectively, p<0.001).

In Vitro Dose-Dependent Neuroprotection of SH-SY5Y Cells by 5

The antioxidant properties of 5 were further confirmed through the neuroprotection afforded to SH-SY5Y cells exposed to OGD. The viability increase was observed to reach a maximum at 1.0 μM of 5 before declining back down to baseline at higher concentrations.

The OGD model of ischemia/reperfusion is known to induce oxidative stress in neuronal cultures through the production of $O_2.^-$, $ONOO^-$, and $.OH$. These ROS were shown above to be trapped in situ by 5, and each were observed to cause decomposition to 6 to some degree. The nitrone 5 was observed to afford dose-dependent neuroprotection to OGD-exposed SH-SY5Y cells in the low micromolar range. The viability increase was observed to reach a maximum at 1.0 µM of 5 before declining back down to baseline at higher concentrations. It should be noted that the highest dose of 5 (100 µM) was not observed to be toxic, but rather non-neuroprotective, as the viability was found to be similar to that of vehicle treated cells. The mechanism of this decline to baseline is uncertain, however it could potentially be due to a large amount of NO release from 5 that could outweigh the benefits of ROS trapping and NOS inhibition. NO is observed to affect different pathways at increasing concentrations, and high levels are cytotoxic.

That 5 was significantly more neuroprotective at 1.0 µM than PBN indicates the amidine substitution of 5 provides some additional beneficial effect, such as through NOS inhibition. In the SIMA9-LPS system, while iNOS is induced, nitrones like PBN are shown to reduce the expression of iNOS under such inflammatory conditions, not affect its activity. Thus, the exact mechanism of reduction in NO by 5, measured as nitrite production, in activated microglia is unclear.

Effect of 5 on Neuroprotective and Anti-Apoptotic Mediators

Western blotting was used to investigate the signaling mechanisms of the neuroprotection afforded by 5 in vitro. The pro-survival pAkt(Ser473) and pERK1/2 (Thr202/Tyr204) were found to be increased in 5-treated SH-SY5Y cells exposed to OGD. Akt is a serine/threonine kinase involved in cell proliferation and apoptosis that becomes phosphorylated at multiple potential phosphorylation sites upon binding PIP3 produced by PI3K. This pathway has been shown to be affected in neurons by both antioxidants and NO-donors in ischemia. PBN was also observed to elicit an increase in Akt phosphorylation, although not significant at the dose selected (1.0 µM), and was unaffected by co-treatment with 1400W. NXY-059 was found to increase pAkt/Akt levels in brains of animals after transient MCAO specific to the infarct and penumbra areas. While this may be due to cell surface interactions, it is more likely to be due to increased reactivity of the nitrone in those areas, leading to ROS neutralization and NO release. This is supported by the data herein which shows greater decomposition of 5 under oxidative conditions in vitro analogous to that of the ROS chemical systems. Utilizing this site-specific property can unlock new avenues of drug targeting in ischemia and various pathologies characterized by oxidative stress.

3-NT and cleaved Caspase-3 were decreased by 1.0 µM 5, which illustrate reductions in $ONOO^-$ production and apoptosis induced by OGD. 3-NT has been shown to be formed from the direct oxidation of protein tyrosines by $ONOO^-$, and was recently shown to be almost completely though uncoupled NOS as opposed to separate mechanisms for $O_2.^-$ and NO production. The formation of 3-NT has been detected in both ischemia/reperfusion and inflammatory pathologies. In each of these evaluations, it was found that NOS was directly involved in 3-NT production, and NOS inhibition was able to decrease its formation. The physiological role for 3-NT formation is not yet fully understood, but it appears to be the main mechanism of $ONOO^-$ mediated damage as it was found that supplementing cells with peptides containing tyrosines susceptible to nitration protects from $ONOO^-$ induced apoptosis. The decrease in 3-NT formation observed here could be due to neutralization of $ONOO^-$ by 5, or to the prevention of its production through inhibiting uncoupled NOS. The mechanism of Caspase-3 cleavage and activation is more clearly elucidated: activation of either the intrinsic or extrinsic cell death pathway causes cleavage of Procaspase-3 to the active 17 kDa and 12 kDa subunits that hydrolyze aspartate-containing peptides. Cytochrome c release from the mitochondria induces the intrinsic cell death pathway via Caspase-9, which then cleaves Caspase-3 to continue the pro-apoptotic signal. NOS has been shown to be involved in Caspase-3 dependent apoptosis in ischemia and its inhibition was found to be beneficial, yet basal NO levels were shown to reduce Caspase-3 cleavage. Since oxidative stress is an inducer of Caspase-3 cleavage via activation of the intrinsic cell death pathway, uncoupled NOS, not functional NOS, is likely the primary inducer of Caspase-3 in these paradigms. Correction of the ROS/NO imbalance by 5 & 6 through antioxidation and uncoupled NOS inhibition after ischemia and reperfusion is believed to underlie the observed increased Akt phosphorylation, and reduced $ONOO^-$ production, 3-NT formation, and Caspase-3 cleavage.

Anti-Inflammatory Properties of Decomposition Product 6

Ischemic stroke causes the progression of microglia, the resident macrophages of the central nervous system, toward a pro-inflammatory phenotype that peaks at 72 hr post-ischemia. This activation causes the production of pro-inflammatory cytokines and free radicals like NO via iNOS, and $O_2.^-$ via NADPH oxidase. These products are toxic to other resident cells, however the increased expression of MnSOD in activated microglia protects themselves from their own ROS generation. LPS stimulates the Toll-Like Receptor 4 (TLR4) receptor on the surface of microglia to provoke an inflammatory response and induce both iNOS and MnSOD expression. In the SIMA9-LPS system, while iNOS is induced, nitrones like PBN (at millimolar levels) are shown to reduce the expression of iNOS under such inflammatory conditions, but not affect its activity. 5 alone did not affect nitrite production, while 6 showed a dose-dependent reduction, which strongly suggests iNOS inhibition. Thus while in silico calculations predict similar iNOS affinity for 5 and 6, only the latter was observed to exhibit inhibition. This shows that 5 needs to be converted by ROS to act as a functional NOS inhibitor. The conversion of 5 to 6 was not measured in this system, yet it was initially thought that some decomposition would occur, and thus cause decreased nitrite formation albeit to a lesser extent than 6 alone. However, due to concomitant upregulation of the far-superior radical scavenger MnSOD, it is likely that insufficient amounts of 5 were reacted to form 6.

Another possible explanation for the lack of nitrite reduction by 5 treatment could be that any conversion of 5 to 6 releases NO which would add to the overall nitrite measured. Thus while iNOS inhibition could have occurred to some extent in 5-treated activated microglia, the NO created from 6 formation could have hidden this result.

6 Forms Preferentially Under Conditions of Oxidative Stress

The formation of 6 from the reaction of 5 with physiologically relevant ROS was confirmed above in situ by HPLC-PDA, LC-MS/MS, and finally by isolation of 6 to allow $^1$H-NMR acquisition. Whether this decomposition occurs in living systems was investigated in OGD-exposed SH-SY5Y cells. The development of an MRM method by LC-MS/MS fragmentation of 6 allowed for the sensitive detection of its formation in vitro. Unfortunately, sufficient quantities of 6 for the generation of a standard curve to allow absolute quantitation were not isolated. Thus the LC-MS/MS AUC for 6 was divided by the intra-run AUC for 5 to give a ratio of 6:5 for each sample. The AUCs of both 5 and 6 were normalized between samples by using 4(1H-Imidazol-1-yl)benzaldehyde (IBA, Sigma) as an internal standard. IBA, bearing a benzaldehyde and an H-bonding imidazole group, was chosen as a standard due to its chemical similarity to 5 and 6 to estimate loss of the latter during sample work-up. The decomposition product 6 was detected in vitro by LC-MS/MS in the supernatant and cell lysate of SH-SY5Y cells exposed to OGD. After OGD, levels of 6 were observed to be comparable in supernatant fractions (18.6% and 7.88% of 5 AUC for OGD and sham, respectively), but significantly higher in the lysate of OGD-exposed cells (129% vs. 29% of 5 AUC in OGD and sham, respectively, $p < 0.001$). This result further confirms that 5 is preferentially converted to 6 in ischemic tissue, very likely due to its reaction with and neutralization of ROS. Coupled with the reduction in nitrite observed in activated microglia by 6, these data clearly illustrate the ROS-dependent activation of the nitrone 5, which then decomposes to release NO and yield the NOS inhibitor 6 preferentially at the site of oxidative stress induced by ischemia (FIG. 1A).

5 has a Dose-Dependent Effect on CBF

The strongest evidence of NOS inhibition by 5 and/or 6 was observed through the measurement of CBF by Laser Doppler Flowmetry over the MCA of treated mice. Intravenous injection of 10 mg/kg 5 to anesthetized mice gave no change in CBF from baseline, yet a lower dose, 1 mg/kg, caused a significant increase in CBF over 20 min. A previous study showed increased MCA CBF in rats with PBN alone, which was lowered to baseline upon co-administration with L-NAME.

The CBF increasing effects of 5 are likely due to a combination of scavenging vasoconstrictive $O_2.^-$, and the releasing of vasodilatory NO, allowing a larger effect than the NO-donor isoamyl nitrate. Acute NOS-inhibitor exposure is observed to cause hypertension and bradycardia at doses as low as 3 mg/kg of L-NAME.

It is unclear if the CBF lowering effects herein are due to excess 5, given its predicted affinity for NOS, or the formation of 6, which was detected in plasma by LC-MS/MS. The in vitro Griess assay of activated microglia indicates that 5 does not have iNOS inhibition properties, and the predicted binding of 5 with eNOS is less than that of iNOS, thus it is unlikely to inhibit vascular eNOS at the administered doses.

Additionally, levels of 6 were higher than expected after only 25 min exposure, which indicates a short half-life of 5. For this reason, a higher loading dose of 5 was chosen for the pMCAO study, followed by a lower dose twice-daily regimen that has found success for experimental nitrones in ischemia.

6 Forms Preferentially in the Penumbra and Ischemic Lesion

The problem with treating ischemia with antioxides and NOS inhibitors is too much focus on a singular mechanism (i.e., anti-oxidation alone), and a lack of ischemia site-specificity. This example overcomes those shortcomings with a ROS-sensitive NOS inhibitor. As described above, 5 is able to neutralize ROS to then decompose to the NOS inhibitor 6 preferentially in ischemic tissue to provide region selectivity and significantly improved neuroprotection and anti-inflammation over conventional nitrones. For these reasons, the effects of 5 and the decomposition product 6 were explored in a mouse model of permanent ischemia.

Figure 15C:
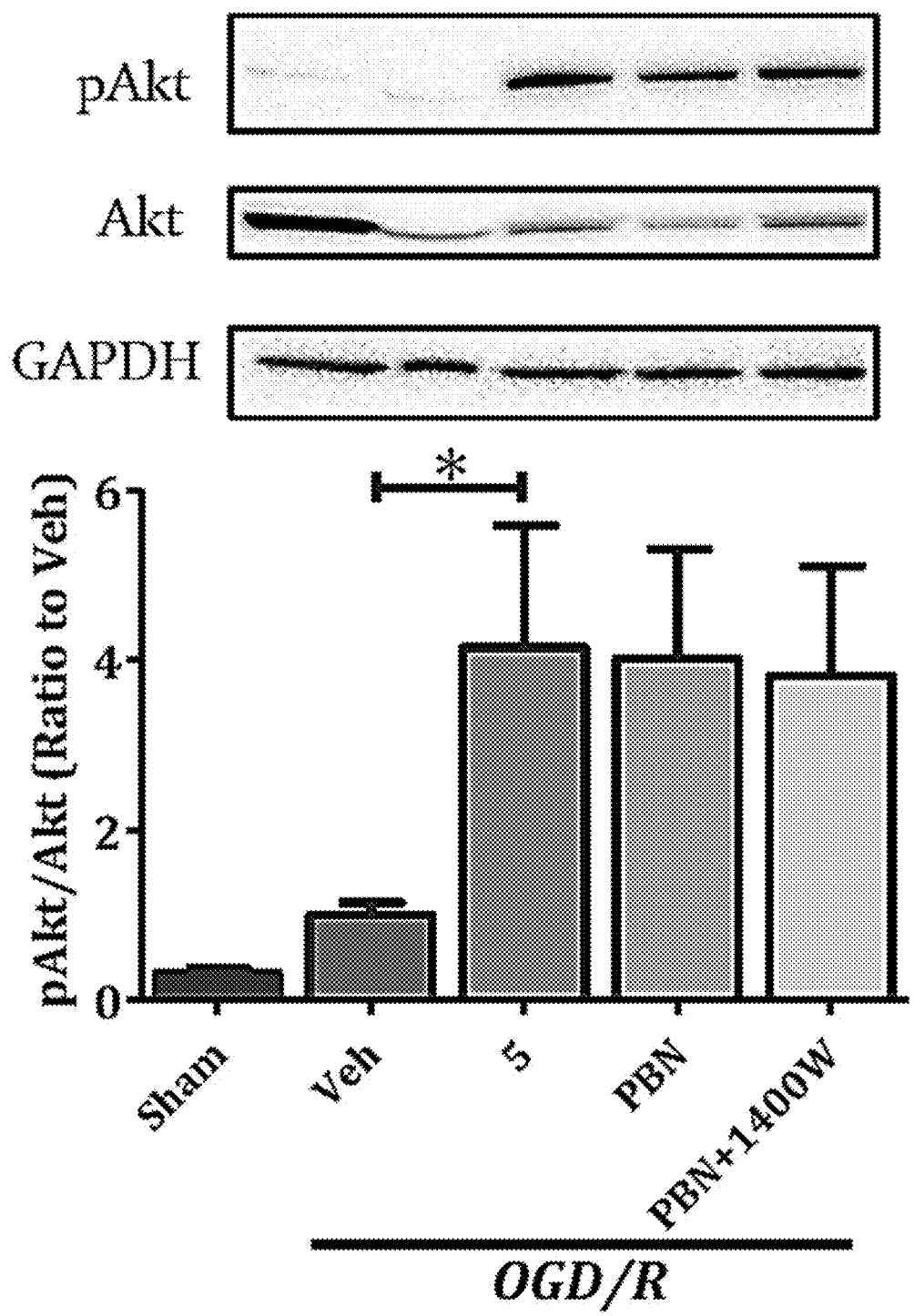
Figure 15D:
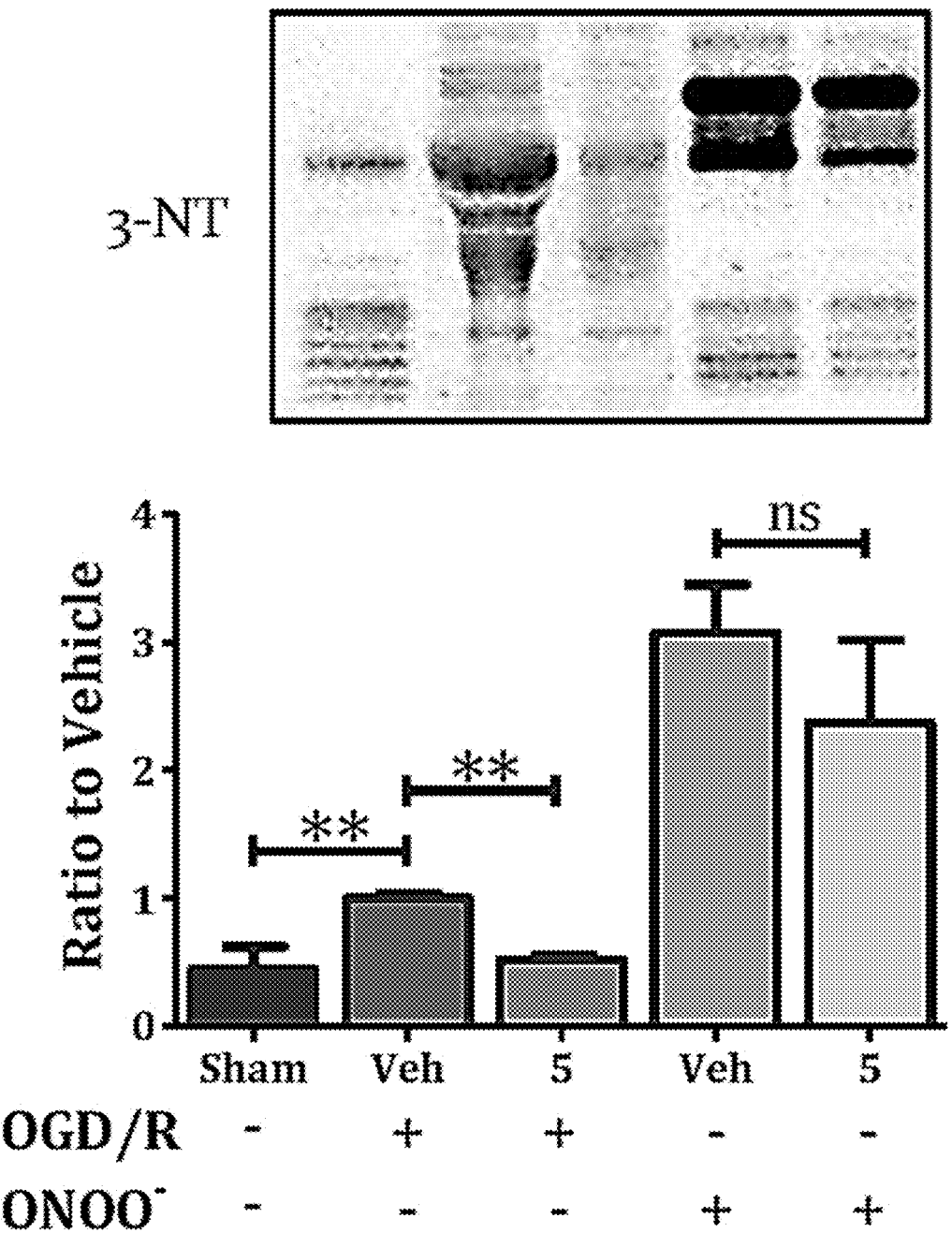
Figure 15E:
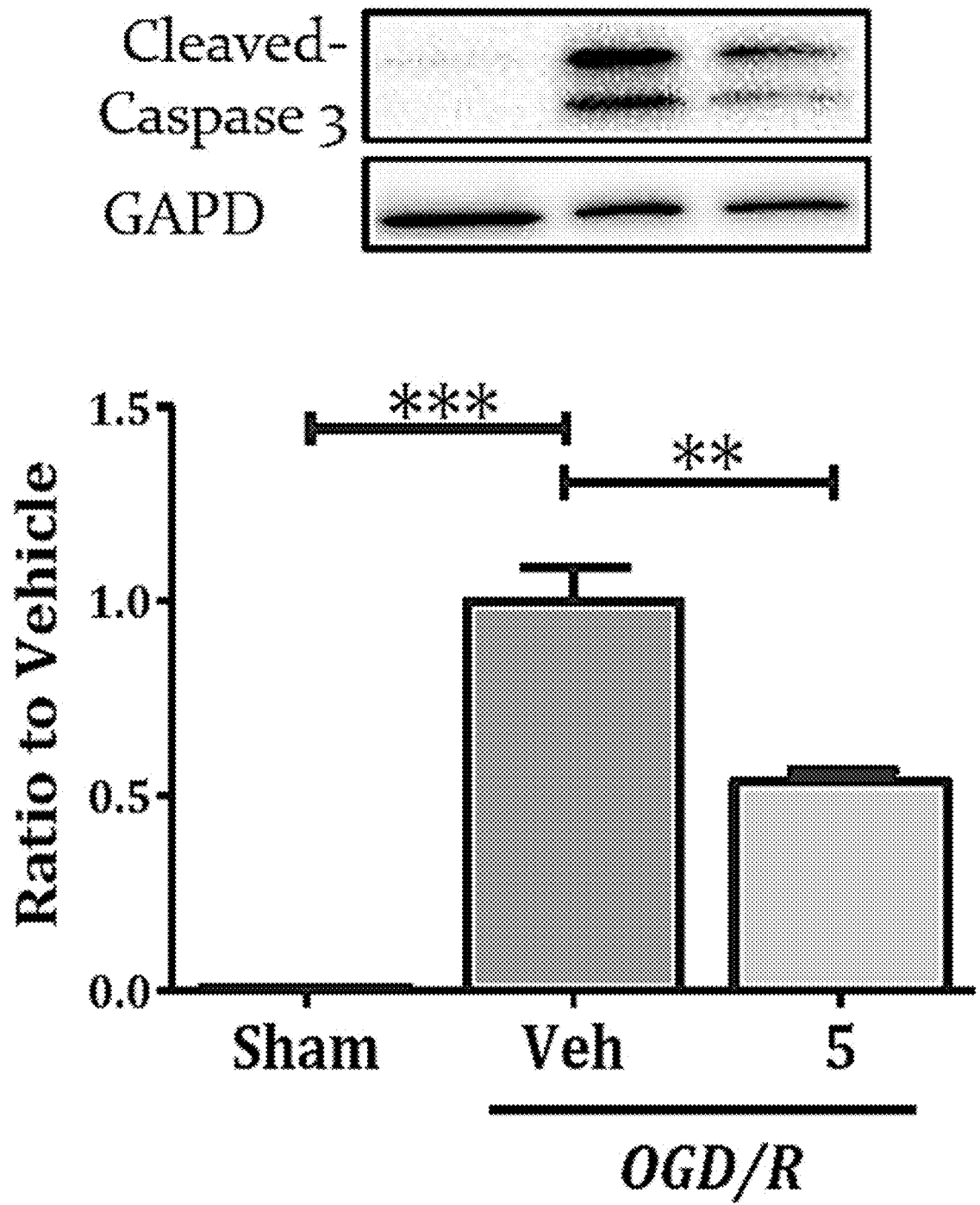
Figure 15F:
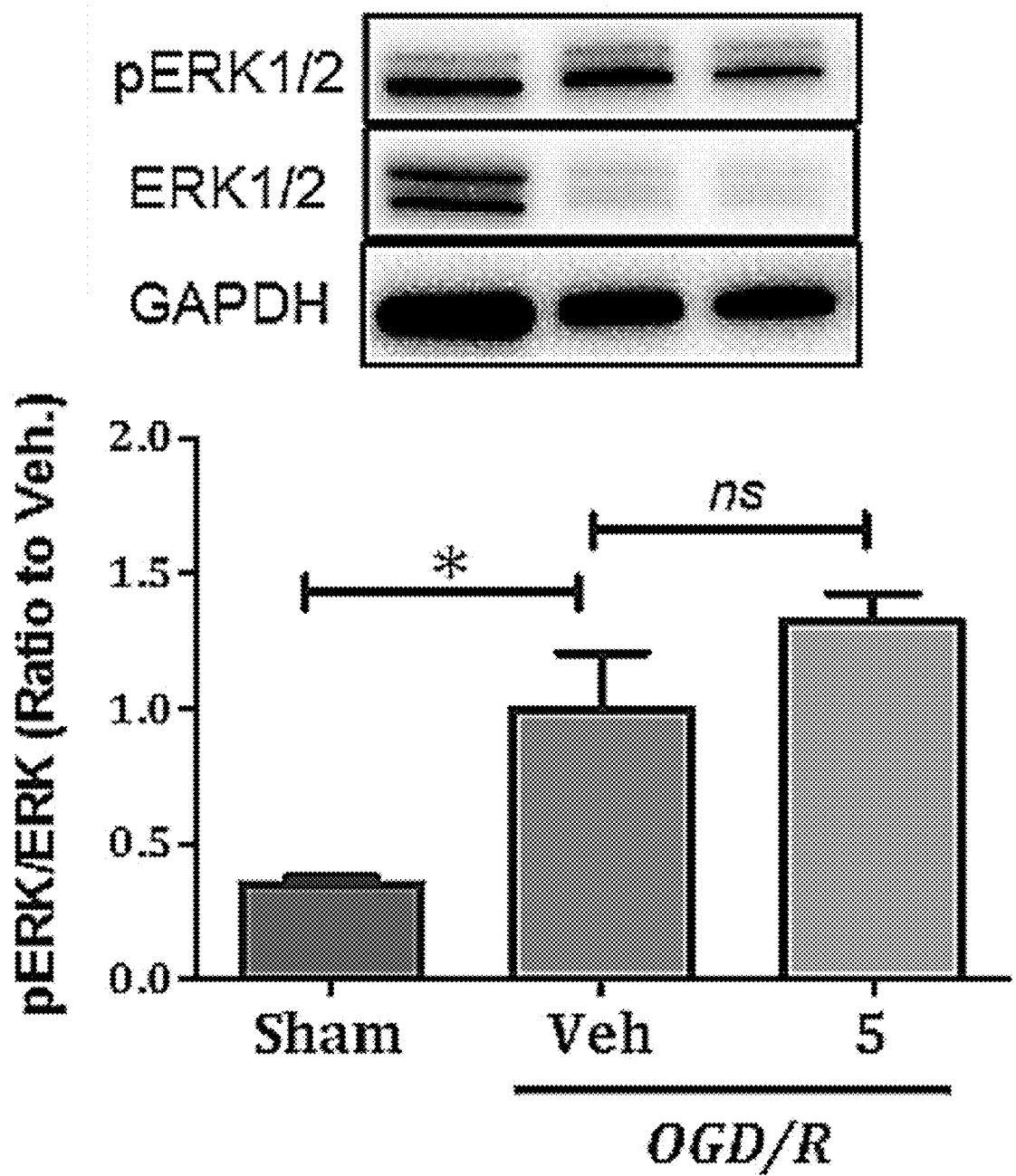

Animals treated with 5 were exhibited a >30% reduction in infarct volume 72 hr after pMCAO as measured by TTC, coupled with significant improvements in neurobehavioral assay performance. The reduction in pMCAO-78 induced infarct volume correlates to the previously described neuroprotection in the in vitro OGD assay. Western blotting was used to investigate the signaling mechanism of the neuroprotection afforded by 5 in vivo and in vitro. (FIGS. 15C-5F.) The pro-survival pAkt(Ser473) was found to be significantly increased in 5-treated SH-SY5Y cells exposed to OGD. This pathway has been shown to be affected in neurons by both antioxidants and NO-donors in ischemia. PBN was also observed to elicit an increase in Akt phosphorylation, although not significant at the dose selected, and was unaffected by co-treatment with 1400W. 3-NT and cleaved caspase-3 were decreased by 1.0 µM 5, which illustrate reductions in $ONOO^-$ production and apoptosis induced by OGD. Correction of the ROS/NO imbalance by 5 & 6 after ischemia and reperfusion is indicated to provide the neuroprotection observed in vitro and in vivo.

The translation of in vitro, OGD-induced formation of 6 to in vivo ischemia, was investigated by LC-MS/MS. Analysis of ischemic, penumbra, and contralateral sections of mouse brains exposed to pMCAO and 5 treatment showed increasing formation of 6 from the contralateral to ischemic areas—in the direction of increasing oxidative stress. Parallel to the in vitro and ROS experiments, the NOS inhibitor 6 is formed in vivo preferentially under conditions of oxidative stress, and here preferentially to the pathologic area. NXY-059 was found to increase pAkt/Akt levels in brains of animals after transient MCAO specific to the infarct and penumbra areas. Without wishing to be bound by theory, it is believed that this is due to increased reactivity of the nitrone in those areas, leading to ROS neutralization and NO release. This is supported by the data herein which shows greater decomposition of 5 under oxidative conditions in vitro and in vivo analogous to that of the ROS chemical systems. Utilizing this site-specific property can unlock new avenues of drug targeting in ischemia and various pathologies characterized by oxidative stress.

The oxidative stress induced during the onset of ischemia is only one phase of neuronal death during stroke, albeit a major one. The secondary injury to neurons occurs upon the activation of microglia which then produce damaging cytokines and excessive NO. Targeting microglial activation after stroke has been investigated and was found to significantly suppress the evolution of ischemic damage at later time points (e.g. 24 to 48 hr) Similarly, astrocytes are activated after ischemia/reperfusion, and also increase iNOS expression in the days following ischemia. The iNOS inhibitor 1400W was found to be neuroprotective in an animal model of transient ischemia, and co-treatment with an NO-donor increased functional recovery of perfused skeletal muscle. In addition to targeting the uncoupled NOS induced by ischemia, 5 treatment, through 6 formation, is likely able to reduce iNOS activity through its inhibition as observed in the Griess assay of activated microglia. Thus, the initial bolus 5 would provide neuroprotection from oxidative stress, as is typical of classical antioxidants, and the formation of 6 prevents secondary inflammatory injury caused by iNOS expressed by activated microglia and astrocytes after ischemia.

Nitrones as CNS-Permeable, ROS-Sensitive Prodrugs

Despite being charged at physiological pH, 5 and 6 were both detected in the CNS by LC-MS/MS of brain tissue. It may be beneficial to increase permeability while fighting the prototypical hydrophilicity of NOS-inhibitors and increasing isoform specificity. The advantages of the methods employed in this example include ease of synthesis to allow derivatization, and allowing for aldehyde NOS inhibitors to be characterized and screened prior to formation of their corresponding nitrone. However, 5 demonstrates the ability of nitrones to act as more than antioxidants, rather as carrier molecules that are able to provide an additional, site-specific action. NOS was explored as one such target due to its unique dual-roles under oxidative pathology, however other molecular pathways can be targeted using the above methodologies.

Experimental

Computational Methods

Ab initio structures of nitrones, radicals, and radical adducts were generated using Avogadro at the MMFF94 level. Optimized geometries were then determined by density functional theory (DFT) at the B3LyP/6-31G* level of theory as previously described yielding no imaginary vibrational frequency. All calculations were performed using Gaussian 0944 at the Ohio Supercomputer Center and visualized by GaussView 5.0 software. B3LYP/6-31G* geometries were corrected using a scaling factor of 0.980645 for the zero-point vibrational energy (ZPE). Solvation effects on the gas-phase calculations were determined using the PCM, and spin and charge densities were assigned using natural population analysis (NPA) at the PCM/B3LYP/6-31+G** level of theory. All doublet and triplet calculated minima yielded negligible spin contamination (0.75<(S2) <0.76). $\Delta_{rxn,298K}$ (kcal/mol) of adduct formation was determined by $\Delta G_{Adduct} - \Delta G_{Reactants}$.

Protein docking studies were carried out using Swissdock.ch and visualized by UCSF Chimera soft-ware. X-ray crystallographic structures of each NOS isoform with L-arginine or 1400W bound were used to determine the free energy of interaction with the enzyme active site. Docking was limited to ±10.0 Å of the native bound ligand (L-arginine or 1400W) in the X, Y, and Z directions.

Synthesis

The four-step synthesis of 5 (FIG. 2) was carried out with a favorable overall yield of 52.5%. The intermediates allow for multiple points of derivatization for the quick synthesis of a focused library. The boc-protected benzyl alcohol 1 was purchased for the synthesis in this example, however the precursor 3-(aminomethyl)-benzenemethanol can be purchased at low cost for large-scale synthesis. Activation of the boc-protected benzyl alcohol 1 by Appel bromination allows for substitution with tert-butyl amine (3), then further deprotection permits substitution with an amidine (4). These two steps can be used for future derivatization to modulate activity of the nitrone and NOS-inhibitor aspects of the molecule, respectively. The final step is oxidation of the secondary amine to the nitrone 5 by $NaWO_4$—$H_2O_2$. While no oxidation of the amidine was observed, other intermediates may be sensitive to this oxidation step. Analysis by $^1H$ and $^{13}C$ NMR, HRMS, and HPLC-PDA showed the successful synthesis of 5 at >95% purity. The intermediate 4 was found to have very weak absorbance, even at its $\lambda_{max}$ of 260 nm, but following oxidation to the nitrone 5, the $\lambda_{max}$ shifted to 289 nm and gave strong absorbance character. The formation of the nitrone results π-electron conjugation from the benzene ring to continue through the nitronyl N—O bond which greatly affects its absorbance spectra. This observation correlates with the breaking of this conjugation and subsequent decrease in absorbance and $\lambda_{max}$ upon reaction of 5 with free radicals.

Materials were purchased from commercial suppliers (Sigma or Fisher), and used as received. Each synthetic reaction was carried out under an Argon atmosphere, and products were stored at –20° C. after purification. Reactions were monitored by TLC (LuxPlate silica gel 60 F254 plates), and revealed by UV (254 nm), iodine, or ninhydrin stains. Flash column chromatography was performed using a Teledyne Combiflash Rf with RediSepRf Gold columns Purity analysis by HPLC was performed using a Shimadzu Prominence HPLC (LCD-20AD) with temperature controlled autosampler (SIL-20AC), and PDA (SPD-M20A) detector. HPLC conditions: Phenomenex Kinetix® core column (2.6 μm, C18, 100 Å, 100×4.6 mm), mobile phase A=25 mM ammonium formate in water (0.1% for-mic acid [FA]), mobile phase B=ACN (0.1% FA), 1.0 mL/min, 5% B to 95% B over 5 min followed by 95% B for 2 min then 5% B for 5 min re-equilibration (total run time=12 min). $^1H$ and $^{13}C$ NMR were taken using a Bruker Avance 600 MHz spectrometer (cryoprobe), and HRMS was acquired using a Waters Synapt high definition mass spectrometer (HDMS) equipped with a nano-ESI source positive mode.

tert-butyl (3-(bromomethyl)benzyl)carbamate (2)

tert-butyl (3-(hydroxymethyl)benzyl)carbamate (1, AstaTech, 500 mg, 1.0 eq) was dissolved in 8.8 mL anhydrous $CH_2Cl_2$ at 0° C. with stirring. $CB_{r4}$ (838 mg, 1.2 eq) was added spatula-wise over 5 min, followed by $PPh_3$ (663 mg, 1.2 eq) spatula-wise over 10 min. Reaction was left to warm to rt and allowed to stir for 30 hr. $CH_2Cl_2$ (50 mL) was added, washed with brine (3×20 mL), evaporated, and purified by column chromatography (hexanes:EtOAc). 2 was afforded as a clear solid (577 mg, 91.2%), NMR ($CDCl_3$, 400 MHz): δ7.35-7.24 (4H, m), δ 4.88 (1H, br), δ 4.51 (2H, d, J=3.92 Hz), δ 4.34 (2H, d, J=3.60 Hz), δ 1.49 (9H, s).

tert-butyl (3-((tert-butylamino)methyl)benzyl)carbamate (3)

To a stirring solution of tert-butylamine (237 mg, 1.8 eq) and $K_2CO_3$ (234 mg, 1.3 eq) was added 2 (542 mg, 1.0 eq) in 3.6 mL anhydrous DMF by syringe at rt. The reaction was allowed to stir for 3 hr, then diluted with 15 mL $dH_2O$, and extracted with ether (3×30 mL). The organic layer was washed with brine (3×20 mL), dried with $Na_2SO_4$, filtered, and evaporated. Separation by column chromatography (hexane:EtOAc) yielded 3 as a white solid (509 mg, 96.4%), NMR ($CDCl_3$, 400 MHz): δ7.31-7.25 (3H, m), δ 7.18-7.17 (1H, m), δ 4.85 (1H, br), δ 4.32 (2H, d, J=3.68 Hz), δ 3.73 (2H, s), δ 1.49 (9H, s), δ 1.20 (9H, s).

N-(3-((tert-butylamino)methyl)benzyl)acetimidamide (4)

3 (390 mg, 1.0 eq) was dissolved in 44 mL $CH_2Cl_2$ with stirring at 0° C. Trifluoroacetic acid (10.2 mL, 100 eq) was rapidly added by syringe, and allowed to stir for 2 hr on ice. The solvent was evaporated to give a brown oil which was re-suspended in 1.5 mL 1:1 $dH_2O$/EtOH, and 2 N NaOH was added until pH>12. The mixture was extracted with $CH_2Cl_2$ (2×15 mL), dried with $Na_2SO_4$, filtered, and evaporated in a round-bottom flask. The residue was dissolved in 5 mL anhydrous EtOH, ethyl acetimidate (165 mg, 1.0 eq) in 2 mL EtOH was added dropwise and let stir at rt for 12 hr. The reaction was evaporated, re-suspended in 15 mL $dH_2O$, and then the aqueous layer was washed with ether (3×15 mL)

and EtOAc (2×15 mL). Lyophilization of the aqueous layer gave 4 as a white, hygroscopic solid (295 mg, 94.7%), $^1$H NMR (CD3OD, 400 MHz): δ 7.52 (2H, s), δ 7.47-7.46 (2H, m), δ 7.39-7.37 (1H, m), δ 4.53 (2H, s), δ 3.98 (2H, s), δ 2.32 (3H, s), δ 1.38 (9H, s).

N-tert-butyl-α-(3-[ethanimidamidomethyl]phenyl) nitrone (5)

4 (174 mg, 1.0 eq) was dissolved in 2 mL MeOH, and added to a round-bottom flask containing $Na_2WO_4(H_2O)_2$ (10 mg, 0.05 eq) at 0° C. with stirring. Ice-cold 30% $H_2O_2$ (263 μL, 4.0 eq) was added dropwise over 5 min. The reaction was left to warm to rt and allowed to stir vigorously for 12 hr. 20 mL $CH_2Cl_2$ was added, the organic layer was separated, and the aqueous layer was extracted with $CH_2Cl_2$ (2×20 mL). Purification of the organic layer by column chromatography ($CH_2Cl_2$:MeOH) afforded 5 as a brown oil (122 mg, 66.2%), $^1$HNMR (DMSO-d6, 400 MHz): δ 9.89 (1H, br), δ 9.29 (1H, br), δ 8.84 (1H, br), δ 8.60 (1H, s), δ 8.12 (1H, d, J=5.24 Hz), δ 7.89 (1H, s), δ 7.47-7.39 (2H, m), δ 4.49 (2H, s), δ 2.22 (3H, s), δ 1.52 (9H, s); 13C NMR (DMSO-d6, 100 MHz): 164.75, 135.65, 132.39, 129.43, 128.99, 128.91, 128.75, 127.54, 71.05, 45.69, 28.32, 19.22; HPLC purity (254 nm): 95.8%; HRMS (M+H) m/z 248.1759, calcd for $C_{14}H_{21}N_3O$ 248.1757.

N-[(3-formylphenyl)methyl]ethanimidamide (6)

To a stirring solution of 5 (5.0 mg, 1.0 eq) in 785 μL PBS was added 20 μL 6 N HCl at 37° C. Peroxynitrite (200 μL of a 50 mM solution in 0.3 M NaOH, 0.5 eq) was added in 50 μL aliquots over 5 min. The reaction was allowed to stir for 1 hr and monitored by HPLC-PDA. The solution was extracted with $CH_2Cl_2$ (2×0.5 mL) and the aqueous fractions were pooled then lyophilized. Addition of ACN (1.0 mL) to the white solid followed by filtration allowed separation from the insoluble salts. Lyophilization afforded 6 as a white solid (1.2 mg, 33.7%), NMR (CD$_3$OD, 400 MHz): δ 10.04 (1H, s), δ 7.93-7.95 (2H, m), δ 7.71-7.65 (2H, m), 4.58 (2H, s), δ 2.30 (3H, s).

EPR Spectroscopy

EPR spectra were collected at ambient temperature with microwave power 12.6 mW, frequency 9.86 GHz, receiver gain $1.0×10^5$ or $1.0×10^4$, modulation amplitude 1 G, scan time 20.48 sec, time constant 40.96 msec, and sweep width 120 G. Phosphate buffered saline (PBS) used for EPR was supplemented with diethylenetriaminepent-acetic acid (DTPA, 100 μM). ROS-generating solutions were rapidly added to solutions of indicated spin trap and taken up in 50 μL glass capillary tubes for EPR spectral acquisition. For HPLC-PDA analysis, solutions were allowed to incubate for 24 hr at 37° C., then diluted 1:1000 in 95:5 mobile phase A:B, and analyzed as above. Benzaldehyde (Sigma) was run separately as a control to compare to PBN-ROS systems and confirm PBN decomposition.

$O_2.^-/HO_2.^-$-Generating System

A 50 μL final 20% PBS/DMSO solution of 35 mM 5 or PBN contained 10 μL saturated $KO_2$ DMSO.

.OH/.$CH_3$-Generating System

A 50 μL final 30% PBS/DMSO solution of 35 mM 5 or PBN contained 90 mM $FeSO_4$ and 1% $H_2O_2$.

ONOO$^-$/HCl System

A solution of ONOO$^-$ in 0.3 M NaOH (Cayman Chemical) was determined to be 50 mM by absorbance at 302 nm using the literature extinction coefficient (1670 $M^{-1}cm^{-1}$). A 50 μL final 30% PBS/DMSO solution of 5 or PBN contained 10 mM ONOO$^-$ at pH~6 (HCl).

Cell Culture

Human neuroblastoma SH-SY5Y cells and SIM-A9 mouse microglia (ATCC) were separately cultured on poly-D-lysine coated plates in 1:1 Dulbecco's Modified Eagle Medium/Ham's F12 (DMEM/F12) medium containing 5% fetal bovine serum, 5% horse serum, and penicillin-streptomycin. Cultures were stored in a 37° C. incubator with a 5% $CO_2$ atmosphere. Cells were allowed to adhere overnight prior to subjection to experimental systems. $1×10^6$ cells SH-SY5Y cells on 96-well plates were used for OGD experiments, and SIM-A9 cells were plated at a density of $1×10^6$ on 24-well plates for Griess experiments.

Oxygen-Glucose Deprivation (OGD)

Growth medium was removed from SH-SY5Y cells and replaced with sterile HBSS (140 mM NaCl, 3.5 mM KCl, 0.4 mM $KH_2PO_4$, 5 mM $NaHCO_3$, 1.3 mM $CaCl_2$, 1.2 mM $MgSO_4$, 20 mM HEPES, pH 7.4, bubbled with 95%/5% $N_2/CO_2$), and placed in an air-tight container subsequently purged three times with 95%/5% $N_2/CO_2$. The container was then placed in a 37° C. incubator for 1.5 hr. After OGD, the cells were returned to a normoxic environment, and medium was replaced with growth medium and vehicle or treatment for 24 hr to simulate reperfusion. Sham cells were left in growth medium under a normoxic environment. Viability was measured by adding 10% Presto-Blue® Cell Viability Reagent (Thermo Fisher) for 30 min, and reading fluorescence at 560 nm/590 nm excitation/emission. Viability is reported as a ratio to vehicle-treated control, and readings result from separate OGD experiments (e.g. n=6 was from 6 different OGD assays). The experimental furoxan IS-1-41 was used as a positive control for OGD viability due to its reproducible protection in this paradigm.

Western Blotting

SH-SY5Y cells exposed to 1.5 hr OGD followed by 24 hr vehicle or treatment were harvested and lysed by RIPA buffer (150 mM NaCl, 1% NP-40, 0.5% Na Deoxycholate, 0.1% SDS, 50 mM Tris, 5 mM EDTA, 1 mM EGTA, 0.2 mM phenylmethylsufonyl fluoride, 0.5 mM DTT, 1 mM sodium othovanadate, 50 mM NaF, 10 mM sodium pyrophosphate, protease inhibitor cocktail [Thermo Fisher]). Equivalent amounts of protein as determined by Bradford assay were loaded onto 4-20% tris-glycine gels and separated by electrophoresis. Proteins were transferred to a PVDF membrane, blocked with 5% BSA-TBST, and probed with primary antibodies in blocking buffer (anti-phospho-Akt(Ser473) 1:2000; anti-Akt 1:1000; anti-Nitrotyrosine 1:1000; anti-cleaved caspase-3(Asp175) 1:1000, Cell Signaling; anti-GAPDH 1:2000, Thermo Fisher) followed by secondary antibody (HRP goat anti-rabbit IgG 1:10,000, Jackson) in 5% milk-TBST. Images were acquired using a BioRad ChemiDoc™ XRS+, and densitometry was analyzed using ImageJ software (NIH) normalized to GAPDH loading control.

Griess Assay

SIM-A9 cells were treated with 100 ng/mL lipopolysaccharide (LPS, Sigma) along with vehicle or drug treatment for 24 hr. Conditioned medium was then diluted 1:1 with griess reagent (0.4% naphthylethylenediamine dihydrochloride, and 4% sulphanilamide in 10% phosphoric acid), and analyzed by colorimetry at 540 nm after 5 mM incubation. Nitrite levels were reported as a ratio to LPS-treated, vehicle control.

Animals

All animal protocols were approved by the University of Toledo Health Science Campus Institutional Animal Care and Utilization Committee, and NIH guidelines were followed. Male C57BL/6 mice, 6-8 weeks old at 23-25 g (Charles River) were housed with a 12 hr light/dark cycle at 22±1° C.

Permanent Middle Cerebral Artery Occlusion (pMCAO)

The distal part of the MCA was permanently occluded as previously optimized. Briefly, mice were anesthetized with 1% isoflurane, the site was aseptically cleaned, and a small 1.0 cm incision was made between the left eye and ear. The temporal muscle was moved aside to view the MCA under the temporal bone, and a 2 mm hole was drilled with a dental drill directly over the distal MCA. The artery was directly occluded with a bipolar coagulator, and the incision was sutured. The animals' body temperature was maintained at 37.0±5° C. throughout the procedure and after surgery until recovery. Animals were intravenously injected by lateral tail vein with 100 μL normal saline or 10 mg/kg 5 in vehicle at 3 and 6 hr after pMCAO. Either vehicle or 1 mg/kg 5 were then dosed twice daily thereafter, spaced 8 hr apart, until sacrifice by $CO_2$ inhalation at 72 hr post-pMCAO.

Laser Doppler Cerebral Blood Flow (CBF)

Animals were anesthetized and the incision was performed as above to expose the temporal bone, through which the MCA was visible. The end of a fiber optic cable fitted to a MoorVMS-LDF Laser Doppler Monitor (Moor Instruments) was positioned in place over the MCA. The baseline CBF as flux was monitored for 5 min prior to intravenous injection by lateral tail vein of normal saline vehicle, isoamyl nitrate (20 mg/kg), or 5. Measurements were taken every 5 minutes in triplicate for each animal, and reported as ratio to baseline. Animals were sacrificed at 25 min by $CO_2$ inhalation, blood was collected into $K_2EDTA$ coated tubes (BD Microtainer®), and brains were rapidly dissected out and frozen on dry ice for LC-MS/MS analysis.

Neurobehavioral Assays

Mice were trained on neurobehavioral paradigms for 3 days prior to pMCAO, and baseline readings were recorded 24 hr prior to surgery. For rota rod analysis, mice were placed on a moving rod (Columbus Instruments) programmed to rotate at 1 rpm and accelerate by 1 rpm every 10 sec until the animal falls from the rod. The latency to fall was recorded manually and reported as ratio to base-line. Grip strength analysis was performed using a grip strength meter (Columbus Instruments) fitted with a pull bar assembly. Forelimbs of mice were placed on the bar and peak force until release when pulled by the tail was displayed on the digital display and manually noted. Neurological deficit scoring (NDS) was conducted 72 hr after pMCAO prior to sacrifice, and evaluated on an optimized 28-point score pattern. The total score was determined by the sum of the seven criteria graded from 0 to 4, with higher scores indicating more severe deficits.

Infarct Volume

Brains of animals sacrificed by $CO_2$ inhalation 72 hr after pMCAO were rapidly dissected out, sliced into five 2 mm-thick coronal sections, and incubated in warm 1% triphenyltetrazolium chloride (TTC, Sigma) in normal saline. Infarct volumes were estimated by measuring rostral and caudal sides of each section in conjunction with the thickness, and expressed as a percentage of the volume of the contralateral hemisphere. After imaging, portions of the ischemic lesion, penumbra, and contralateral tissue were quickly frozen on dry ice for LC-MS/MS analysis.

LC-MS/MS

Synthesized 5, and purchased 4(1H-Imidazol-1-yl)benzaldehyde (IBA, Sigma) were used to determine LC-MS/MS fragmentation. A solution of 5+$ONOO^-$/HCl from EPR studies was used for 6 fragmentation. MRM analysis of IBA (m/z 173.10→91.10, 104.10, 117.05; RT: 4.13 min), 5 (m/z 248.20→148.00, 134.15, 190.05; RT: 4.81 min), and 6 (m/z 177.00→119.10, 90.95, 65.15; RT: 3.87 min) were determined. A standard curve for 5 was generated using pure samples applied to blank matrix (0.01 μM, 0.1 μM, 0.5 μM, 1.0 μM, and 5.0 μM; R2=0.99) using the above HPLC solvents and LC curve at 0.4 mL/min.

In vitro supernatant samples were spiked with internal standard (200 μL 500 nM IBA in 2% FA) and used as collected, while cells were detached by trypsin, centrifuged (14 k rpm, 5 min, 4° C.) to isolate the pellet, then lysed by sonication (Sonic Dismembrator 500, Fisher) in 1 mL cold PBS+internal standard. Blood samples (100 μL) were spiked with internal standard, and centrifuged to collect the supernatant. Brain samples were weighed, homogenized by a Bullet Blender Storm (Next Advance Inc.) in 500 μL cold PBS+internal standard for 1 min at 4° C., then centrifuged to collect the supernatant. All samples were then worked up by solid phase extraction (Evolute Ex-press ABN cartridge, 30 mg/1 mL, Biotage) using a Vac-master manifold (Biotage). Columns were washed with $dH_2O$ (1 mL), and analytes were eluted with MeOH (1 mL) and evaporated to dryness by high flow air purge. Samples were reconstituted in 200 μL 95:5 mobile phase A:B and analyzed by LC-MS/MS (2.0 μL injection volume). All samples were run in duplicate, and AUC for 5 and 6 were normalized to the intra-run IBA AUC to account for loss during workup. 5 concentrations were determined using std. curve, while 6 was expressed as a percentage of 5 AUC.

Certain embodiments of the compounds, compositions, and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A compound comprising Formula I:

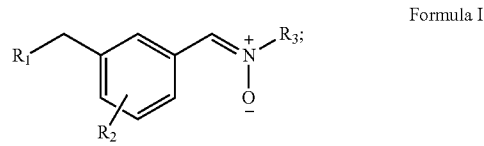

Formula I and salts, stereoisomers, racemates, solvates, hydrates, and polymorphs thereof, wherein:

$R_1$ is substituted or unsubstituted amino, amidinyl, guanidinyl, protonated amidinyl, protonated guanidinyl, protonated amidinyl sulfide, aminoguanidinyl, thiophenyl, ethyl amidinyl, methyl amidinium sulfide, or pyridinyl, wherein $R_1$ may form a ring with $R_2$;

$R_2$ is H or a bridging group that forms the ring with $R_1$;
$R_3$ is a stable radical that permits NO to be given off as a radical when the compound interacts with reactive oxygen species.

2. The compound of claim 1, wherein $R_3$ is substituted or unsubstituted alkyl, aryl, heteroaryl, aryloxy, alkoxy, or heterobicyclyl.

3. The compound of claim 2, wherein $R_3$ is substituted with one or more hydroxyl, methyl, isobutyl, carboxylate, or combinations thereof.

4. The compound of claim 1, wherein $R_3$ is tert-butyl, 2,6-di-tert-butylphenolyl, 3,5-di-hydroxybenzoate, 1,3-di-tert-butyl-4,5-dimethyl-imidazolyl, or 1-hydroxy-2,3,6-trimethylbenzo-2-methyloxanyl.

5. A compound comprising Formula I:

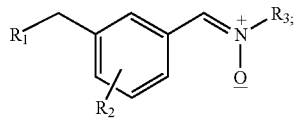

Formula I and salts, stereoisomers, racemates, solvates, hydrates, and polymorphs thereof,
wherein $R_1$ comprises amidinium, nitroguanidinium, thiopheneamidinium, methyl amidinium sulfide, 2-amino-4-methylpyridinyl, aminopyridine, amidinyl, thiophenylamidinyl, or amino; wherein $R_1$ may form a ring with $R_2$;
$R_2$ is H or a bridging group that forms the ring with $R_1$;
$R_3$ is a stable radical that permits NO to be given off as a radical when the compound interacts with reactive oxygen species.

6. The compound of claim 1, wherein the ring is a pyrazole ring, an imidazole ring, a pyrrole ring, a pyrrolidine ring, a pyrimidine ring, a pyridine ring, or a piperidine ring.

7. The compound of claim 1, wherein the compound comprises Formula II:

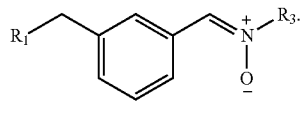

Formula II

8. The compound of claim 1, wherein the compound comprises Formula III:

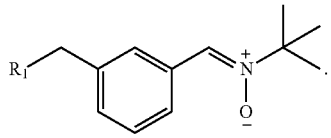

Formula III

9. The compound of claim 1, wherein:
$R_3$ is H; and
$R_1$ and $R_2$ form a pyrazole ring.

10. The compound of claim 5, wherein $R_1$ comprises aminopyridine.

11. The compound of claim 5, wherein $R_1$ comprises 2-amino-4-methylpyridine.

12. The compound of claim 5, wherein:
$R_1$ is 2-amino-4-methylpyridine; and
$R_2$ is H.

13. The compound of claim 5, wherein $R_1$ comprises amidinyl.

14. The compound of claim 5, wherein $R_1$ comprises thiophenylamidinyl.

15. The compound of claim 1, wherein the bridging group comprises an amino group.

16. The compound of claim 1, wherein the compound comprises compound 5:

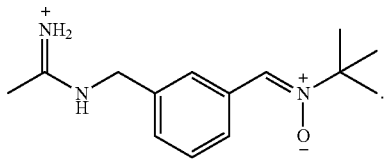

(5)

17. The compound of claim 1, wherein the compound comprises one of compounds 7-35:

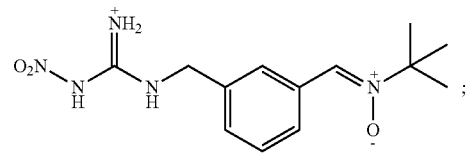

(7)

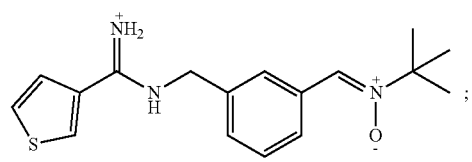

(8)

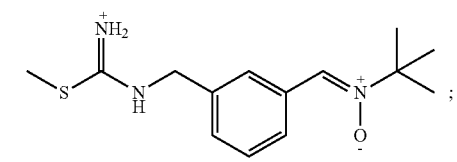

(9)

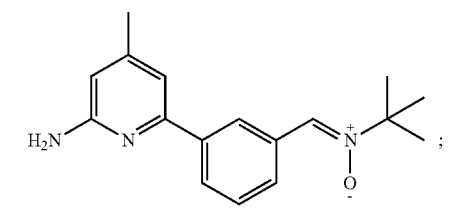

(10)

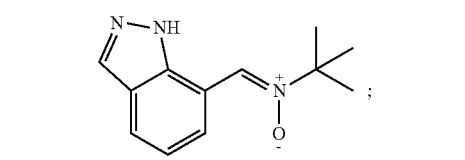

(11)

-continued
(12)
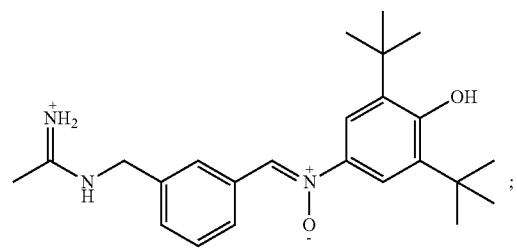
(13)
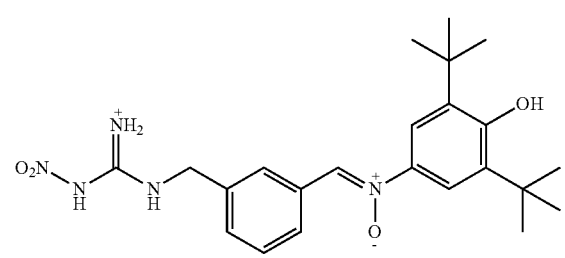
(14)
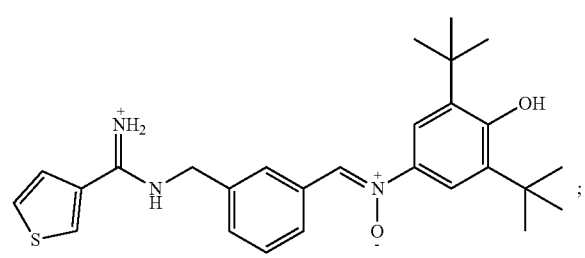
(15)
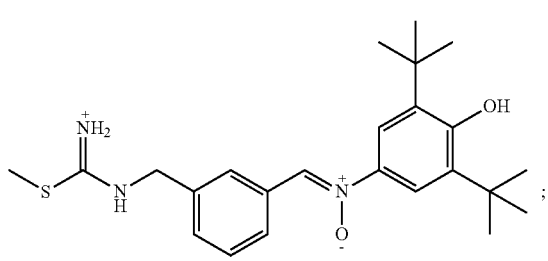
(16)
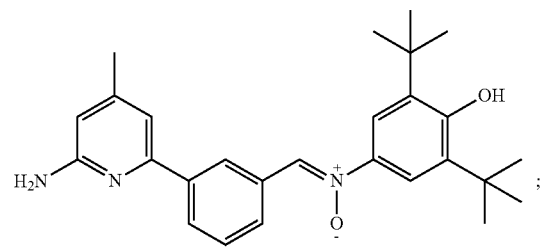
(17)
-continued
(18)
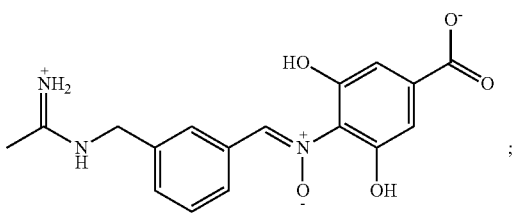
(19)
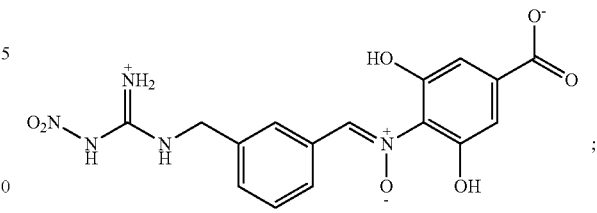
(20)
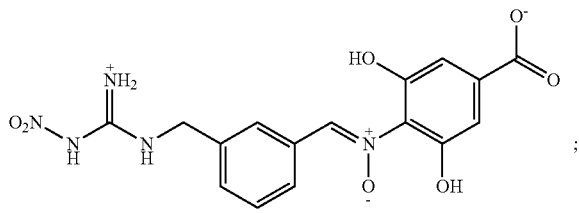
(21)
(22)
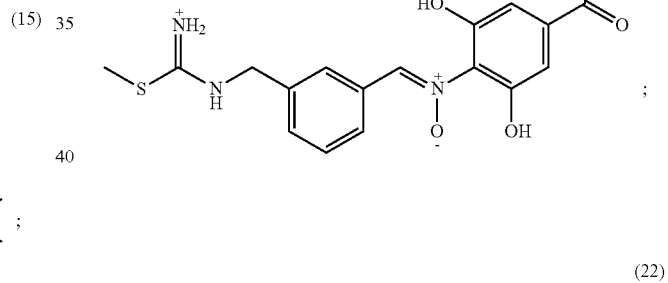
(23)
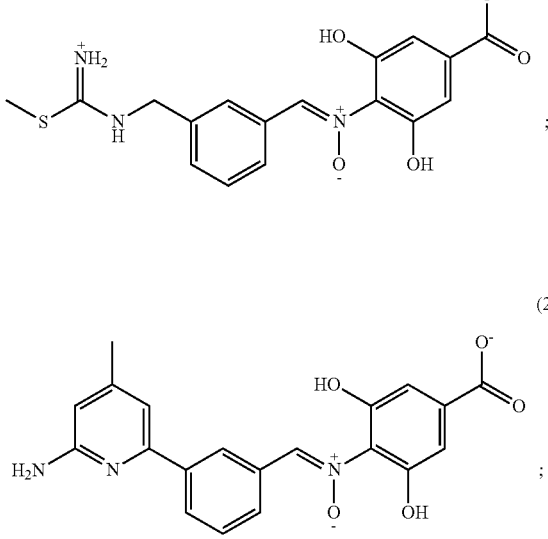

(24) 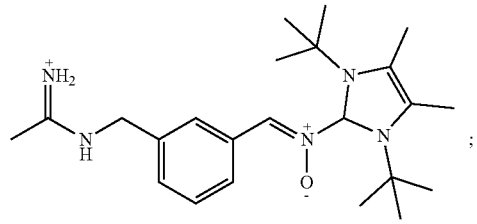
(25) 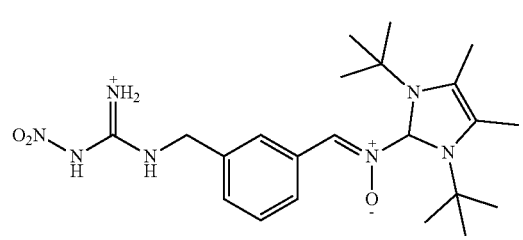
(26) 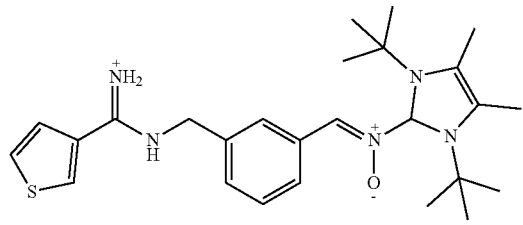
(27) 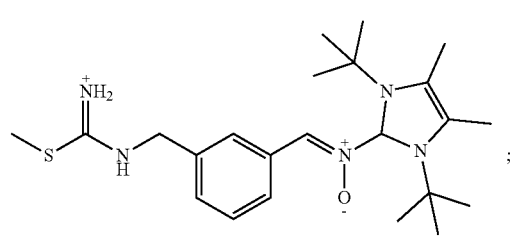
(28) 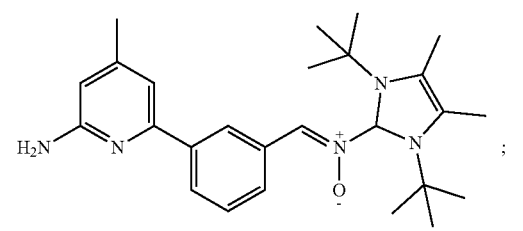
(29) 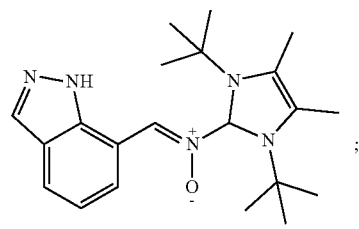
(30) 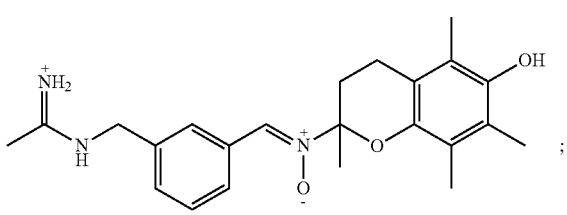
(31) 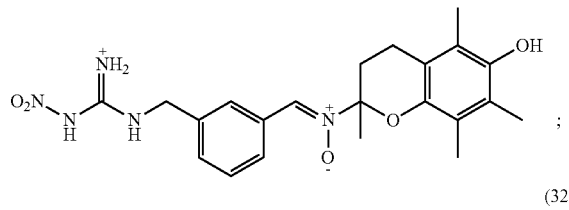
(32) 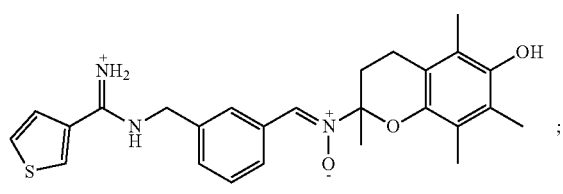
(33) 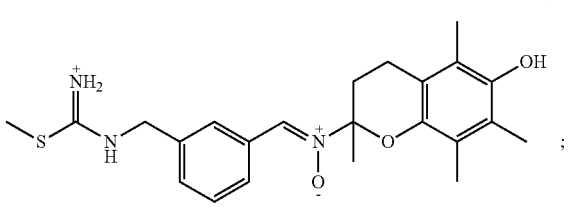
(34) 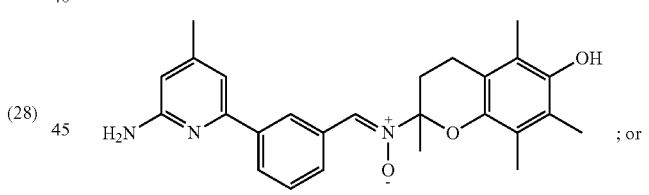
; or
(35) 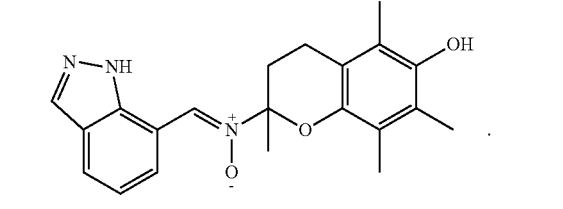
.
18. A pharmaceutical composition comprising an effective amount of a compound of claim 1 and a pharmaceutically acceptable diluent, carrier, or adjuvant.
19. A compound comprising formula (10) and salts, stereoisomers, racemates, solvates, hydrates, and polymorphs thereof, having Formula (10):

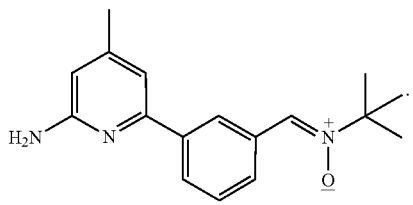
(10)

20. A compound comprising formula (16) and salts, stereoisomers, racemates, solvates, hydrates, and polymorphs thereof, having Formula (16):

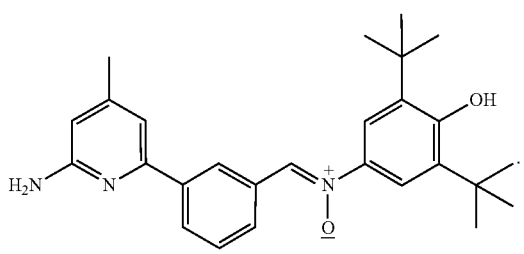
(16)

21. A compound comprising formula (22) and salts, stereoisomers, racemates, solvates, hydrates, and polymorphs thereof, having Formula (22):

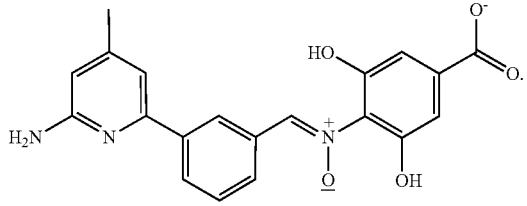
(22)

22. A compound comprising formula (28) and salts, stereoisomers, racemates, solvates, hydrates, and polymorphs thereof, having Formula (28):

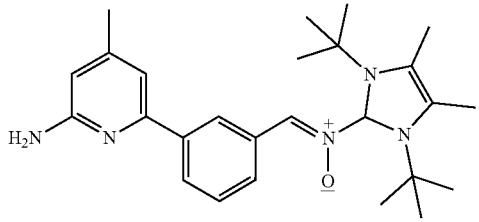
(28)

23. A compound comprising formula (34) and salts, stereoisomers, racemates, solvates, hydrates, and polymorphs thereof, having Formula (34):

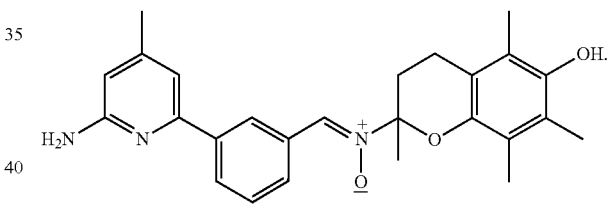
(34)

* * * * *

UNITED STATES PATENT AND TRADEMARK OFFICE
CERTIFICATE OF CORRECTION

| | | |
|---|---|---|
| PATENT NO. | : 10,829,441 B2 | Page 1 of 5 |
| APPLICATION NO. | : 16/176254 | |
| DATED | : November 10, 2020 | |
| INVENTOR(S) | : Kevin M. Nash, Isaac Schiefer and Zahoor Shah | |

It is certified that error appears in the above-identified patent and that said Letters Patent is hereby corrected as shown below:

In the Claims

Column 50, Line 50-60, please correct Claim 17, chemical depiction (10) to be removed as show below:

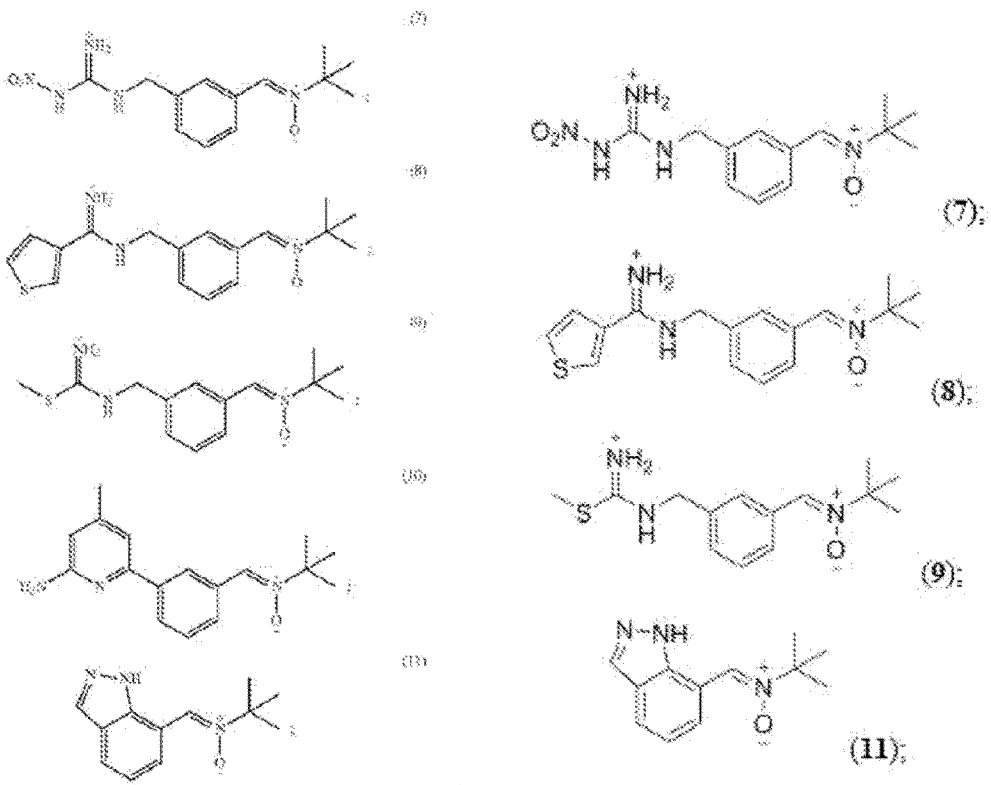

to:

Signed and Sealed this
Thirteenth Day of July, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,829,441 B2

Page 2 of 5

Column 51, Line 45-55, please correct Claim 17, chemical depiction (16) to be removed as shown below:

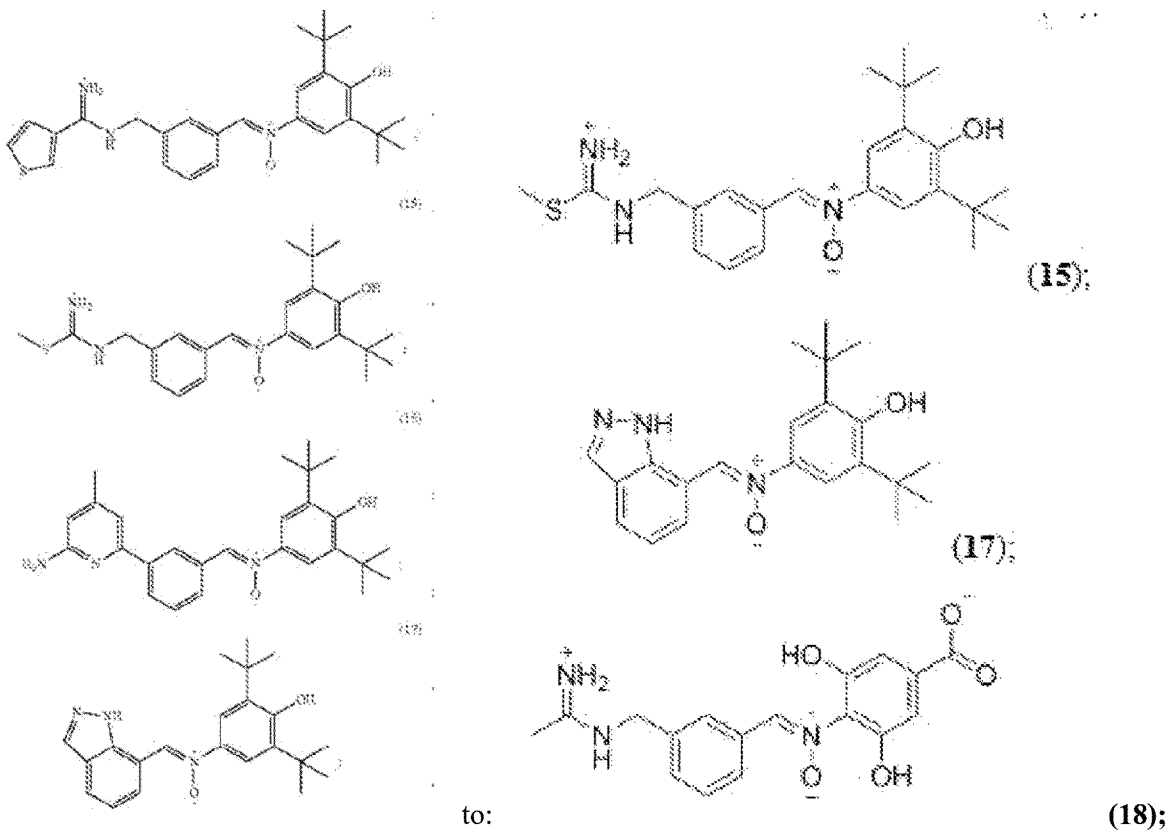

to: (18);

CERTIFICATE OF CORRECTION (continued)
U.S. Pat. No. 10,829,441 B2

Page 3 of 5

Column 52, Line 45-55, please correct Claim 17, chemical depiction (22) to be removed as shown below:

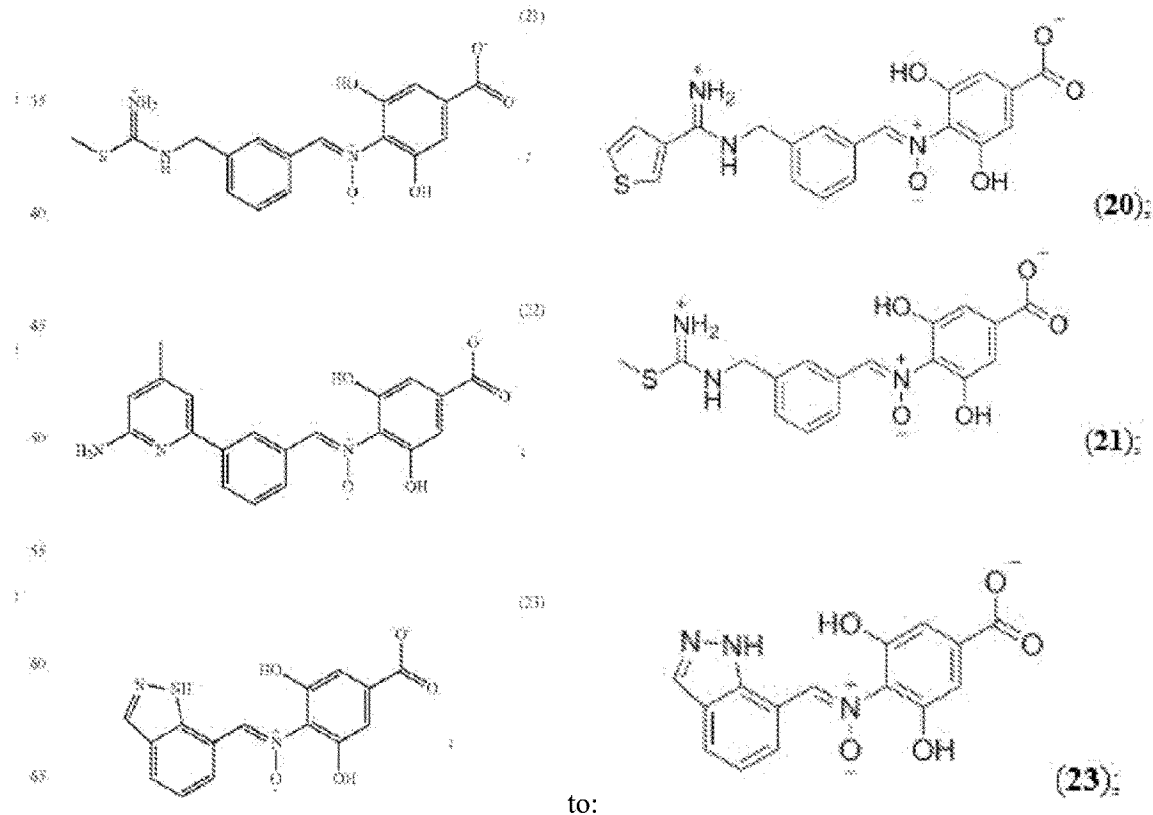

to:

CERTIFICATE OF CORRECTION (continued)
U.S. Pat. No. 10,829,441 B2

Column 53, Line 45-55, please correct Claim 17, chemical depiction (28) to be removed as shown below:

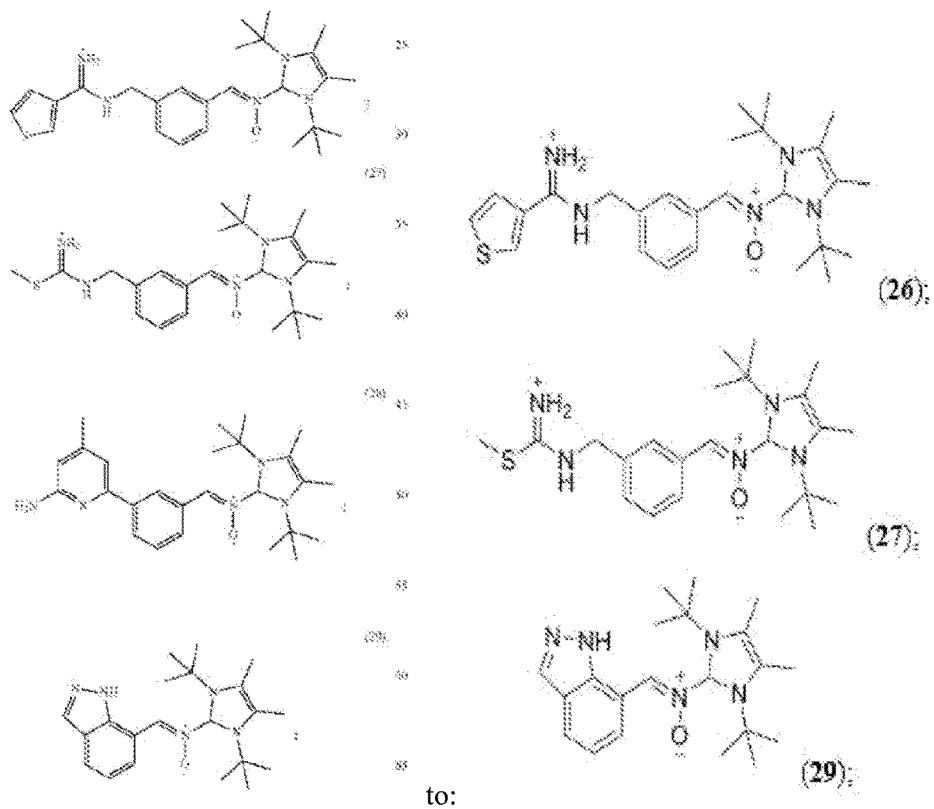

to:

CERTIFICATE OF CORRECTION (continued)
U.S. Pat. No. 10,829,441 B2

Column 54, Line 40-50, please correct Claim 17, chemical depiction (34) to be removed as shown below:

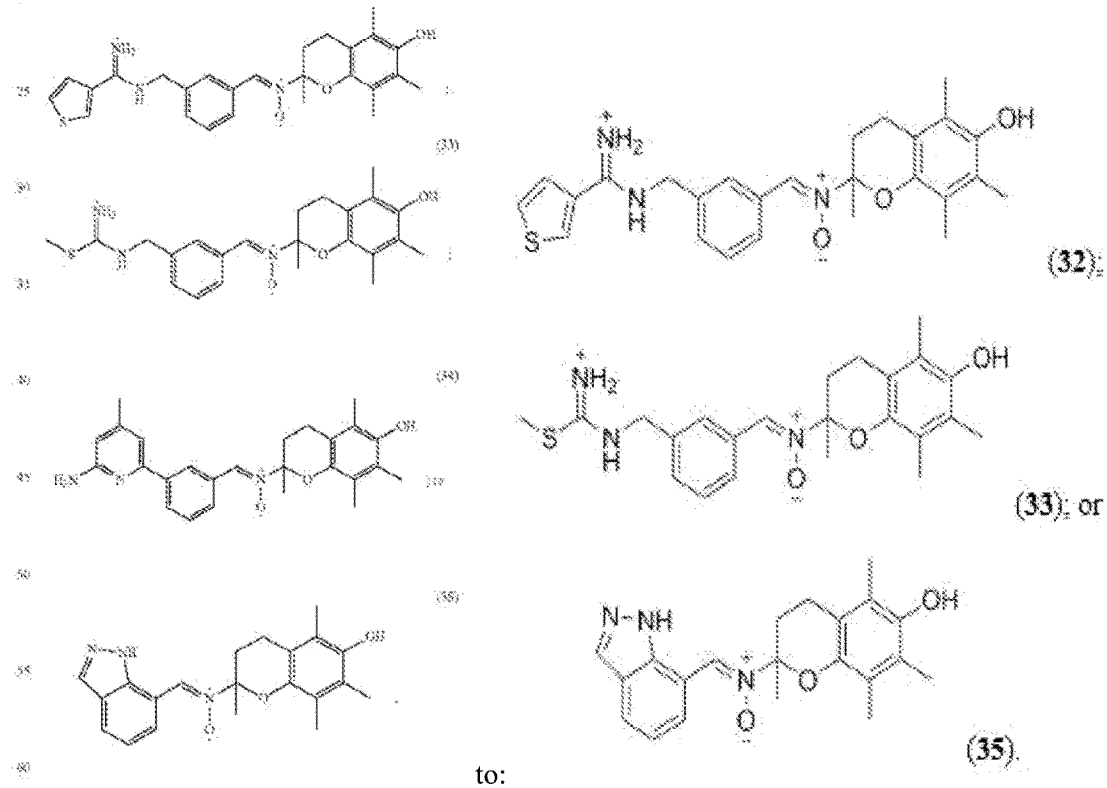

to: